US010689452B2

(12) United States Patent
Kontermann et al.

(10) Patent No.: US 10,689,452 B2
(45) Date of Patent: Jun. 23, 2020

(54) MONOVALENT ANTI-HUTNFR1 ANTIBODIES, ENCODING NUCLEIC ACIDS THEREOF AND METHODS OF TREATMENT THEREOF

(71) Applicants: UNIVERSITÄT STUTTGART, Stuttgart (DE); BALIOPHARM AG, Basel (CH)

(72) Inventors: Roland Kontermann, Nürtingen (DE); Klaus Pfizenmaier, Tiefenbronn (DE); Fabian Richter, Kirchheim (DE); Kirstin Zettlitz, Sherman Oaks, CA (US); Peter Scheurich, Stuttgart (DE); Andreas Herrmann, Pfeffingen (CH)

(73) Assignees: UNIVERSITÄT STUTTGART, Stuttgart (DE); BALIOPHARM AG, Basel (CH)

( * ) Notice: Subject to any disclaimer, the term of this patent is extended or adjusted under 35 U.S.C. 154(b) by 0 days.

(21) Appl. No.: 16/091,456

(22) PCT Filed: Apr. 4, 2017

(86) PCT No.: PCT/EP2017/057997
§ 371 (c)(1),
(2) Date: Oct. 4, 2018

(87) PCT Pub. No.: WO2017/174586
PCT Pub. Date: Oct. 12, 2017

(65) Prior Publication Data
US 2019/0144555 A1 May 16, 2019

(30) Foreign Application Priority Data
Apr. 5, 2016 (EP) .................................... 16163822

(51) Int. Cl.
*C07K 16/28* (2006.01)
*A61P 37/06* (2006.01)
(52) U.S. Cl.
CPC .......... *C07K 16/2878* (2013.01); *A61P 37/06* (2018.01); *C07K 2317/24* (2013.01); *C07K 2317/565* (2013.01); *C07K 2317/567* (2013.01); *C07K 2317/622* (2013.01); *C07K 2317/76* (2013.01); *C07K 2317/92* (2013.01); *C07K 2317/94* (2013.01)
(58) Field of Classification Search
CPC ............ C07K 16/2878; C07K 2317/24; C07K 2317/565; C07K 2317/567; C07K 2317/76; C07K 2317/622; C07K 2317/92; C07K 2317/94; A61P 37/06
See application file for complete search history.

(56) References Cited

U.S. PATENT DOCUMENTS 6,331,415 B1 12/2001 Cabilly et al.
9,045,535 B2 * 6/2015 Pfizenmaier ....... C07K 16/2878

FOREIGN PATENT DOCUMENTS

WO  2008/113515  9/2008
WO  2012/035141  3/2012

OTHER PUBLICATIONS

Paul, WE (1993) Fundamental Immunology, 3rd ed. Raven Press, NY, Chap. 9, pp. 292-295.*
Rudikoff, S et al. (1982) Proc. Natl. Acad. Sci. USA, 79:1979-1983.*
Colman, PM (1994) Research in Immunology, Elsevier, NY, 145(1):33-36.*
Abhinandan KR, et al., "Analyzing the "degree of humanness" of antibody sequences.", J Mol Biol. 2007 369(3):852-62.
Armour KL, et al., "Recombinant human IgG molecules lacking Fcgamma receptor I binding and monocyte triggering activities", Eur J Immunol. Aug. 1999;29(8):2613-24.
Berger V, et al., "An Anti-TNFRI scFv-HAS fusion protein as selective antagonist of TNF action", Protein Engineering, Design and Selection, vol. 26, No. 10, 4 Sep. 2013 (Sep. 4, 2013), pp. 581-587, XP055279872.
Brodeur, et al., "Mouse-Human Myeloma Partners for the Production of Heterohybridomas", Monoclonal Antibody Production Techniques and Applications, (Marcel Dekker, Inc., New York), 1987, pp. 51-63.
Choy EH, Hazleman B, Smith M, Moss K, Lisi L, Scott DG, Patel J, Sopwith M, Isenberg DA., (Oxford). Rheumatology (Oxford). Oct. 2002;41(10):1133-7.
Fischer R, et al., "Targeting sTNF/TNFR1 Signaling as a New Therapeutic Strategy", Antibodies, 2015, 4:48-70.
Goodall, et al., "Pharmacokinetic and Pharmacodynamic Characterisation of an Anti-Mouse TNF Receptor 1 Domain Antibody Formatted for In Vivo Half-Life Extension", PLOS ONE, 2015, vol. 10, No. 9, e0137065.
Gu, et al., "Identification of Anti-EGFR and Anti-ErbB3 Dual Variable Domains Immunoglobulin (DVD-Ig) Proteins with Unique Activities", PLoS One. 2015; 10(5): e0124135. Published online May 21, 2015. doi: 10.1371/journal.pone.0124135.
Hellendoorn et al., "Limiting the risk of immunogenicity by identification and removal of T-cell epitopes (DeImmunisation™)", Cancer Cell International 4 (Suppl. I), 2004, S20. (2004).
Hwang WY, et al., "Use of human germline genes in a CDR homology-based approach to antibody humanization", Methods 36, 2005, 35-42.
Jones PT, et al., "Replacing the complementarity-determining regions in a human antibody with those from a mouse", Nature 321, 1986, 522-525.

(Continued)

*Primary Examiner* — Robert S Landsman
(74) *Attorney, Agent, or Firm* — Meunier Carlin & Curfman LLC

(57) ABSTRACT

The invention provides for an inhibitor of the huTNFRI receptor which is a human or humanized antibody construct that monovalently recognizes huTNFRI through an antigen-binding moiety, which is characterized by specific CDR sequences, a pharmaceutical preparation thereof, method of producing the inhibitor and the medical use of the inhibitor.

24 Claims, 23 Drawing Sheets

Figure 2:
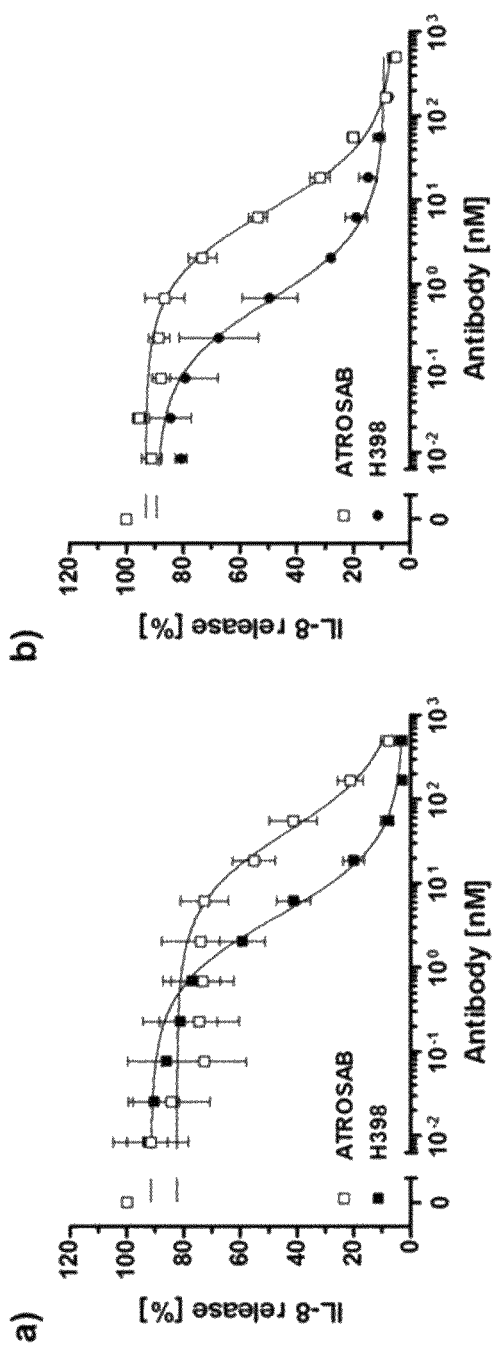

Specification includes a Sequence Listing.

(56) References Cited

OTHER PUBLICATIONS

Kashmiri SV, et al., "SDR grafting—a new approach to antibody humanization", Methods 36, 2005, 25-34.

Köhler, et al., "Continuous cultures of fused cells secreting antibody of predefined specificity", Nature, 1975, 256:495-497.

Kontermann RE, et al., "A Humanized Tumor Necrosis Factor Receptor 1 (TNFR1)-specific Antagonistic Antibody for Selective Inhibition of Tumor Necrosis Factor (TNF) Action", Journal of Immunotherapy 2008, 31(3):225-234.

Kozbor, et al., "A human hybrid myeloma for production of human monoclonal antibodies.", J. Immunol., 1984, 133:3001.

Lee, et al., "Expression and functional reconstitution of a recombinant antibody (Fab') specific for human apolipoprotein B-100", J. Biotechnology, 2003, 101:189-198.

Lefranc, et al., "IMGT, the international ImMunoGeneTics database",Nucleic Acids 1999, Res. 27: 209-212.

Lifely MR, et al., "Glycosylation and biological activity of CAMPATH-1H expressed in different cell lines and grown under different culture conditions", Glycobiology, 1995, 5: 813-822.

Locksley, et al., The TNF and TNF receptor superfamilies: integrating mammalian biology, Cell, 2001, 104:487-501.

Merchant M, et al., "Monovalent antibody design and mechanism of action of onartuzumab, a MET antagonist with anti-tumor activity as a therapeutic agent", Proc Natl Acad Sci U S A. Aug. 6, 2013; 110(32): E2987-E2996. Published online Jul. 23, 2013. doi: 10.1073/pnas.1302725110.

Mohler KM, et al., "Soluble tumor necrosis factor (TNF) receptors are effective therapeutic agents in lethal endotoxemia and function simultaneously as both TNF carriers and TNF antagonists.", J Immunol Aug. 1, 1993, 151 (3) 1548-1561.

Moosmayer D, et al., "A single-chain TNF receptor antagonist is an effective inhibitor of TNF mediated cytotoxicity." Ther. Immunol., 1995, 2:31-40.

Muller D, et al., "Improved pharmacokinetics of recombinant bispecific antibody molecules by fusion to human serum albumin.", J. Biol. Chem (2007) 282(17):12650-60.

Muller D, et al., "Murine endoglin-specific single-chain Fv fragments for the analysis of vascular targeting strategies in mice.", J. Immunol. Methods, 2008, 339(1): 90-8.

Olleros, et al., "Dominant-Negative Tumor Necrosis Factor Protects from *Mycobacterium bovis* Bacillus Calmette-Guérin (BCG) and Endotoxin-Induced Liver Injury without Compromising Host Immunity to BCG and *Mycobacterium tuberculosis*", J. Infect. Dis. 2009, 199:1053-63.

Richter, et al., "Antagonistic TNF Receptor One-Specific Antibody (ATROSAB): Receptor Binding and In Vitro Bioactivity", PLoS One 2013, 8:e72156.

Rogusk,a et al., "Humanization of murine monoclonal antibodies through variable domain resurfacing.", Proc. Natl. Acad. Sci. USA, 1994, 91, 969-973.

Rudikoff, et al., "Single amino acid substitution altering antigen-binding specificity", PNAS, 1982, vol. 79, pp. 1979-1983.

Shields RL, et al., "High resolution mapping of the binding site on human IgG1 for FcγRI, FcγRII, FcγRIII, and FcRn and design of IgG1 variants with improved binding to the FcγR", J Biol Chem. Mar. 2, 2001;276(9):6591-604. Epub Nov. 28, 2000.

Shibata H, et al., "The therapeutic effect of TNFR1-selective antagonistic mutant TNF-alpha in murine hepatitis models", Cytokine, 2008, 2:229-33.

Umana P, et al., "Engineered glycoforms of an antineuroblastoma IgG1 with optimized antibody-dependent cellular cytotoxic activity", Nature Biotech. 1999, 17:176-180.

Wark, et al., "Latest technologies for the enhancement of antibody affinity", Advanced Drug Delivery Reviews 2006, 58: 657-670.

Wibbenmeyer JA, et al., "Cloning, expression, and characterization of the Fab fragment of the anti-lysozyme antibody HyHEL-5", Biochim Biophys Acta 1999, 1430:191-202.

Zettlitz KA, et al., "ATROSAB, a humanized antagonistic anti-tumor necrosis factor receptor one-specific antibody", MAbs. 2010 2(6):639-47.

Zettlitz KA, Thesis 2010, 120 pages. Universität Stuttgart, URL:http://elib.uni-stuttgart.de/bitstream /11682/2035/1/Diss Kirstin Zettlitz.pdf.

International Search Report and Written Opinion dated Jul. 31, 2017, from International Application No. PCT/EP2017/057997, 21 pages.

International Preliminary Report on Patentability dated Oct. 9, 2018, from International Application No. PCT/EP2017/057997, 12 pages.

Partial European Search Report issued for European Application No. 16163822, dated Jun. 22, 2016, 9 pages.

Extended European Search Report issued for European Application No. 16163822, dated Oct. 4, 2016, 11 pages.

Duebel, S. "Handbook of Therapeutic Antibodies Chapter 6", Jan. 1, 2007, pp. 119-144.

\* cited by examiner

Fig. 1
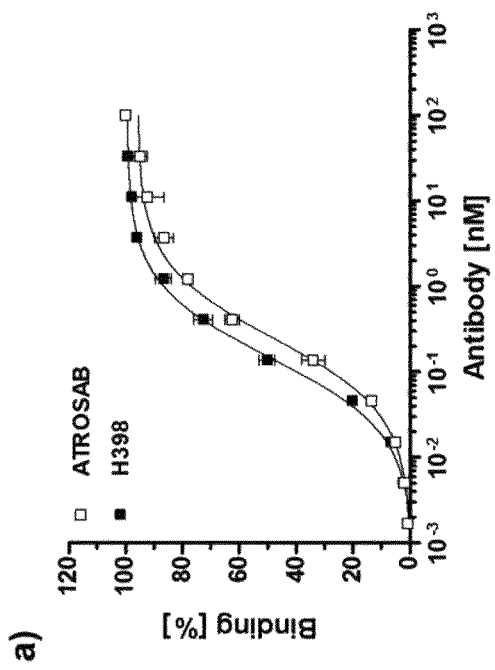
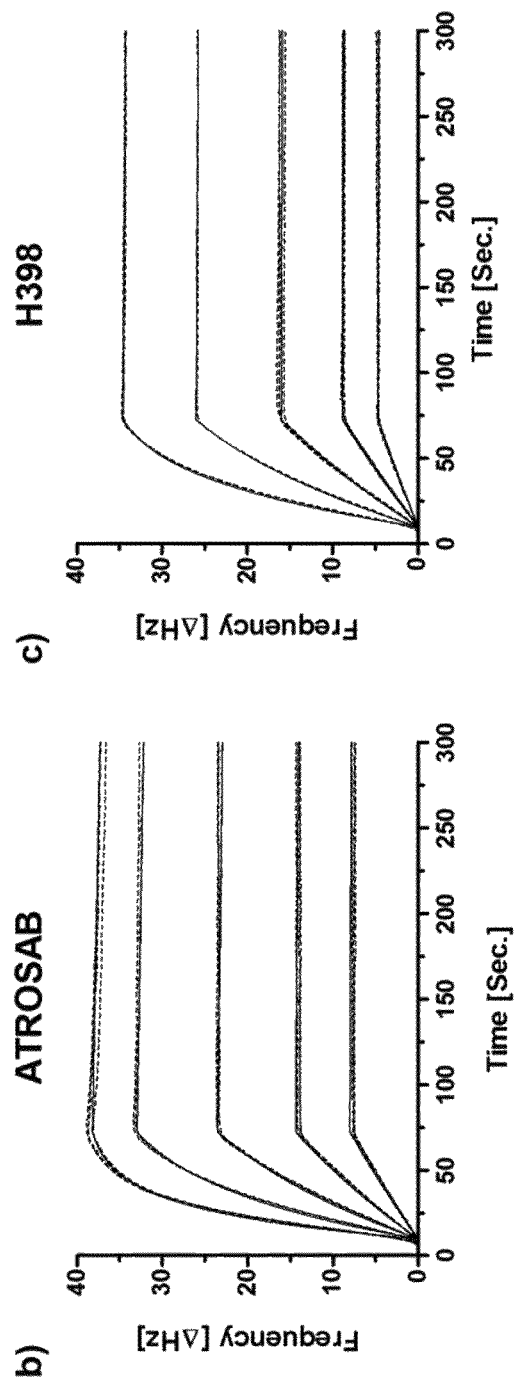

Fig. 4 a)
```
                      FR1                                 CDRH1   FR2                CDRH2
Kabat                 12345678910234567892023456789 3     02345   67894023456789     502a3456789602345
scFvIZI06.1           QVQLVQSGAEVKKPGSSVKVSCKASGYTFT      DFYIN   WVRQAPGQGLEWIG     EIYPYSGHAYYNEKFKA
scFvIG11              ..............................      .....   ..............     ..V.TQ.E.K..D....
scFvT12B              H.............................      .....   ..............     ..V.SQ.E.K..D....
scFvFRK13.7           H.............................      .....   ..............     ..V.SQ.E.K..D....

FR3                                          CDRH3   FR4
Kabat                 67897023456789802abc345678990234              567891  003456789110
scFvIZI06.1           RVTITADKSTSTAYMELSSLRSEDTAVYYCAR              WDFLDY  WGQGTTVTVSS
scFvIG11              ...............................              ......  ...........
scFvT12B              ...............................              ......  ...........
scFvFRK13.7           ...............................              ......  ...........
``` b)
```
                      FR1                          CDRL1            FR2                CDRL2
Kabat                 12345678910234567892023       4567abcde8930234 567894023456789    5023456
scFvIZI06.1           DIVMTQSPLSLPVTPGEPASISC       RSSQSLLHSNGNTYLH WYLQKPGQSPQLLIY    TVSNRFS
scFvIG11              .......................       ................ ...............    .......
scFvT12B              .......................       ................ ...............    .......
scFvFRK13.7           .VQ.....S..SASV.DRVT.T.       ................ ..Q....KA.K....    .......

FR3                                       CDRL3      FR4
Kabat                 78960234567897023456789802345678           990234567  89100345678
scFvIZI06.1           GVPDRFSGSGSGTDFTLKISRVEAEDVGVYYC           SQSTHVPYT  FGGGTKVEIKR
scFvIG11              ................................           .........  ...........
scFvT12B              ................................           ..G......  ...........
scFvFRK13.7           ...S............T..SLQP..FAT...           ..S......  ...........
```

Fig. 7 a)
```
                 FR1                                CDRH1 FR2              CDRH2
Kabat            12345678910234567892023456789३     02345 67894023456789    502a3456789602345
scFvIZI06.1      QVQLVQSGAEVKKPGSSVKVSCKASGYTFT     DFYIN WVRQAPGQGLEWIG    EIYPYSGHAYYNEKFKA
FRK13.1          .....E..GGLV...G.LRL..A...F..S     ..... .I.....K....VS    ....G............
FRK13.2          .....E..GGLV...G.LRL..A...F..S     ..... .I.....K....VS    ....G............

FR3                                         CDRH3  FR4
Kabat            67897023456789802abc345678990234             567891 003456789110
scFvIZI06.1      RVTITADKSTSTAYMELSSLRSEDTAVYYCAR             WDFLDY WGQGTTVTVSS
FRK13.1          .F..SR.NAKNSL.LQMN...A..........             ...... ...........
FRK13.2          .F..SA.NAKNSL.LQMN...A..........             ...... ...........
``` b)
```
                 FR1                           CDRL1            FR2              CDRL2
Kabat            12345678910234567892023        4567abcde8930234 567894023456789  5023456
scFvIZI06.1      DIVMTQSPLSLPVTPGEPASISC        RSSQSLLHSNGNTYLH WYLQKPGQSPQLLIY  TVSNRFS
FRK13.1          .IQ.....S..SASV.DRVT.T.        ................ ..Q....KA.K....  .......
FRK13.2          .VQ.....S..SASV.DRVT.T.        ................ ..Q....KA.K....  .......

FR3                                   CDRL3      FR4
Kabat            78960234567897023456789802345678      990234567  89100345678
scFvIZI06.1      GVPDRFSGSGSGTDFTLKISRVEAEDVGVYYC      SQSTHVPYT  FGGGTKVEIKR
FRK13.1          ...S.............T..SLQP..FAT...      .........  ...........
FRK13.2          ...S.............T..SLQP..FAT...      .........  ...........
```

Fig. 11
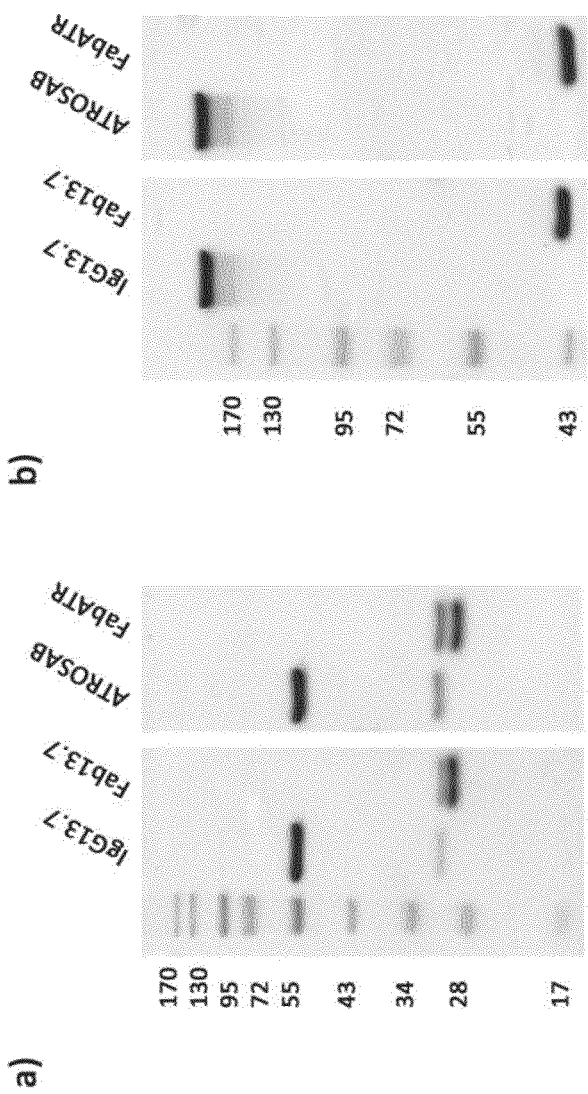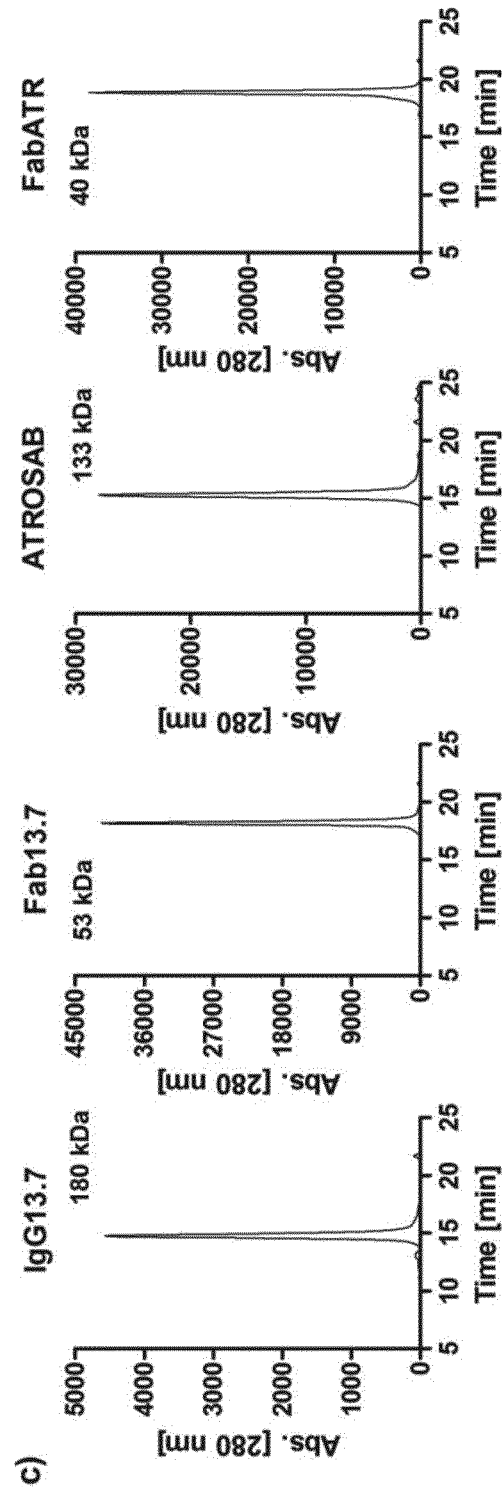

Fig. 18
Fig. 19
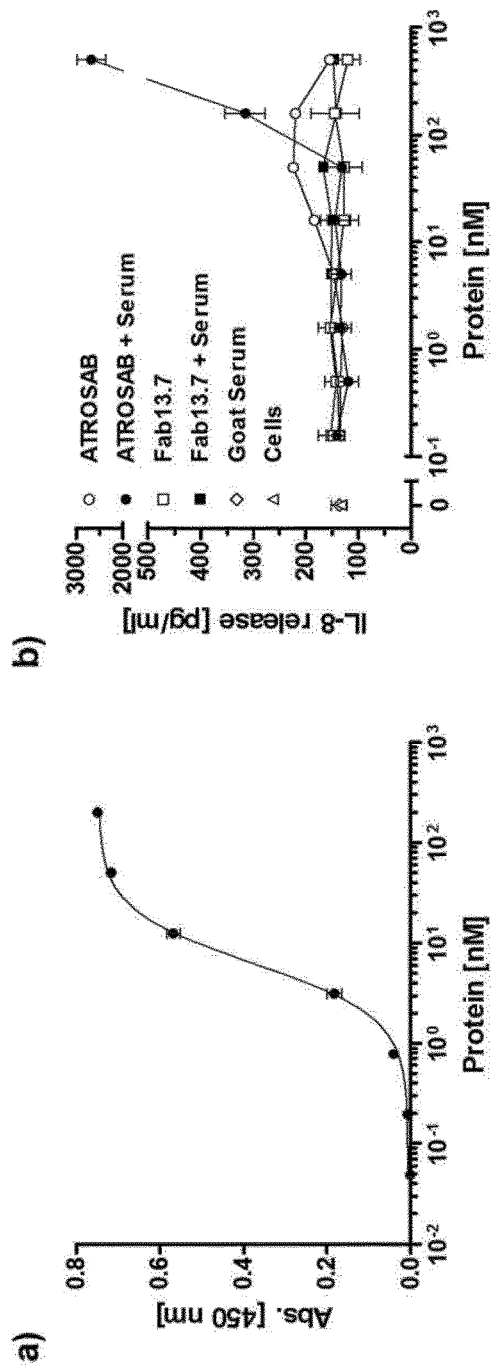
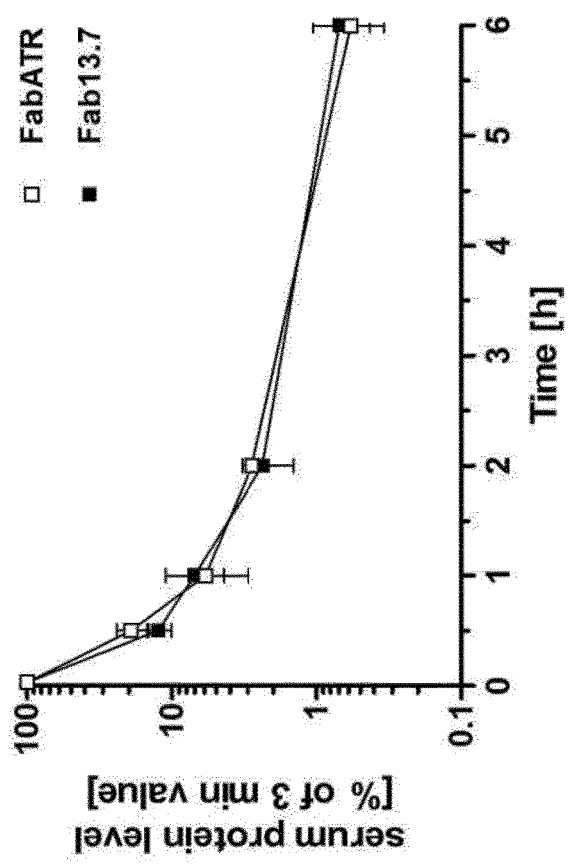

Fig. 20
a)
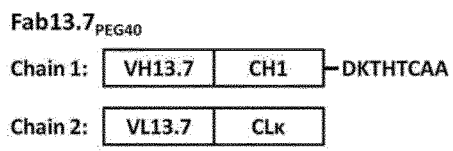
b)
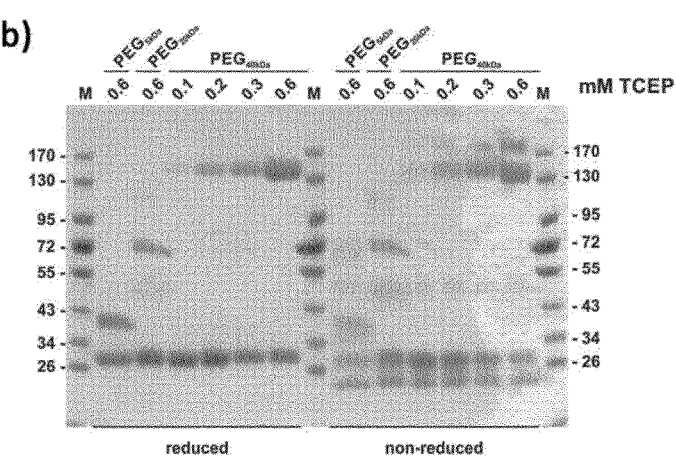
c) 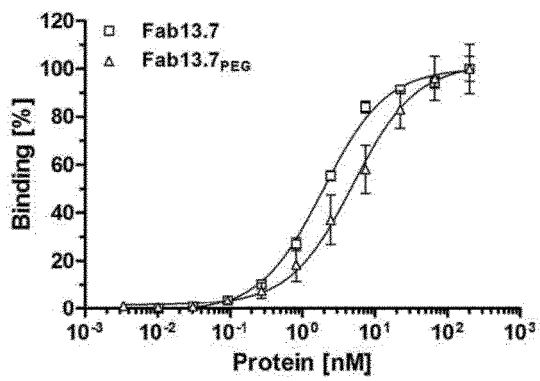
d) 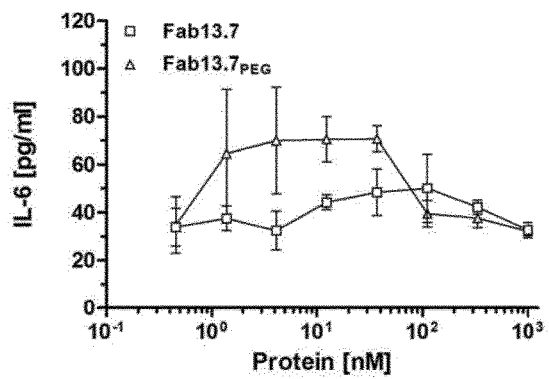
e) 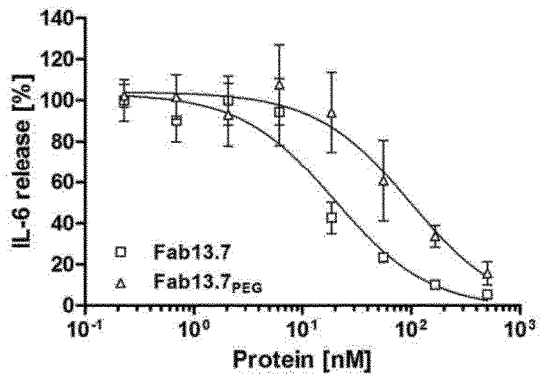
f) 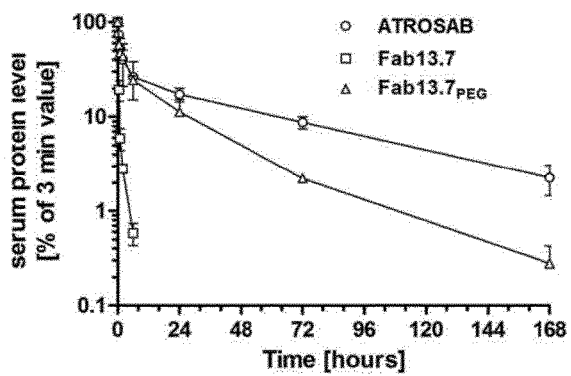

Fig. 21
a)
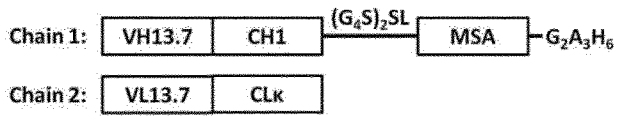
b)
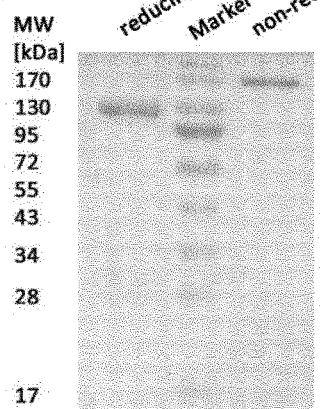
c)
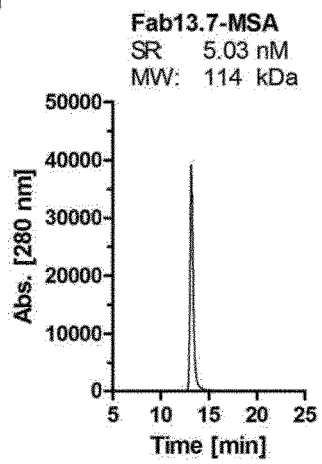
d)
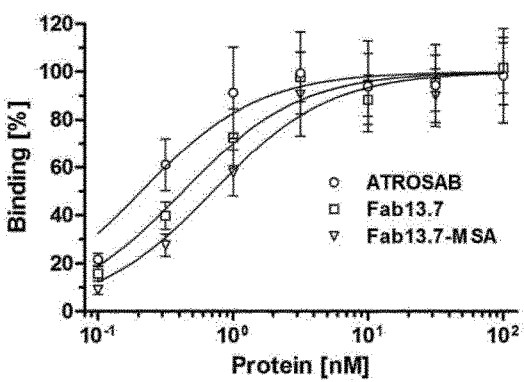
e)
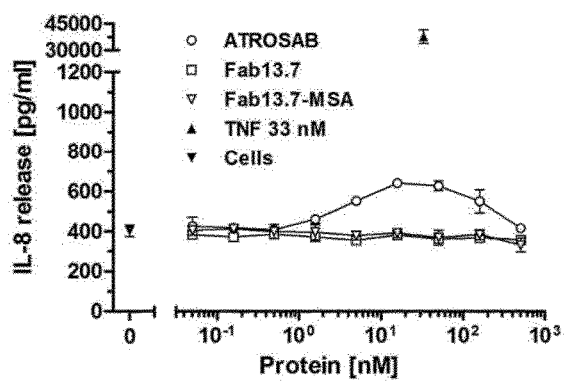
f)
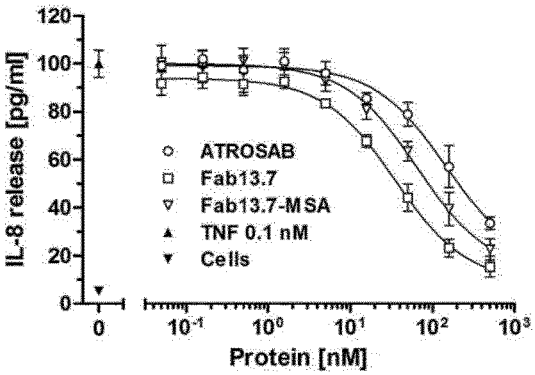
g)
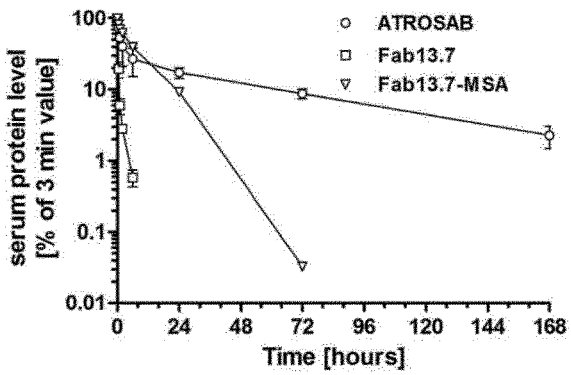

Fig. 22
a)
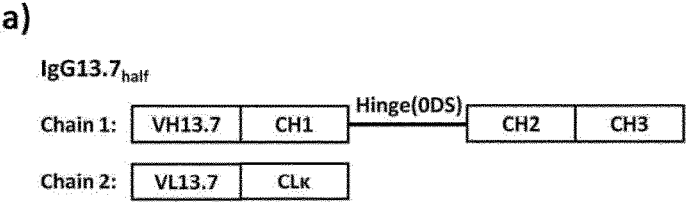
b) 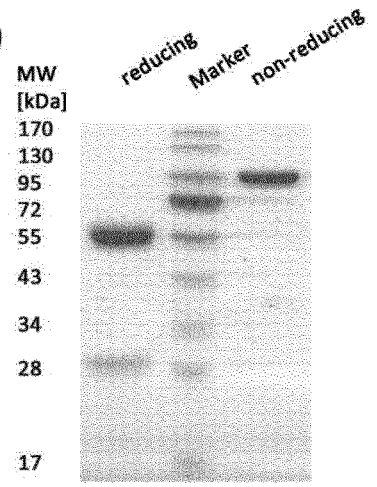
c) 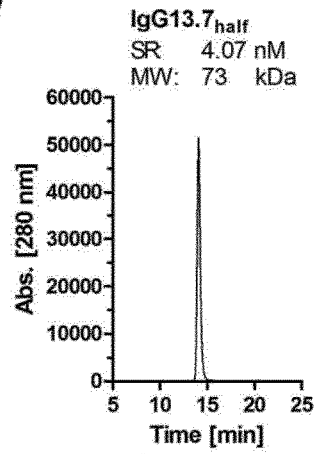
d) 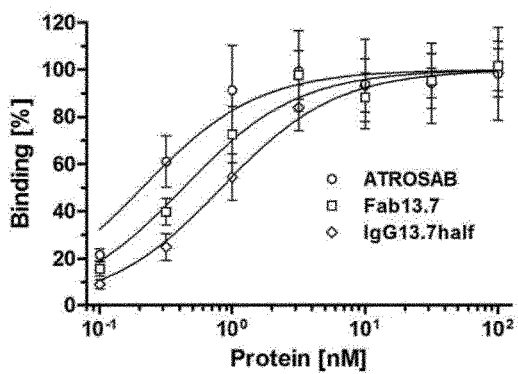
e) 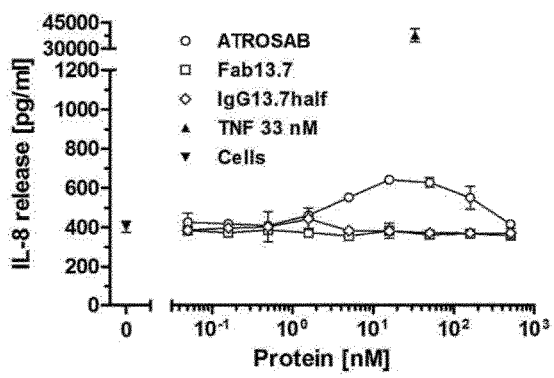
f) 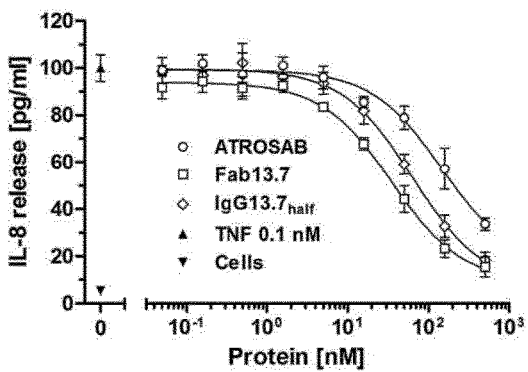
g) 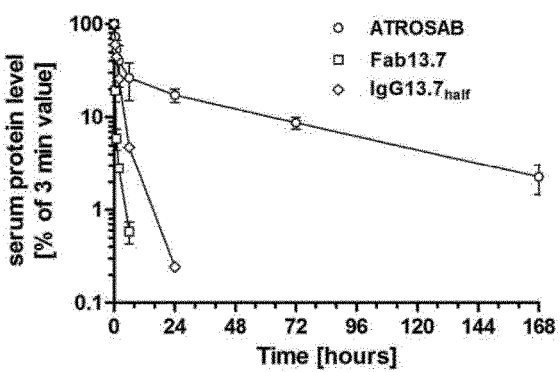

Fig. 23
a)
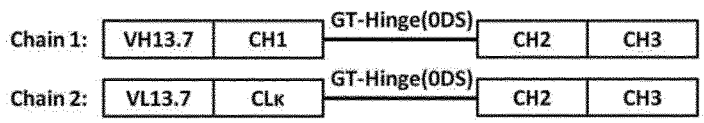
b) 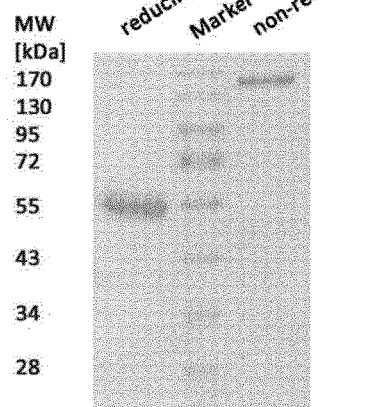
c) 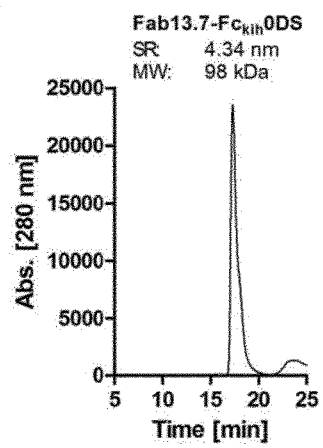
d) 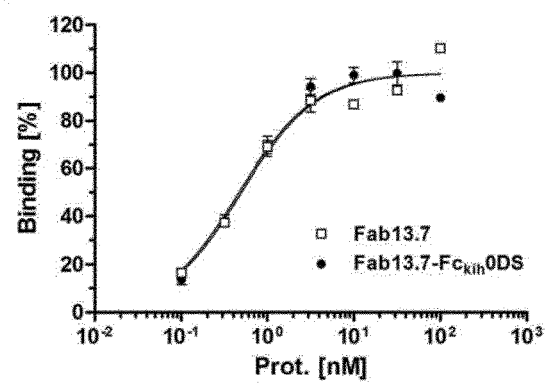
e) 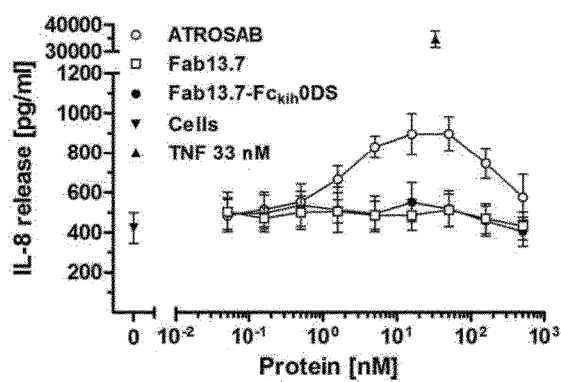
f) 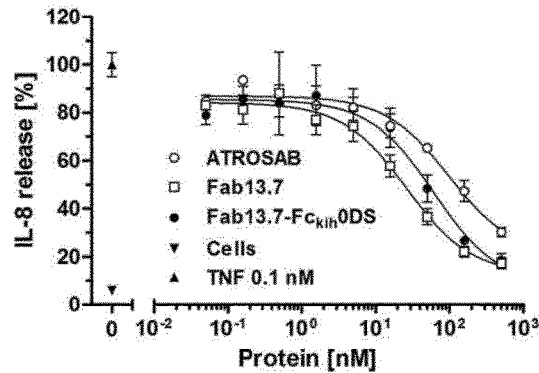
g) 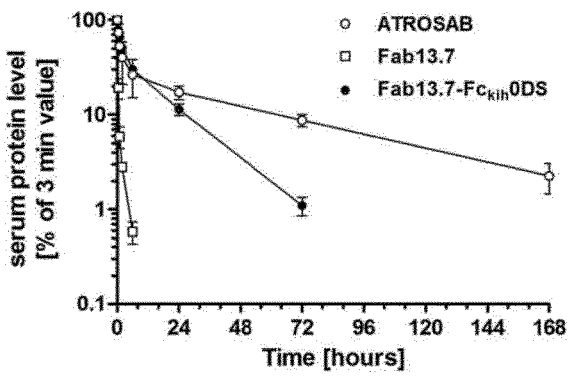

Fig. 25

SEQ ID 1: DFYIN

SEQ ID 2: EIYPYSGHAYYNEKFKA

SEQ ID 3: WDFLDY

SEQ ID 4: RSSQSLLHSNGNTYLH

SEQ ID 5: TVSNRFS

SEQ ID 6: SQSTHVPYT

SEQ ID 7: EIXPXXGXAXYNXKFKA
Wherein
X at position 3 is any of Y or V,
X at position 5 is any of Y, T or S,
X at position 6 is any of S or Q,
X at position 8 is any of H or E,
X at position 10 is any of Y or K,
X at position 13 is any of E or D.

SEQ ID 8: SQXTHVPYT
Wherein X at position 3 is any of S or G.

SEQ ID 9: EIVPTQGEAKYNDKFKA

SEQ ID 10: EIVPXQGEAKYNDKFKA
Wherein
X at position 5 is any of S or G

SEQ ID 11: SQXTHVPYT
Wherein
X at position 3 is any of G or S

SEQ ID 12:
QVQLVQSGAEVKKPGSSVKVSCKASGYTFTDFYINWVRQAPGQGLEWIGEIVPTQGEAKYNDKFKARVTITADKSTSTAYMELSSLRSEDTAVYYCARWDFLDYWGQGTTVTVSS

SEQ ID 13:
HVQLVQSGAEVKKPGSSVKVSCKASGYTFTDFYINWVRQAPGQGLEWIGEIVPSQGEAKYNDKFKARVTITADKSTSTAYMELSSLRSEDTAVYYCARWDFLDYWGQGTTVTVSS

Fig. 25 (continued)

SEQ ID 14:
QVQLVESGGGLVKPGGSLRLSCAASGFTFSDFYINWIRQAPGKGLEWVSEIYPYSGHA
YYNEKFKARFTISRDNAKNSLYLQMNSLRAEDTAVYYCARWDFLDYWGQGTTVTVSS

SEQ ID 15:
QVQLVESGGGLVKPGGSLRLSCAASGFTFSDFYINWIRQAPGKGLEWVSEIYPYSGHA
YYNEKFKARFTISADNAKNSLYLQMNSLRAEDTAVYYCARWDFLDYWGQGTTVTVSS

SEQ ID 16:
DIVMTQSPLSLPVTPGEPASISCRSSQSLLHSNGNTYLHWYLQKPGQSPQLLIYTVSNR
FSGVPDRFSGSGSGTDFTLKISRVEAEDVGVYYCSQSTHVPYTFGGGTKVEIKR

SEQ ID 17:
DIVMTQSPLSLPVTPGEPASISCRSSQSLLHSNGNTYLHWYLQKPGQSPQLLIYTVSNR
FSGVPDRFSGSGSGTDFTLKISRVEAEDVGVYYCSQGTHVPYTFGGGTKVEIKR

SEQ ID 18:
DIQMTQSPSSLSASVGDRVTITCRSSQSLLHSNGNTYLHWYQQKPGKAPKLLIYTVSN
RFSGVPSRFSGSGSGTDFTLTISSLQPEDFATYYCSQSTHVPYTFGGGTKVEIK

SEQ ID 19:
DVQMTQSPSSLSASVGDRVTITCRSSQSLLHSNGNTYLHWYQQKPGKAPKLLIYTVSN
RFSGVPSRFSGSGSGTDFTLTISSLQPEDFATYYCSQSTHVPYTFGGGTKVEIK

SEQ ID 20:
QVQLVQSGAEVKKPGSSVKVSCKASGYTFTDFYINWVRQAPGQGLEWIGEIYPYSGH
AYYNEKFKARVTITADKSTSTAYMELSSLRSEDTAVYYCARWDFLDYWGQGTTVTVSS

SEQ ID 21:
DIVMTQSPLSLPVTPGEPASISCRSSQSLLHSNGNTYLHWYLQKPGQSPQLLIYTVSNR
FSGVPDRFSGSGSGTDFTLKISRVEAEDVGVYYCSQSTHVPYTFGGGTKVEIKR

SEQ ID 22:
QVQLVQSGAEVKKPGSSVKVSCKASGYTFTDFYINWVRQAPGQGLEWIGEIYPYSGH
AYYNEKFKARVTITADKSTSTAYMELSSLRSEDTAVYYCARWDFLDYWGQGTTVTVSS
SEQ ID 23:
DIVMTQSPLSLPVTPGEPASISCRSSQSLLHSNGNTYLHWYLQKPGQSPQLLIYTVSNR
FSGVPDRFSGSGSGTDFTLKISRVEAEDVGVYYCSQSTHVPYTFGGGTKVEIKR

SEQ ID 24:
DKTHTCPPCPAPELLGGPSVFLFPPKPKDTLMISRTPEVTCVVVDVSHEDPEVKFNWY
VDGVEVHNAKTKPREEQYNSTYRVVSVLTVLHQDWLNGKEYKCKVSNKALPAPIEKTI
SKAKGQPREPQVYTLPPSRDELTKNQVSLTCLVKGFYPSDIAVEWESNGQPENNYKT
TPPVLDSDGSFFLYSKLTVDKSRWQQGNVFSCSVMHEALHNHYTQKSLSLSPGK

Fig. 25 (continued)

SEQ ID 25:
HVQLVQSGAEVKKPGSSVKVSCKASGYTFTDFYINWVRQAPGQGLEWIGEIVPSQGE
AKYNDKFKARVTITADKSTSTAYMELSSLRSEDTAVYYCARWDFLDYWGQGTTVTVS
SASTKGPSVFPLAPSSKSTSGGTAALGCLVKDYFPEPVTVSWNSGALTSGVHTFPAVL
QSSGLYSLSSVVTVPSSSLGTQTYICNVNHKPSNTKVDKKVEPKSC

SEQ ID 26:
DVQMTQSPSSLSASVGDRVTITCRSSQSLLHSNGNTYLHWYQQKPGKAPKLLIYTVSN
RFSGVPSRFSGSGSGTDFTLTISSLQPEDFATYYCSQSTHVPYTFGGGTKVEIKRTVA
APSVFIFPPSDEQLKSGTASVVCLLNNFYPREAKVQWKVDNALQSGNSQESVTEQDS
KDSTYSLSSTLTLSKADYEKHKVYACEVTHQGLSSPVTKSFNRGEC

SEQ ID 27:
HVQLVQSGAEVKKPGSSVKVSCKASGYTFTDFYINWVRQAPGQGLEWIGEIVPSQGE
AKYNDKFKARVTITADKSTSTAYMELSSLRSEDTAVYYCARWDFLDYWGQGTTVTVS
SASTKGPSVFPLAPSSKSTSGGTAALGCLVKDYFPEPVTVSWNSGALTSGVHTFPAVL
QSSGLYSLSSVVTVPSSSLGTQTYICNVNHKPSNTKVDKKVEPKSCDKTHTCAA

SEQ ID 28:
HVQLVQSGAEVKKPGSSVKVSCKASGYTFTDFYINWVRQAPGQGLEWIGEIVPSQGE
AKYNDKFKARVTITADKSTSTAYMELSSLRSEDTAVYYCARWDFLDYWGQGTTVTVS
SASTKGPSVFPLAPSSKSTSGGTAALGCLVKDYFPEPVTVSWNSGALTSGVHTFPAVL
QSSGLYSLSSVVTVPSSSLGTQTYICNVNHKPSNTKVDKKVEPKSCGGGGSGGGGSS
LEAHKSEIAHRYNDLGEQHFKGLVLIAFSQYLQKCSYDEHAKLVQEVTDFAKTCVADES
AANCDKSLHTLFGDKLCAIPNLRENYGELADCCTKQEPERNECFLQHKDDNPSLPPFE
RPEAEAMCTSFKENPTTFMGHYLHEVARRHPYFYAPELLYYAEQYNEILTQCCAEADK
ESCLTPKLDGVKEKALVSSVRQRMKCSSMQKFGERAFKAWAVARLSQTFPNADFAEI
TKLATDLTKVNKECCHGDLLECADDRAELAKYMCENQATISSKLQTCCDKPLLKKAHC
LSEVEHDTMPADLPAIAADFVEDQEVCKNYAEAKDVFLGTFLYEYSRRHPDYSVSLLL
RLAKKYEATLEKCCAEANPPACYGTVLAEFQPLVEEPKNLVKTNCDLYEKLGEYGFQN
AILVRYTQKAPQVSTPTLVEAARNLGRVGTKCCTLPEDQRLPCVEDYLSAILNRVCLLH
EKTPVSEHVTKCCSGSLVERRPCFSALTVDETYVPKEFKAETFTFHSDICTLPEKEKQI
KKQTALAELVKHKPKATAEQLKTVMDDFAQFLDTCCKAADKDTCFSTEGPNLVGGAA
AHHHHHH

SEQ ID 29:
HVQLVQSGAEVKKPGSSVKVSCKASGYTFTDFYINWVRQAPGQGLEWIGEIVPSQGE
AKYNDKFKARVTITADKSTSTAYMELSSLRSEDTAVYYCARWDFLDYWGQGTTVTVS
SASTKGPSVFPLAPSSKSTSGGTAALGCLVKDYFPEPVTVSWNSGALTSGVHTFPAVL
QSSGLYSLSSVVTVPSSSLGTQTYICNVNHKPSNTKVDKKVEPKSCDKTHTSPPSPAP
ELLGGPSVFLFPPKPKDTLMISRTPEVTCVVVDVSHEDPEVKFNWYVDGVEVHNAKTK
PREEQYNSTYRVVSVLTVLHQDWLNGKEYKCKVSNKALPAPIEKTISKAKGQPREPQV
YTLPPSRDELTKNQVSLTCLVKGFYPSDIAVEWESNGQPENNYKTTAPVLDSDGSFRL
RSDLTVDKSRWQQGNVFSCSVMHEALHNHYTQKSLSLSPGK

Fig. 25 (continued)

SEQ ID 30:
HVQLVQSGAEVKKPGSSVKVSCKASGYTFTDFYINWVRQAPGQGLEWIGEIVPSQGE
AKYNDKFKARVTITADKSTSTAYMELSSLRSEDTAVYYCARWDFLDYWGQGTTVTVS
SASTKGPSVFPLAPSSKSTSGGTAALGCLVKDYFPEPVTVSWNSGALTSGVHTFPAVL
QSSGLYSLSSVVTVPSSSLGTQTYICNVNHKPSNTKVDKKVEPKSCGTDKTHTSPPSP
APPVAGPSVFLFPPKPKDTLMISRTPEVTCVVVDVSHEDPEVKFNWYVDGVEVHNAKT
KPREEQYNSTYRVVSVLTVLHQDWLNGKEYKCKVSNKGLPSSIEKTISKAKGQPREPQ
VYTLPPSRDELTKNQVSLSCAVKGFYPSDIAVEWESNGQPENNYKTTPPVLDSDGSFF
LVSKLTVDKSRWQQGNVFSCSVMHEALHNHYTQKSLSLSPGK

SEQ ID 31:
DVQMTQSPSSLSASVGDRVTITCRSSQSLLHSNGNTYLHWYQQKPGKAPKLLIYTVSN
RFSGVPSRFSGSGSGTDFTLTISSLQPEDFATYYCSQSTHVPYTFGGGTKVEIKRTVA
APSVFIFPPSDEQLKSGTASVVCLLNNFYPREAKVQWKVDNALQSGNSQESVTEQDS
KDSTYSLSSTLTLSKADYEKHKVYACEVTHQGLSSPVTKSFNRGECGTDKTHTSPPSP
APPVAGPSVFLFPPKPKDTLMISRTPEVTCVVVDVSHEDPEVKFNWYVDGVEVHNAKT
KPREEQYNSTYRVVSVLTVLHQDWLNGKEYKCKVSNKGLPSSIEKTISKAKGQPREPQ
VYTLPPSRDELTKNQVSLWCLVKGFYPSDIAVEWESNGQPENNYKTTPPVLDSDGSF
FLYSKLTVDKSRWQQGNVFSCSVMHEALHNHYTQKSLSLSPGK

SEQ ID 32:
HVQLVQSGAEVKKPGSSVKVSCKASGYTFTDFYINWVRQAPGQGLEWIGEIVPSQGE
AKYNDKFKARVTITADKSTSTAYMELSSLRSEDTAVYYCARWDFLDYWGQGTTVTVS
SGTDKTHTSPPSPAPPVAGPSVFLFPPKPKDTLMISRTPEVTCVVVDVSHEDPEVKFN
WYVDGVEVHNAKTKPREEQYNSTYRVVSVLTVLHQDWLNGKEYKCKVSNKGLPSSIE
KTISKAKGQPREPQVYTLPPSRDELTKNQVSLSCAVKGFYPSDIAVEWESNGQPENNY
KTTPPVLDSDGSFFLVSKLTVDKSRWQQGNVFSCSVMHEALHNHYTQKSLSLSPGK

SEQ ID 33:
DVQMTQSPSSLSASVGDRVTITCRSSQSLLHSNGNTYLHWYQQKPGKAPKLLI
YTVSNRFSGVPSRFSGSGSGTDFTLTISSLQPEDFATYYCSQSTHVPYTFGGGTKVEI
KGTDKTHTSPPSPAPPVAGPSVFLFPPKPKDTLMISRTPEVTCVVVDVSHEDPEVKFN
WYVDGVEVHNAKTKPREEQYNSTYRVVSVLTVLHQDWLNGKEYKCKVSNKGLPSSIE
KTISKAKGQPREPQVYTLPPSRDELTKNQVSLWCLVKGFYPSDIAVEWESNGQPENN
YKTTPPVLDSDGSFFLYSKLTVDKSRWQQGNVFSCSVMHEALHNHYTQKSLSLSPGK

SEQ ID 34:
DKTHTCAA

SEQ ID 35:
DKTHTCPPCPAPELLGG

SEQ ID 36:
SASV

Fig. 25 (continued)

SEQ ID 37:
DRVT

SEQ ID 38:
SLQP

SEQ ID 39
GGLV

SEQ ID 40
NAKNSL

SEQ ID 41
LQMN

SEQ ID 42
GTDKTHTSPPCPAPPVAG

SEQ ID 43
GTDKTHTCPPSPAPPVAG

SEQ ID 44
GTDKTHTSPPSPAPPVAG

MONOVALENT ANTI-HUTNFR1 ANTIBODIES, ENCODING NUCLEIC ACIDS THEREOF AND METHODS OF TREATMENT THEREOF

This application is a 371 of International Application Number PCT/EP2017/057997 filed on Apr. 4, 2017, which claims the benefit of European Application Number 16163822.6, filed on Apr. 5, 2016, entitled "MONOVALENT INHIBITOR OF huTNFR1 INTERACTION", the entire disclosures of which are hereby incorporated by reference.

The invention refers to an inhibitor of the TNF-huTNFR1 receptor interaction which monovalently recognizes huTNFR1 with a high affinity.

BACKGROUND

Tumor necrosis factor (TNF) is a pleiotropic cytokine and a central mediator of inflammation. Elevated levels of TNF are associated with various inflammatory diseases including rheumatoid arthritis, psoriasis, and Crohn's disease. Several TNF-neutralizing reagents have been approved for the treatment of these diseases, including soluble TNF receptors (etanercept) as well as anti-TNF antibodies (infliximab, adalimumab, certolizumab pegol, golimumab), and many more are under development. With over 1 million patients treated with TNF antagonists, therapeutic efficacy is well documented. However, global TNF inhibition over a prolonged period of time increases the risk of tuberculosis reactivation, serious infections and even malignancies. Consequently, medical information of all approved anti-TNF medicines includes extensive warnings and precautions.

Two TNF receptors (CD120a, TNFR1 and CD120b, TNFR2) mediate signal transduction upon binding of TNF (Locksley et al., 2001, Cell 104:487-501). Pro-inflammatory responses are mainly mediated by the ubiquitously expressed TNFR1. TNFR1 is activated both by the membrane-bound form of TNF (mTNF) and soluble TNF (sTNF), which is produced from mTNF by proteolytic cleavage. In contrast, TNFR2, expressed in a more restricted manner e.g. by immune cells, endothelial cells and neurons, can only be activated by mTNF. Activation of TNFR2 mainly induces anti-apoptotic signals and can lead to cell proliferation in vitro. Furthermore, TNFR2 appears to play a role in tissue homeostasis and regeneration.

Selective inhibition of TNFR1 signaling has gained increasing attention as alternative to global TNF neutralization, which affects both TNF receptors (Fischer et al. 2015, Antibodies 4:48-70). Recently, a TNF mutein (R1antTNF) selectively neutralizing the activity of TNFR1 has been described (Shibata et al. 2008, Cytokine 2:229-33). This TNF mutein, administered either as unmodified or as PEGylated protein (PEG-R1antTNF), demonstrated therapeutic efficacy in acute murine hepatitis models and a murine collagen-induced arthritis model. The beneficial effect of selectively inhibiting TNFR1 was further supported by results from a dominant-negative TNF mutein (XPro1595), which is capable of forming inactive complexes with sTNF, thus selectively inhibiting the pro-inflammatory action mediated by TNFR1 while preserving the innate immunity to infections (Olleros et al. 2009, J. Infect. Dis. 199:1053-63).

TNFR1-selective inhibition can be also achieved with TNFR1-specific antibodies. For example, a monoclonal murine antibody, H398, and antibody described in U.S. Pat. No. 5,736,138, with selectivity for human TNFR1, showed potent inhibition of TNF-mediated signal transduction and cytotoxicity (Moosmayer et al. 1995, Ther. Immunol. 2:31-40).

A humanized version of H398 is described by WO2008/113515A2. Specifically a humanized antibody was produced as Fab fragment (IZI-06.1) and exhibited in vitro neutralizing activities comparable to that of the Fab fragment of the parental antibody. Importantly, the H398 antibody did not reach complete block of TNF activity, which was interpreted by the conversion from an antagonist into a partial agonist at high concentrations. This is explained by dose-dependent increase in TNFR1 crosslinking, thus potentially forming ligand-independent, functional TNFR1 signaling complexes.

Attempts towards affinity maturation of IZI-06.1 resulted in a mutant (scFvIG11) showing a two-fold increase in antigen binding affinity which also translated into slightly improved inhibition of TNF-mediated cytotoxicity in vitro (Zettlitz K A, thesis 2012, Universität Stuttgart).

Kontermann et al. (Journal Of Immunotherapy 2008, 31(3):225-234) describe a monovalent antibody fragment of IZI-06.1 as a TNFR1-selective TNF antagonist.

Antibodies to TNFR1 were found to have an agonistic potential by inducing a response mimicking the ligand. This response suggests that signal transduction is initiated by aggregation of receptors due to binding of the multivalent TNF trimers. In particular, divalent anti-TNFR1 antibodies were known to bear the risk of TNFR activation due to receptor crosslinking, causing themselves pro-inflammatory reactions, including cytotoxicity and apoptosis, which would be contraproductive in treating TNF-mediated disease conditions.

WO02012035141A1 describes an anti-huTNFR1 antibody of the IgG1 type called ATROSAB, which has a modified Fc region deficient in mediating effector function, which was found to limit the agonistic potential of the antibody.

Richter et al. (2013, PLoS One 8:e72156) describe the inhibition of TNFR1 to interact with its natural ligands TNF and lymphotoxin alpha (LTα) by ATROSAB as measured by the release of IL-6 and IL-8 from HeLa and HT1080 cells, respectively, induced by TNF or LTα.

SUMMARY OF THE INVENTION

It was the objective to provide an improved anti-huTNFR1 agent with improved TNFR1-inhibiting characteristics while avoiding any side effects caused by intrinsic TNF mimetic agonistic activity.

The object is solved by the subject matter as claimed.

According to the invention there is provided an inhibitor of the TNF-huTNFR1 receptor interaction which is a human or humanized antibody construct that monovalently recognizes huTNFR1 through an antigen-binding moiety.

Specifically, the antigen-binding moiety comprises
a heavy chain variable (VH) domain that comprises the CDR sequences CDRH1, CDRH2, and CDRH2, and
a light chain variable (VL) domain that comprises the CDR sequences CDRL1, CDRL2, and CDRL2, wherein
A
a) the CDRH1 sequence is identified as SEQ ID 1;
b) the CDRH2 sequence is identified as SEQ ID 10;
c) the CDRH3 sequence is identified as SEQ ID 3;
d) the CDRL1 sequence is identified as SEQ ID 4;

e) the CDRL2 sequence is identified as SEQ ID 5; and f) the CDRL3 sequence is identified as SEQ ID 11;

or

B a) the CDRH1 sequence is a functionally active CDR variant of SEQ ID 1; and/or b) the CDRH2 sequence is a functionally active CDR variant of SEQ ID 10; and/or c) the CDRH3 sequence is a functionally active CDR variant of SEQ ID 3; and/or d) the CDRL1 sequence is a functionally active CDR variant of SEQ ID 4; and/or e) the CDRL2 sequence is a functionally active CDR variant of SEQ ID 5; and/or f) the CDRL3 sequence is a functionally active CDR variant of SEQ ID 11;

or wherein the functionally active CDR variant comprises not more than 1 or 2 point mutations in the respective CDR sequence at any position, except at position 5 in CDRH2 and at position 3 in CDRL3.

The functionally active CDR variants of embodiment B. determine functionally active variants of the inhibitor of embodiment A, wherein the functionally active CDR variant of the CDRH2 sequence specifically comprises the amino acid sequence at position 5 which is any of G or S; and the functionally active CDR variant of the CDRL3 sequence specifically comprises the amino acid sequence at position 3 which is any of G or S. The functionally active CDR variant specifically determines the high affinity of binding the huTNFR1, such as further described herein. Specifically, the functionally active variant is an affinity matured variant of the inhibitor of embodiment A, in particular wherein 1, 2, 3, 4, 5, or 6 of the CDR sequences are functionally active CDR variants.

Specifically, the inhibitor described herein has surprisingly turned out to exhibit improved binding properties as compared to the scFvIG11 that was previously engineered as an improved version of IZI-06.1.

Specifically, the antigen-binding moiety is binding huTNFR1 with a $K_D$ of less than $5 \times 10^{-9}$ M and a $k_{off}$ of less than $10^{-3}$ s$^{-1}$. The affinity of binding and binding characteristics (association and dissociation) is specifically determined in a standard test for determining monovalent binding, substantially excluding the avidity effects of divalent binding. A standard test is based on the measurement by quartz crystal microbalance (QCM) at physiological temperature (about 37° C., or at 37° C.+/−1° C.). Such affinity measurement is particularly performed in a Fab format. Thus, if the antibody construct is any other than a Fab molecule, the antigen-binding site is particularly introduced into a respective Fab molecule for affinity measurement by QCM at 37° C. This ensures the comparability of results of affinity measurement of monovalent binders irrespective of avidity effects that could interfere with the affinity measurement. The specifically preferred QCM is performed at moderate receptor density. Specifically, the affinity of the antibody construct binding to the huTNFR1 is determined for the Fab format by QCM at 37° C. and moderate receptor density within the range of 50-100 Hz, e.g. at about 50 Hz, or at 50 Hz+/−10 Hz, or at 50 Hz+/−5 Hz. A standard test for determining the affinity of binding by QCM is described in the examples section below.

Specifically, $K_D$ is less than $4 \times 10^{-9}$ M, or less than $3 \times 10^{-9}$ M, or less than $2 \times 10^{-9}$ M, or less than $10^{-9}$ M, or even less than $10^{-10}$ M Specifically, the $k_{off}$ is less than $10^{-3}$, or less than $5 \times 10^{-4}$ s$^{-1}$, or less than $10^{-4}$ s$^{-1}$ or less than $10^5$ s$^{-1}$.

Specifically, the antigen-binding moiety is recognizing the huTNFR1 with a $k_{on}$ of at least $10^5$ M$^{-1}$s$^{-1}$.

According to a specific aspect, the inhibitor directly inhibits the TNF-huTNFR1 receptor interaction as determined in a cell-based assay, preferably by an assay for inhibition of TNFR1-mediated cell death in Kym-1 cells, or by an assay for inhibition of IL-6 or IL-8 release from HeLa cells or HT1080 cells, respectively. Specifically, in an assay for inhibition of TNFR1-mediated cell death in Kym-1 cells the IC$_{50}$ value is less than $5.0 \times 10^{-9}$ M. Specifically, in an assay for inhibition of IL-6 release from HeLa cells the IC$_{50}$ value is less than $4.0 \times 10^{-8}$ M, or in an assay for inhibition of IL-8 release from HT1080 cells the IC$_{50}$ value is less than $2.0 \times 10^{-8}$ M.

Due to monovalent interaction, a TNF-mimetic agonistic potential of the antibody construct has been specifically eliminated, while the increased affinity of binding to TNFR1, specifically the low off rate, provides superior inhibition of TNFR1-dependent TNF responses.

According to a further specific aspect, the inhibitor directly inhibits the huTNFR1-receptor interaction with lymphotoxin alpha as determined in a cell-based assay, preferably by an assay for inhibition of TNFR1-mediated cell death in Kym-1 cells, or by an assay for inhibition of IL-6 or IL-8 release from HeLa cells and/or HT1080 cells.

Specifically, the antigen-binding moiety comprises or consists of one or more Fv domains which form the monovalent binding site. According to a specific aspect, the Fv domains are a VH and a VL domain, both in association with each other through interaction of the beta-sheet structure of the domains.

According to one aspect, the antigen-binding moiety is specifically recognizing an epitope comprising the membrane-distal CRD1 and subdomain A1 of CRD2 of huTNFR1.

A specific binding epitope is represented by amino acid 1 to 115 in the N-terminal region of huTNFR1.

According to a specific embodiment, the antibody construct is binding specifically to an epitope which is the same epitope or overlapping with the epitope as recognized by the H398 antibody, as further described herein. Specifically, the antibody construct interferes with the H398 antibody binding to its epitope, such that it is competitively binding to the huTNFR1.

Specifically the antibody construct comprises at least the VH domain and optionally the Fv domains (as VH associated with or bound to VL) of an affinity matured, humanized H398 antibody. Specifically, the H398 antibody and humanized ATROSAB antibody (as further described herein) is characterized by CDR sequences which comprise or consist of the following:

SEQ ID 1: H398 CDRH1
SEQ ID 2: H398 CDRH2
SEQ ID 3: H398 CDRH3
SEQ ID 4: H398 CDRL1
SEQ ID 5: H398 CDRL2
SEQ ID 6: H398 CDRL3

Specifically, the antibody construct comprises a VH and a VL domain, wherein at least one of the VH and VL domains is an affinity matured functional variant of a parent domain comprising at least one point mutation in any of the complementary determining region (CDR) sequences, wherein a) the parent VH domain is characterized by the CDR sequences: SEQ ID 1 (CDRH1), SEQ ID 2 (CDRH2), and SEQ ID 3 (CDRH3); and b) the parent VL domain is characterized by the CDR sequences: SEQ ID 4 (CDRL1), SEQ ID 5 (CDRL2), and SEQ ID 6 (CDRL3);

which CDR sequences are according to the Kabat numbering scheme.

Specifically, the at least one point mutation is in any of SEQ ID 2 (CDRH2) and/or SEQ ID 6 (CDRL3), preferably wherein the CDRH2 sequence is SEQ ID 7, and the CDRL3 sequence is SEQ ID 8.

Specifically, 1 or 2 point mutations may be introduced in any of the CDR sequences to produce functionally active CDR variants. Specifically, the functionally active CDR variants have at least 60%, or at least 70%, or at least 80% sequence identity as compared to any of the CDR sequences of the parent domains, preferably at least 85%, or at least 90%, or only 1 point mutation per CDR sequence, preferably wherein the CDR sequence is either the CDRH2 or the CDRL3 sequence.

Specifically, the antibody construct comprises affinity-matured sequences of a humanized antibody called ATROSAB, which comprises VH and VL sequences for affinity maturation purposes. ATROSAB is specifically characterized by the following VH and VL sequences:

```
SEQ ID 22:
ATROSAB VH

SEQ ID 23:
ATROSAB VL
```

Specifically, the antigen-binding moiety is

A selected from the group consisting of group members i) to ii), wherein i)

is a antigen-binding moiety which comprises a) a CDRH1 sequence identified by SEQ ID 1;
b) a CDRH2 sequence identified by SEQ ID 10, wherein X at position 5 is S;
c) a CDRH3 sequence identified by SEQ ID 3;
d) a CDRL1 sequence identified by SEQ ID 4;
e) a CDRL2 sequence identified by SEQ ID 5; and
f) a CDRL3 sequence identified by SEQ ID 11, wherein X at position 3 is G;

and ii)

is a antigen-binding moiety which comprises a) a CDRH1 sequence identified by SEQ ID 1;
b) a CDRH2 sequence identified by SEQ ID 10, wherein X at position 5 is S;
c) a CDRH3 sequence identified by SEQ ID 3;
d) a CDRL1 sequence identified by SEQ ID 4;
e) a CDRL2 sequence identified by SEQ ID 5; and
f) a CDRL3 sequence identified by SEQ ID 11, wherein X at position 3 is S;

or

B an antigen-binding moiety which is a functionally active variant of a parent antigen-binding moiety that is any of the group members of A.

Specifically, the functionally active variant comprises a) at least one functionally active CDR variant of any of the CDR sequences of the parent antibody, which comprises not more than 1 or 2 point mutations in the respective CDR sequence at any position, except at position 5 in CDRH2 and at position 3 in CDRL3; and/or b) at least one point mutation in the framework region of any of the VH or VL sequences.

The functionally active CDR variants specifically are characterized by the CDRH2 sequence, wherein the amino acid sequence at position 5 is any of G or S; and the CDRL3 sequence, wherein the amino acid sequence at position 3 is any of G or S. The functionally active CDR variant specifically is characterized by the high affinity of binding the huTNFR1, such as further described herein.

Specifically, one or more point mutations may be introduced in any of the FR sequences to produce functionally active FR variants, in particular human or humanized FR sequences.

Specifically, the functionally active FR1 variants of any of the VH or the VL sequences, include one or more, e.g. several point mutations, e.g. up to 2, 3, 4, 5, 6, 7, 8, 9, 10, 11, 12, 13, 14, or 15 point mutations to obtain a variant sequence with at least 40%, or at least 45% sequence identity, or at least 50% sequence identity, or at least 60% sequence identity, or at least 70% sequence identity, or at least 80% sequence identity, or at least 90% sequence identity as compared to the parent FR1 sequence.

Specifically, the functionally active FR2 variants of any of the VH or the VL sequences, include one or more, e.g. several point mutations, e.g. up to 2, 3, 4, or 5 point mutations to obtain a variant sequence with at least 70%, or at least 80% sequence identity, or at least 90% sequence identity as compared to the parent FR2 sequence.

Specifically, the functionally active FR3 variants of any of the VH or the VL sequences, include one or more, e.g. several point mutations, e.g. up to 2, 3, 4, 5, 6, 7, 8, 9, 10, 11, 12, 13, 14, or 15 point mutations to obtain a variant sequence with at least 50%, or at least 60% sequence identity, or at least 70% sequence identity, or at least 80% sequence identity, or at least 90% sequence identity as compared to the parent FR3 sequence.

Specifically, the functionally active FR4 variants of any of the VH or the VL sequences, include one or more, e.g. several point mutations, e.g. up to 2, 3, 4, or 5 point mutations to obtain a variant sequence with at least 70%, or at least 80% sequence identity, or at least 90% sequence identity as compared to the parent FR4 sequence.

According to a specific embodiment, the antibody construct is selected from the group consisting of Fab molecules, scFv molecules, single variable domains, disulfide-stabilized Fv (dsFv), half-IgG1 antibodies, and Fv domains, or a functionally active derivative of any of the foregoing, preferably wherein the antibody construct is coupled to a hydrophilic polymer, such as PEG, and/or fused to a polypeptide, such as human (or mouse) serum albumin, transferrin, albumin-binding domains or peptides, Ig-binding domains or peptides, PEG-mimetic polypeptide extensions, an antibody Fc fragment, an antibody Fc fragment carrying mutations to allow for preferred heterodimerization (over homodimerization), or a functional variant of any of the foregoing polypeptides.

Specifically, the antibody construct is any of a Fab, scFv, dsFv, or Fv domains, which is fused to an antibody Fc fragment, wherein the Fc consists of a heterodimer of CH2 and CH3 domains, wherein the CH2 and/or CH3 domains carry one or more point mutations which allow preferential heterodimerization over homodimerization. Specifically, one or both of the CH3 domains in the Fc are modified to change the amino acid structure, such as to obtain a Fc containing the heterodimer of the CH3/CH3 domains.

Specifically, the antibody construct comprises Fv domains fused to an antibody Fc region or fragment, with or without further antibody domains, yet, maintaining the monovalent binding structure of the antibody construct. A specific example refers to a Fab moiety or Fv moiety fused to Fc or modified Fc.

Specific embodiments comprise a human IgG1 Fc wherein the CH2-CH3 domains form a heterodimer through one or more "knobs-into-holes" mutations, e.g.

"knobs" mutations modifying the surface of CH3 beta-sheets, present on one CH3 domain monomer, which is T366W; and "holes" mutations modifying the surface of CH3 beta-sheets, present on the other CH3 domain monomer, which are selected from the group consisting of T366S, L368A, Y407V.

Specifically, the antibody construct comprises an Fc region which comprises one or more mutations to downmodulate the effector function. According to a specific aspect, the Fc region is glycoengineered to downmodulate the effector function.

Specifically, the antibody construct comprises a (human IgG1) Fc region which is characterized by FcγR silenced CH2 and CH3 domains, e.g., through one or more mutations selected from the group consisting of E233P, L234V, L235A, AG236, A327G, A330S and P331S, S228P, L234A, L235A, H268Q, A330S, P331S, V234A, G237A, P238S, H268A, V309L.

According to a preferred embodiment, the antibody construct comprises an IgG1 Fc region which is mutated to downmodulate the effector function. Preferably the Fc region comprises a heavy chain with at least one mutation selected from the group consisting of E233P, L234V, L235A, AG236, A327G, A330S and P331S (Kabat EU index numbering). Preferably at least two of said mutations, more preferably at least three, four, five or all of the six mutations are engineered into the human IgG1 Fc sequence. The human IgG1 Fc sequence is specifically included in the amino acid sequence identified as SEQ ID 24. SEQ ID 24 identifies the sequence of human IgG1 Fc and the hinge region (wild-type IgG1 hinge region (SEQ ID 35), plus CH2-CH3 domains).

Specifically, the antibody construct comprises a humanized or human framework region.

Specifically, the antibody construct is PEGylated, HESylated, or PSAylated.

Specifically, the antibody construct is pegylated with a PEG of a molecular weight ranging between 5.000 to 150.000 g/mol. Exemplary antibody constructs, such as Fabs, are pegylated with PEG 40.000.

Specifically, the antibody construct is a half antibody IgG1, characterized by only one Fab part, a hinge region and one Fc part, wherein the hinge region and/or the Fc part (particularly the human IgG1 Fc) comprises one or more mutations to avoid heavy chain dimerization (Gu et al. (2015) PLoS One 10(1):e0116419), e.g. selected from the group consisting of mutations in the hinge region (SEQ ID 35): C226S, C229S (EU numbering), and mutations in the Fc part: P395A, F405R, Y407R, K409D (EU numbering).

Specifically, the antibody construct is a Fv-Fc fusion protein, wherein the VH is fused to a first CH2-CH3 domain chain via a first hinge region, and the VL is fused to a second CH2-CH3 domain chain via a second hinge region. Preferably the first and second CH2-CH3 domain chains differ from each other in one or more point mutations, such as to allow preferential heterodimerization between the first and second CH2-CH3 domain chains, thereby obtaining a Fv-Fc preparation which is characterized by the Fc heterodimer, e.g. through "knobs-into holes" mutations as indicated above. Further, the first and second hinge regions may be modified as follows:

GTDKTHTSPPCPAPPVAG, (SEQ ID 42)

GTDKTHTCPPSPAPPVAG, (SEQ ID 43)
or

GTDKTHTSPPSPAPPVAG. (SEQ ID 44)

Specifically, the antibody construct is a disulfide-stabilized Fv (dsFv), which is characterized by one or more additional (artificial) interdomain disulfide bonds. Such disulphide bonds are obtained by introducing one or more additionally cysteine residues into either of the VH and VL domains at suitable positions which may be used as a bridge pier of disulphide bonds bridging the VH and VL domains, which disulphide bonds are obtained upon reducing the cysteines. According to specific examples, a disulphide bond may be introduced into the Fv at any of the following positions in VH and corresponding positions in VL: 44C in VH and 100C in VL, 108C in VH and 55C in VL, 106C in VH and 56C in VL, or 101C in VH and 46C in VL.

According to a specific aspect, the antibody construct comprises Fv domains with increased affinity to bind the huTNFR1 as compared to parent Fv domains wherein the parent Fv domains are characterized by a parent VH domain identified as SEQ ID 12 and a parent VL domain identified as SEQ ID 16.

Specifically, at least one of the VH and VL domains is an affinity-matured functional variant of the parent domain, comprising at least one point mutation in any of the CDR or framework (FR) sequences.

Specifically,
a) the VH domain comprises or consists of a sequence selected from the group consisting of SEQ ID 13-15, or a functionally active variant of any of SEQ ID 13-15; and/or;
b) the VL domain comprises or consists of a sequence selected from the group consisting of SEQ ID 17-19, or a functionally active variant of any of SEQ ID 17-19; or
c) wherein the functionally active variant of a) or b) comprises at least one point mutation in any of the CDR or FR sequences. Specifically, the functionally active variant of a) or b) is characterized by
a) 1 or 2 point mutations in any of the CDR sequences at any position except at position 5 in CDRH2 and at position 3 in CDRL3; and/or
b) at least one point mutation in the framework region of any of the VH or VL sequences.

Specifically, the inhibitor comprises a combination of a VH and a VL domain, which is

A selected from the group consisting of group members i) to ix), wherein
i)
VH comprises or consists of SEQ ID 13, and
VL comprises or consists of SEQ ID 17;
ii)
VH comprises or consists of SEQ ID 14, and
VL comprises or consists of SEQ ID 18;
iii)
VH comprises or consists of SEQ ID 15, and
VL comprises or consists of SEQ ID 19;

iv)
VH comprises or consists of SEQ ID 14, and
VL comprises or consists of SEQ ID 19;
v)
VH comprises or consists of SEQ ID 15, and
VL comprises or consists of SEQ ID 18;
vi)
VH comprises or consists of SEQ ID 13, and
VL comprises or consists of SEQ ID 18;
vii)
VH comprises or consists of SEQ ID 14, and
VL comprises or consists of SEQ ID 17;
viii)
VH comprises or consists of SEQ ID 13, and
VL comprises or consists of SEQ ID 19;
and
ix)
VH comprises or consists of SEQ ID 15, and
VL comprises or consists of SEQ ID 17;
or
B
a combination of a VH and VL domain of any of the group members i)-ix) of A, wherein the VH domain is a functionally active variant of any of SEQ ID 13-15, and/or the VL domain is a functionally active variant of any of SEQ ID 17-19, which functionally active variant is characterized by a) 1 or 2 point mutations in any of the CDR sequences at any position except at position 5 in CDRH2 and position 3 in CDRL3; and/or b) at least one point mutation in the framework region of any of the VH or VL sequences.

The functionally active variant may be a functionally active CDR variant with at least one point mutation in any of the CDR sequences, and/or a functionally active variant with at least one point mutation in any of the FR sequences. Yet, the functionally active CDR variants specifically are characterized by the CDRH2 sequence, wherein the amino acid sequence at position 5 is any of G or S; and the CDRL3 sequence, wherein the amino acid sequence at position 3 is any of G or S. The functionally active CDR variant specifically is characterized by the high affinity of binding the huTNFR1, such as further described herein.

According to a specific aspect, the antibody construct has an increased thermostability as compared to a parent antibody construct wherein the antibody construct comprises Fv domains which are functional variants of parent Fv domains with at least one point mutation in the framework region of any of the VH or VL sequences, preferably wherein the VH domain sequence is a variation of the (parent) IZI06.1 VH sequence (SEQ ID 20) and comprises any of the amino acids (Kabat numbering):

a) in FR1 at position 1: Q or H;
b) in CDRH2
i) at position 3: Y or V;
ii) at position 5: Y, T, or S;
iii) at position 6: S or Q;
iv) at position 8: H or E;
v) at position 10: Y or K;
vi) at position 13: E or D.

A further preferred variation concerns the VL sequence (SEQ ID 21) and comprises the S91G point mutation in the CDRL3 (position 3).

Specifically, the thermostability of preferred variants of the antibody construct or the inhibitor is at least 60° C., or at least 61° C., or at least 62° C. or at least 63° C., or at least 64° C., or at least 65° C., as determined by dynamic light scattering.

The invention further provides for a pharmaceutical preparation comprising the inhibitor described herein and a pharmaceutically acceptable carrier.

Because of the antagonistic properties of the inhibitor and the antibody construct, the pharmaceutical preparation may comprise high concentrations of the inhibitor, while avoiding the side effects resulting from agonistic activity.

In the absence of the full-length immunoglobulin structure, the inhibitor specifically has reduced immunogenicity and may be repeatedly used without formation of inhibitors, such as anti-drug antibodies (ADA).

It has surprisingly turned out that the inhibitor can be used for treating patients developing ADA, e.g. which have developed antibodies against immunoglobulin or antibody immuntherapeutics. In the prior art, the presence of such ADA would particularly exclude further immunotherapies with antibodies directed against TNFR1, because ADA have the potential to cross-link the antibodies upon binding the TNFR1 on the cell surface, thereby agonising the TNFR1 signaling. However, the inhibitor described herein surprisingly does not agonise the TNFR1 signaling even in the presence of ADA.

Specifically, the pharmaceutical preparation may be administered to subjects who have developed ADA, e.g. ADA against anti-huTNFR1 antibodies or any IgG structures.

Specifically, the preparation is formulated for parenteral use, preferably by intravenous or subcutaneous administration.

The invention further provides for a method of producing the huTNFR1 inhibitor described herein employing a recombinant mammalian expression system to express the antibody construct.

Specifically, production cell lines are used which are eukaryotic or mammalian cell lines, including cell lines of different origin e.g. human, such as HEK or PER.C6; hamster, such as CHO or BHK; monkey, such as COS-1 or COS-7; mouse, such as C127, SP2/0 or NS0; or yeast, such as *Saccharomyces cerevisiae* or *Pichia pastoris*.

Specifically, a CHO production cell line is employed.

Alternative prokaryotic production cell lines include e.g. *Escherichia coli*.

The invention further provides for the inhibitor for medical use, specifically, for use in treating a human subject in need of an anti-TNF therapy.

Thus, the invention further provides for a method of treating a human subject in need of an anti-TNF therapy, by administering an effective amount of the inhibitor described herein.

Specifically, the TNFR1-specific inhibitor is used as a TNF antagonist incapable of crosslinking TNFR1, as an alternative to treatment with an anti-TNF therapeutic.

Such TNF antagonists, also considered as biological TNF antagonists, are typically provided for therapeutic use where the biological relevance of TNFR1-mediated TNF function in the pathogenesis of chronic noninfectious inflammation of joints, skin and gut has been proven.

Drug-specific antibodies (ADA) induced by therapeutic antibodies or naturally occurring antibodies may also lead to undesired agonistic activity, because of the potential to cross-link drug-bound TNFR1 and activate the TNFR1 signaling. Thus, the preferred antibody construct is devoid of a homodimerizing Fc region or devoid of an Fc region, such as a Fab or scFv format, and the respective pharmaceutical composition is less likely to result in cross-linking and increased stimulatory activity to inflammatory processes.

According to a specific embodiment, the inhibitor is repeatedly administered to the subject.

It is preferred that the inhibitor or antibody described herein has a low immunogenic potential and can be used for treating a subject without inducing undesired immune response to the antibody.

To this end, the preferred antibody construct consists of humanized or human antibody sequences, and is e.g. devoid of a homodimerizing Fc region or devoid of an Fc region, such as a Fab or scFv format. The respective pharmaceutical composition is less likely to result in a loss of tolerance (e.g., upon repeated administration), thereby improving both the safety and efficacy profile of the therapeutic.

Specific embodiments refer to the treatment of subjects suffering from an immune response or a high level of antibodies against therapeutic antibodies, in particular antibodies comprising an Fc region which have been used for previous therapies. Such patients are preferably treated with an antibody construct described herein devoid of the homodimerizing Fc region or devoid of the Fc region.

Specifically, the inhibitor described herein is provided for medical use in treating a human subject suffering from a disease where anti-TNF therapies or non-biologic disease-modifying anti-rheumatic drugs (DMARD) are indicated. Specifically, the medical use encompasses a first line treatment with an effective amount of the inhibitor, where anti-TNF therapies or non-biologic DMARD are indicated, or as second line treatment where anti-TNF or non-biologic DMARD therapeutics failed.

Specifically, the subject is suffering from a) acute or chronic inflammation of joints, skin and gut, (infectious or noninfectious); and/or b) autoimmune diseases, rheumatoid arthritis, psoriasis, psoriatic arthritis, juvenile arthritis, ankylosing spondylitis, Crohn's disease (Morbus Crohn), multiple sclerosis, congestive heart failure, metabolic disease, cytokine release syndrome, septic shock, acute and chronic neurodegenerative disease, stroke, Alzheimer and Parkinson disease, colitis ulcerosa, pancreatitis, COPD, acute fulminant viral or bacterial infections, metabolic diseases, chronic neurodegenerative diseases, genetically inherited diseases with TNF/TNFR1 as the causative pathologic mediator, periodic fever syndrome, Cherubism, and cancer.

In particular, inflammatory disease conditions are treated which are associated with any of the diseases listed above. Specifically, the subject is treated suffering from any of the diseases of a) and any of the diseases of b) above.

According to a specific aspect, the invention further provides for an isolated nucleic acid encoding the inhibitor described herein. Specifically, the nucleic acid is operably linked to a non-coding or coding nucleic acid sequence not naturally-occurring with the nucleic acid, such as including heterologous promoter or regulatory sequences. Specifically, the nucleic acid is an artificial nucleic acid.

The invention further provides for a vector comprising an expression cassette or a plasmid, each comprising a coding sequence to express a proteinaceous construct comprising or consisting of a polypeptide or protein, or a protein derivative, comprising the antigen-binding site or the a VH and/or VL of the inhibitor antibody as described herein.

The invention further provides for a host cell comprising the expression cassette, expression vector or plasmid as described herein.

The invention further provides for a method of producing the inhibitor as described herein, wherein the host cell is cultivated or maintained under conditions to produce said antibody.

Specifically preferred is a host cell and a production method employing such host cell, which host cell comprises
- an expression vector, which incorporates a coding sequence to express the antibody light chain; and
- an expression vector, which incorporates a coding sequence to express the antibody heavy chain.

According to a specific aspect, the invention further provides for a recombinant host cell comprising the nucleic acid or the expression vector described herein.

FIGURES

FIG. 1. Binding of H398 and ATROSAB to human TNFR1-Fc. a) Equilibrium binding of ATROSAB and H398 was analyzed by standard ELISA (n=3, mean+SD). QCM binding kinetics of ATROSAB (b) and H398 (c) tested under conditions of high receptor density (195 Hz). Applied were triplicates of five concentrations between 3.9 nM and 62.5 nM.

FIG. 2. Inhibition of TNF action by ATROSAB and H398. Inhibition of IL-8 secretion from HT1080 cells with increasing concentrations of ATROSAB and H398 induced by 0.1 nM TNF (a) and LTα (b). Data from n=3 experiments are shown as percent of maximal IL release, triggered by TNF or LTα alone.

Figure 3:
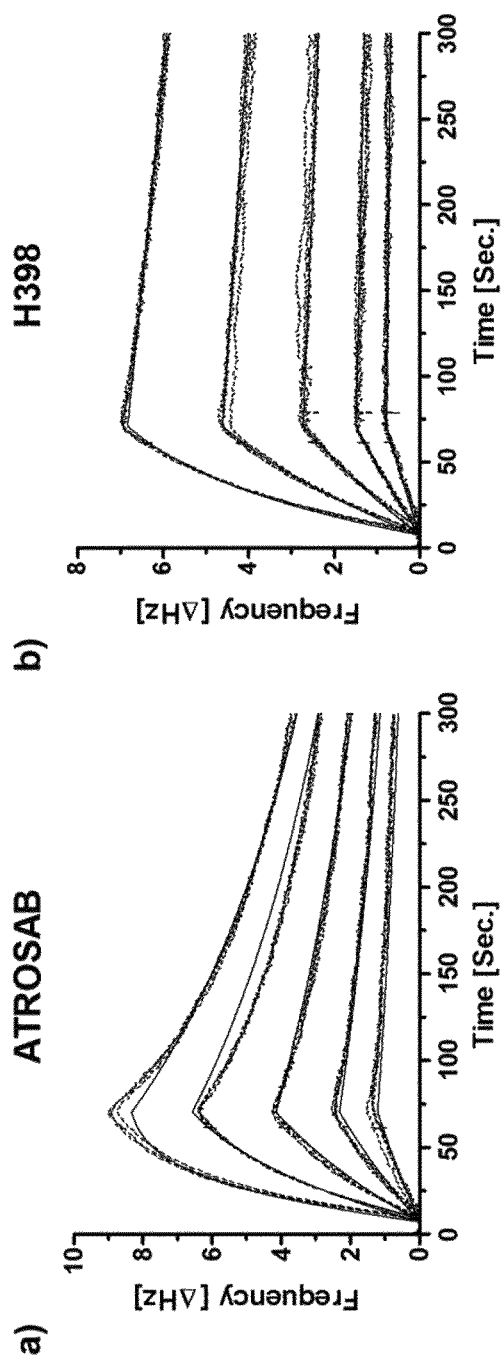

FIG. 3. Binding kinetics at low receptor density. Determination of the affinity of Atrosab (a) and H398 (b) for human TNFR1-Fc by QCM at a receptor density of 48 Hz.

FIG. 4. Sequence alignment of scFvIZI06.1 (VH: SEQ ID 20, VL: SEQ ID 21) with parent VH and VL sequences and affinity matured variants. a) aligned VH sequences of ATROSAB (scFvIZI06.1), scFvIG11, scFvT12B and scFv-FRK13.7. b) Alignment of VL sequences. Residues are numbered according to the Kabat numbering scheme and dots represent identical amino acids compared with scFvIZI06.1. Sequences of 4 amino acids or more are indicated as follows. Sequences in FR1 of scFvFRK13.7: SASV (SEQ ID 36); DRVT (SEQ ID 37). Sequence in FR3 of scFvFRK13.7: SLQP (SEQ ID 38).

Figure 5:
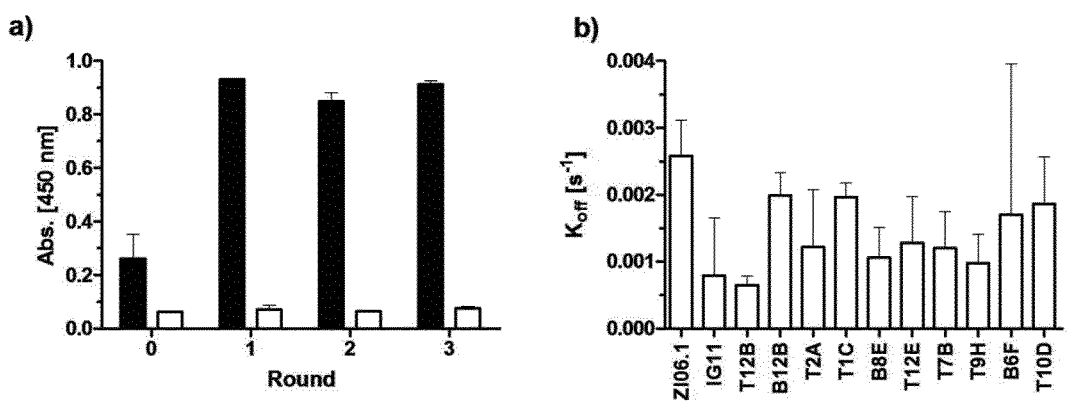

FIG. 5. Selection of Library EP03. The pool of amplified phages was analyzed for total binding to human TNFR1-Fc in ELISA after each round of selection (a). Selected candidates were expressed as soluble scFv formats and tested for binding to human TNFR1-Fc in QCM measurements (b). Shown are mean and SD of a single experiment with duplicates, scFvIZI06.1 and scFvIG11 served as controls in b.

Figure 6:
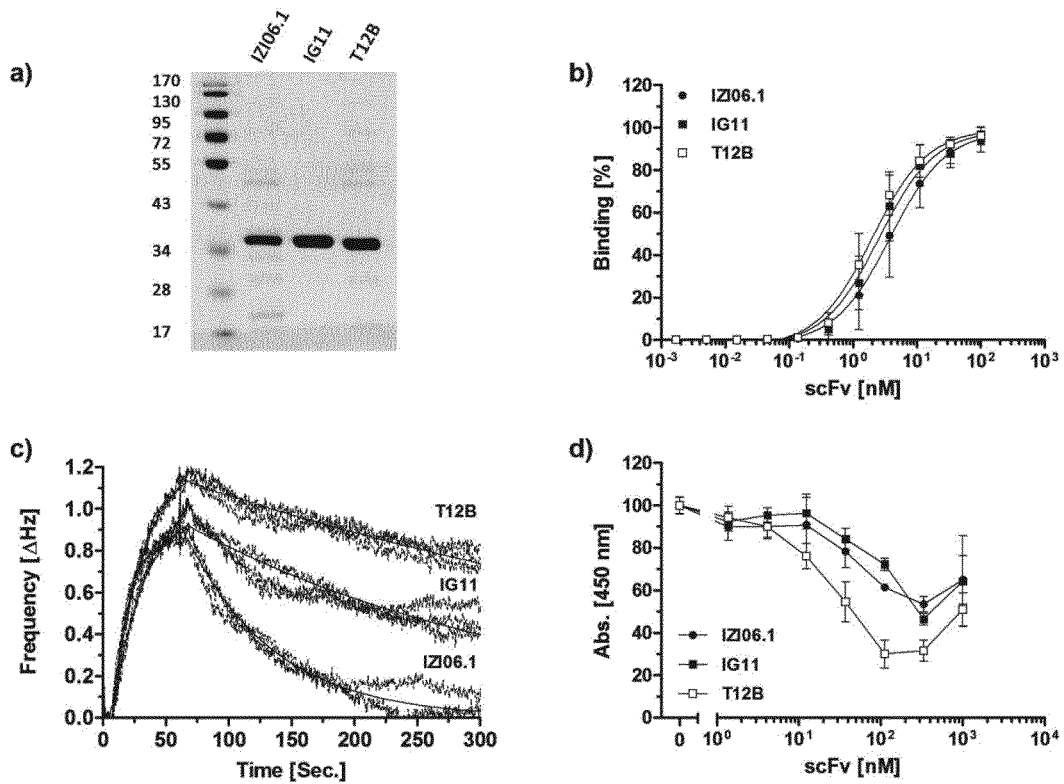

FIG. 6. Expression and characterization of scFvT12B. A) Coomassie stained SDS-PAGE (12%) of scFvT12B and the control antibodies scFvIZI06.1 and scFvIG11. Binding to human TNFR-Fc was tested in ELISA (b) and QCM analysis (c), where measurement (dashed line) and fit (solid line) are displayed. Inhibition of TNF (0.1 nM) induced release of IL-8 was demonstrated in d). B) and d) show mean and SD of two (d) or three (b) individual experiments performed in duplicates.

FIG. 7. Alignment of scFvIZI6.1 (VH: SEQ ID 20, VL: SEQ ID 21) with the humanized sequences. The humanized sequences of VH (a) and VL (b) were aligned to the sequence of the single chain variable fragment of ATROSAB. Identical residues are represented by dots. Sequences of 4 amino acids or more are indicated as follows. Sequence in VH (a) FR1 of FRK13.1 and FRK13.2: GGLV (SEQ ID 39). Sequences in VH (a) FR3 of FRK13.1 and FRK13.2: NAKNSL (SEQ ID 40), LQMN (SEQ ID 41). Sequences in VL (b) FR1 of FRK13.1 and FRK13.2: SASV (SEQ ID 36);

DRVT (SEQ ID 37). Sequence in VL (b) FR3 of FRK13.1 and FRK13.2: SLQP (SEQ ID 38).

Figure 8:
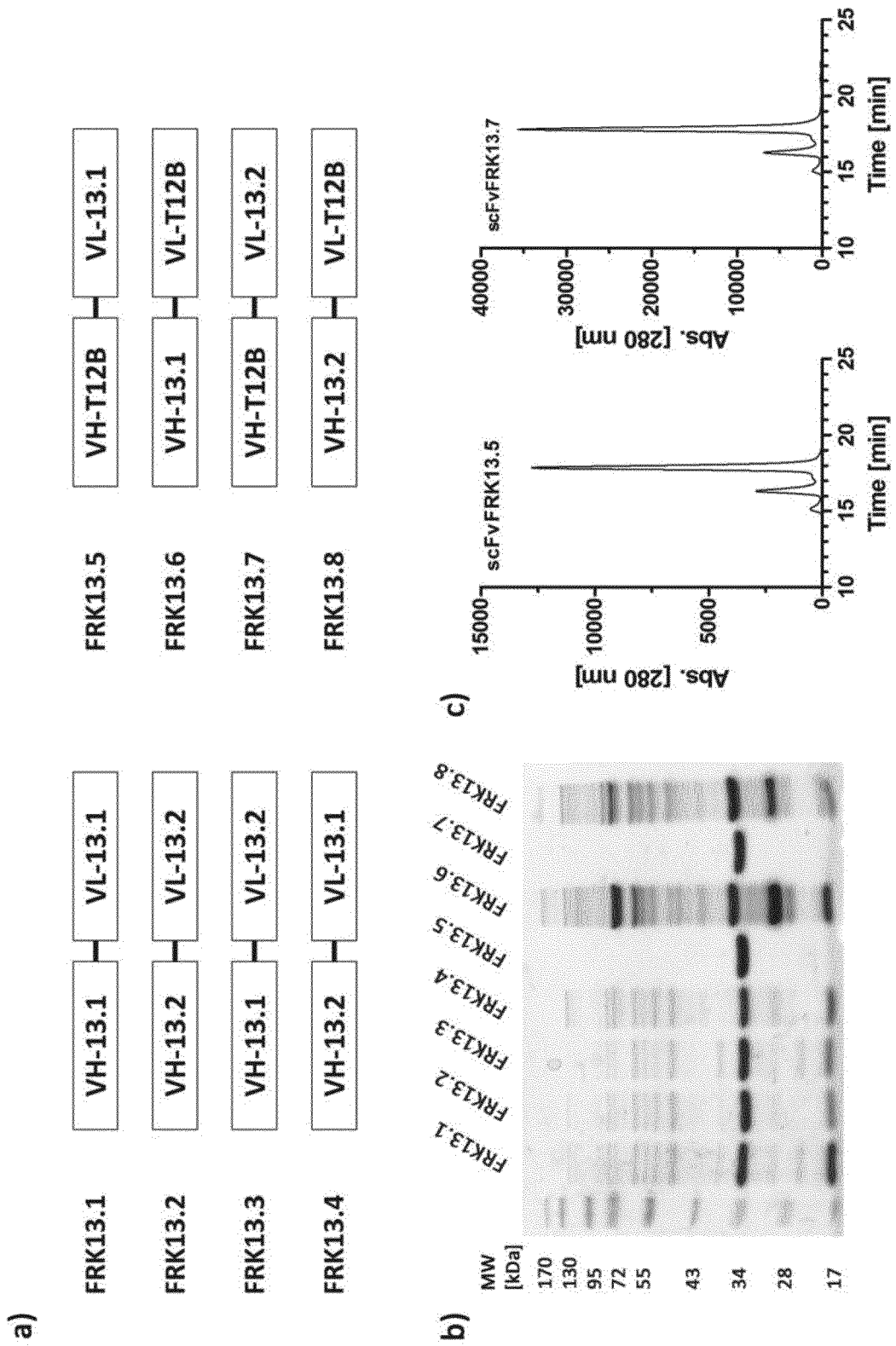

FIG. 8. Production of humanized scFv antibodies. A) genotype of humanized scFv variants combined with scFvT12B. Purified scFv fragments were analyzed by SDS-PAGE (b, 12%, Coomassie-stained) and subsequently by SEC (c, Yarra SEC-2000 column, flow rate 0.5 ml/min) in the case of proper expression.

Figure 9:
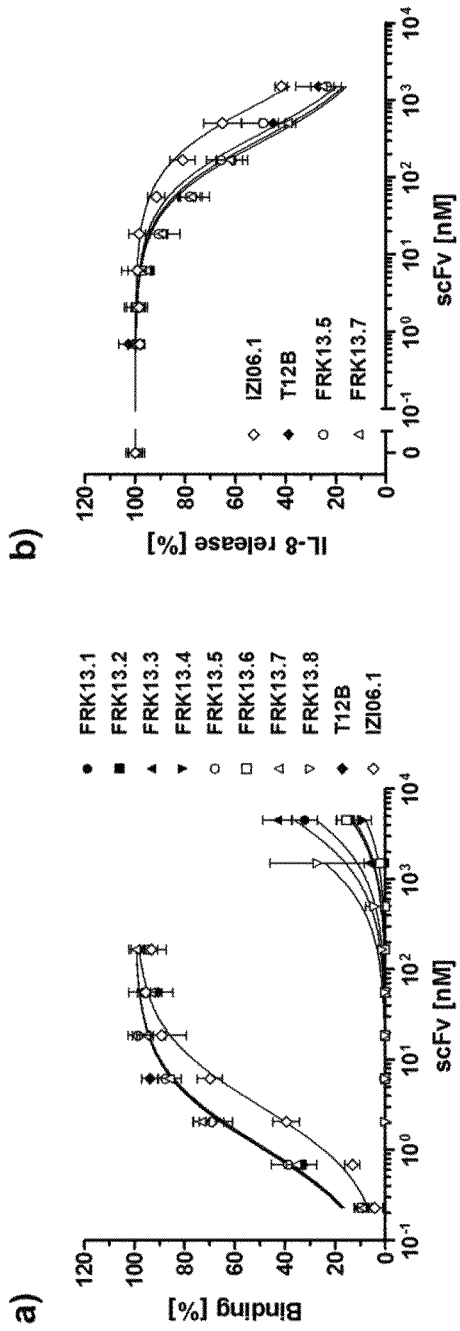

FIG. 9. Binding to and blockade of human TNFR1. Humanized scFv antibodies were tested by ELISA for binding to human TNFR1-Fc (a) and the inhibition of TNF (0.1 nM) induced IL-8 release from HT1080 cells (b, performed only for strongly binding scFvs). scFvIZI06.1 and scFvT12B served as controls (displayed are mean and SD, n=3).

Figure 10:
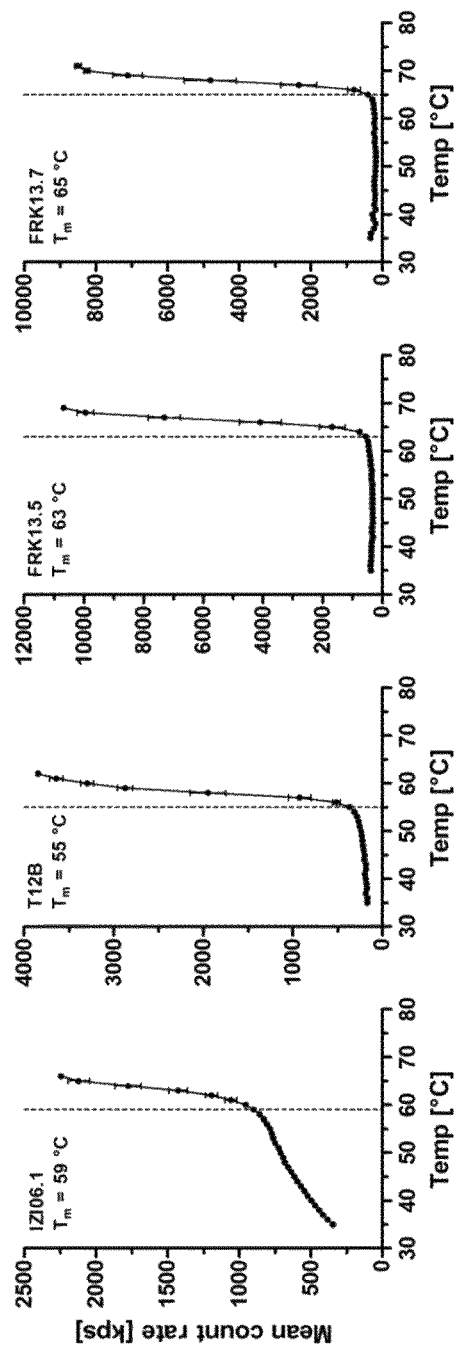

FIG. 10. Thermal stability of humanized scFv fragments. Molecular stability of the scFv antibodies was analyzed by dynamic light scattering. $T_m$ was determined by visual interpretation of the displayed data points.

FIG. 11. Expression and Purification of IgG13.7 and Fab13.7. Expression and purification was evaluated by SDS-PAGE (a, 12% separation gel, reducing conditions; b, 8% separation gel, reducing conditions) and size exclusion chromatography (c, Yarra SEC-2000 column, flow rate 0.5 ml/min). The indicated molecular weight was interpolated according to standard proteins of known mass and retention time.

Figure 12:
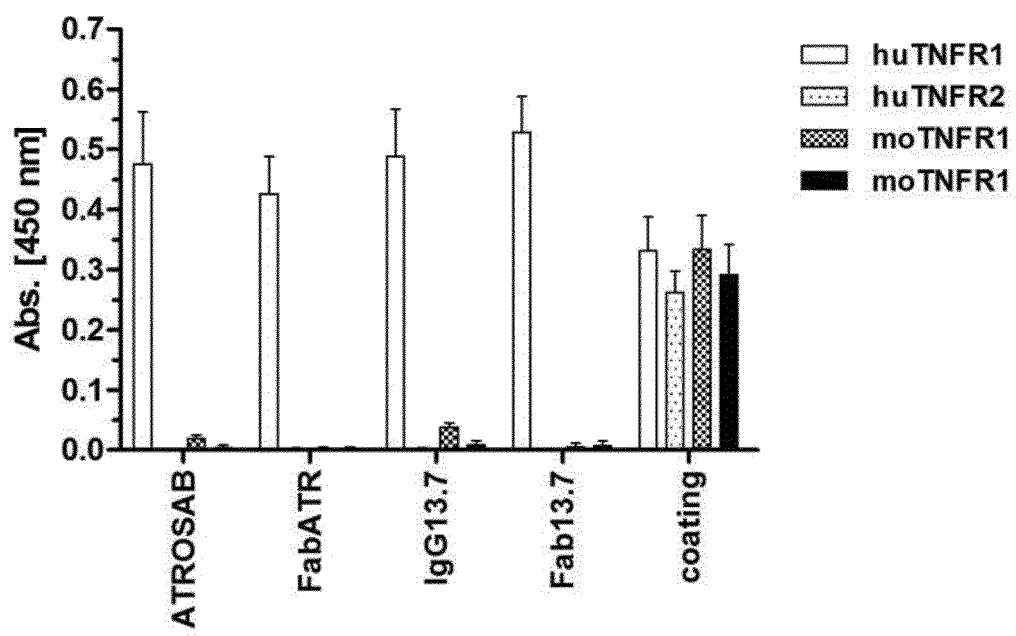

FIG. 12. Species selectivity of scFv13.7 derivatives. Binding of IgG13.7 and Fab13.7 to TNFR1 and -2 of both, human and mouse origin, was tested in standard ELISA. Presented are mean and SD of two individual experiments.

Figure 13:
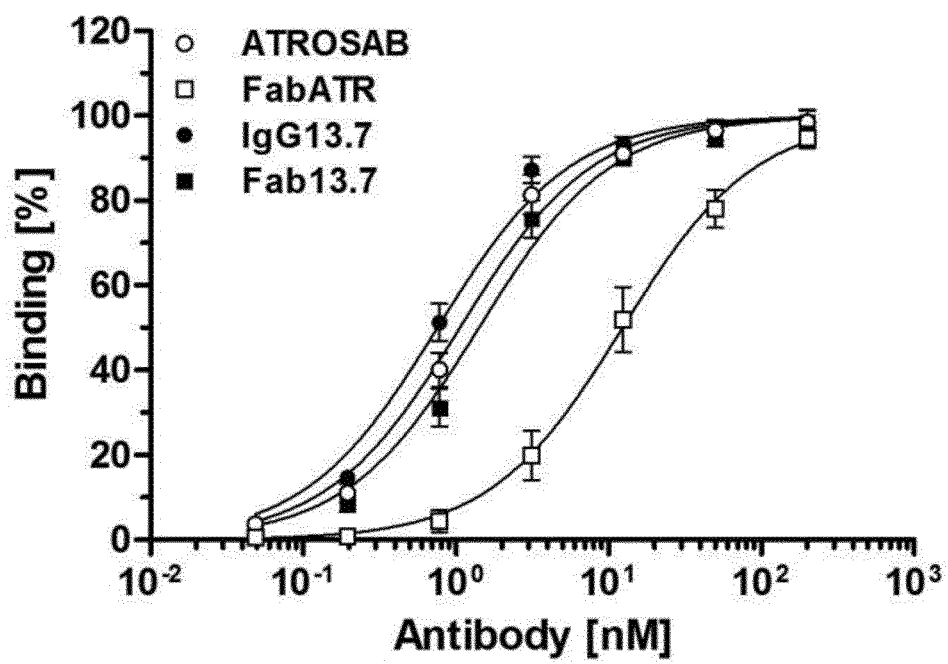

FIG. 13. Equilibrium binding of FRK13.7 antibodies to human TNFR1-Fc. Increasing concentrations were tested for their binding to huTNFR1-Fc in ELISA (n=3, mean±SD).

Figure 14:
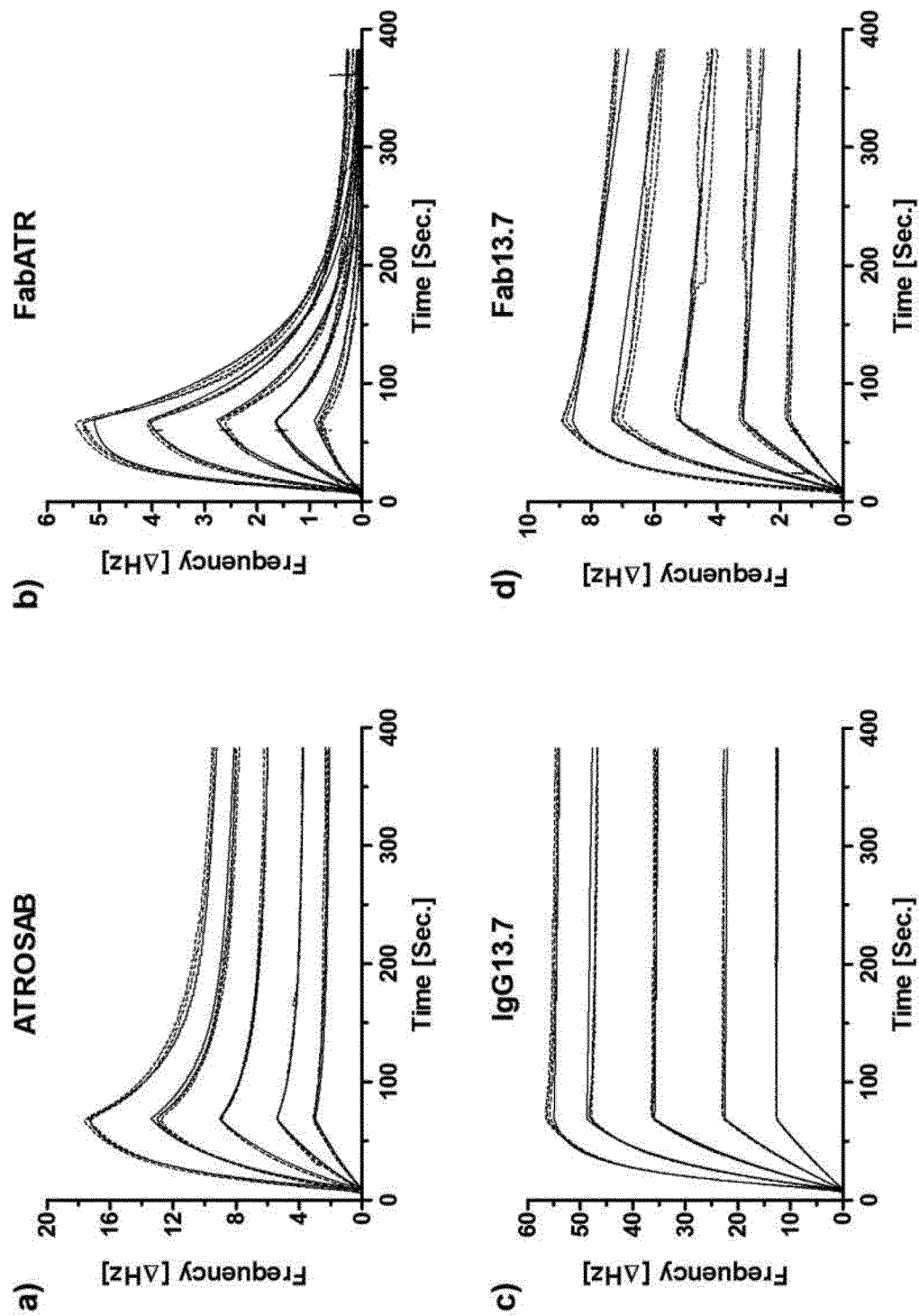

FIG. 14. QCM analysis of IgG and Fab derived from scFvFRK13.7. Real-time kinetic data of the interaction of ATROSAB (a), FabATR (b), IgG13.7 (c) and Fab13.7 (d) with human TNFR1-Fc were collected using a quartz crystal microbalance. Analyzed were triplicates of concentration between 64 nM and 4 nM (ATROSAB and IgG13.7) or 128 nM to 8 nM (FabATR and Fab13.7).

Figure 15:
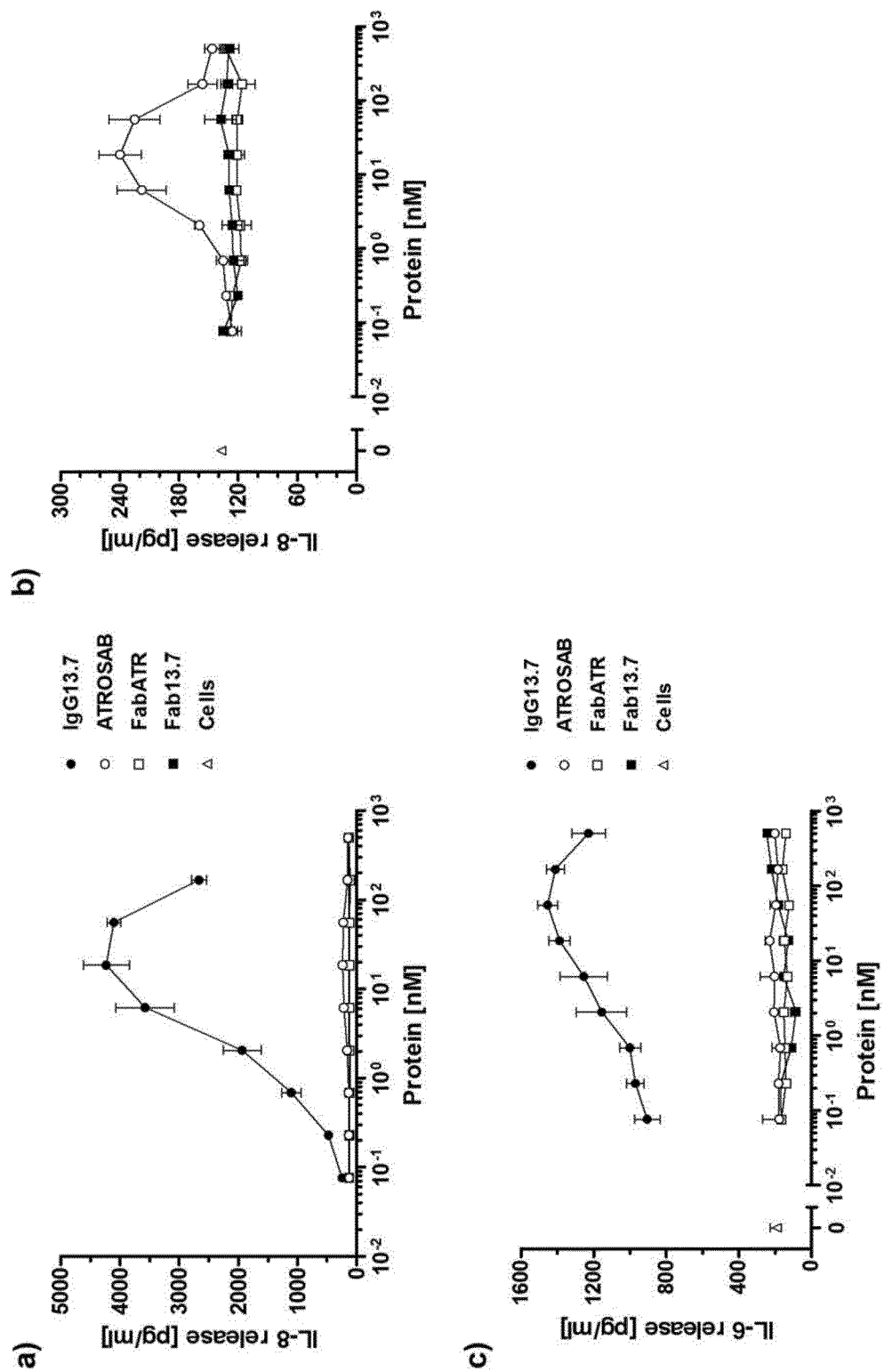

FIG. 15. Bioactivity of FRK13.7 antibodies. IL-8 release from HT1080 cells triggered by FRK13.7 antibody formats is displayed in a and b (increased in size to show low and non-agonistic constructs) together with IL-6 release from HeLa cells (c). TNF, ATROSAB and FabATROSAB (FabATR) served as controls. Presented are mean and SD of two individual experiments.

Figure 16:
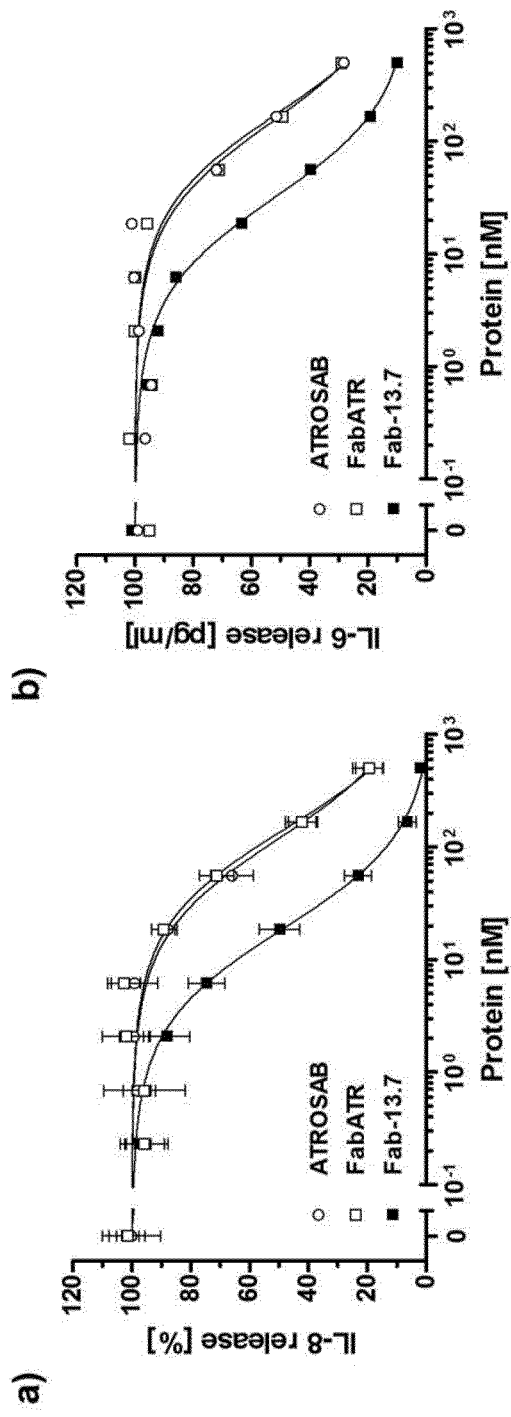

FIG. 16. Inhibition of TNF induced interleukin release by Fab13.7. Presented is the inhibition of IL-8 (a) and IL-6 release (b), induced by 0.1 nM TNF. ATROSAB and FabATROSAB (FabATR) served as controls. Presented are mean and SD of three individual experiments.

Figure 17:
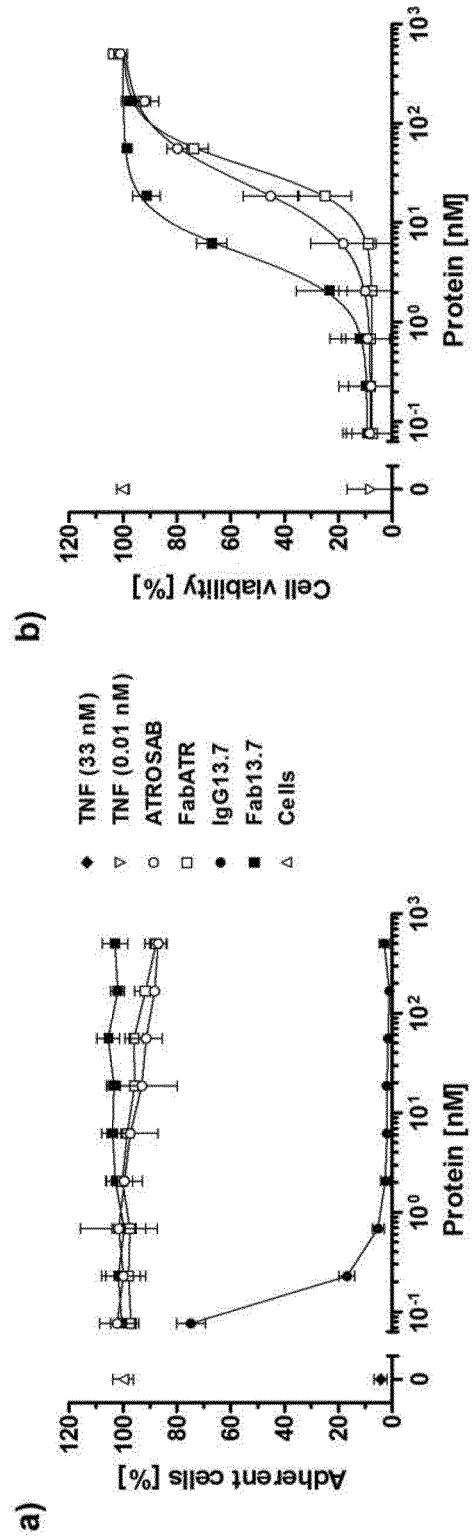

FIG. 17. Induction and inhibition of Kym-1 cytotoxicity. The potential of IgG13.7 and Fab13.7 to trigger cell death in Kym-1 cells was analyzed by KV staining of the remaining adherent cells (a). In the same assay the inhibitory potential of Fab13.7 to inhibit cytotoxicity induced by 0.01 nM TNF was analyzed (b). ATROSAB and FabATR served as controls. Presented are mean and SD of two to three individual experiments (stimulation of cytotoxicity [a] n=2, inhibition [b] n=3).

FIG. 18. Crosslinking of ATROSAB and Fab13.7. Concentration dependent binding of a Fab-specific polyclonal goat serum to Fab3.7 was demonstrated by ELISA (a). In a IL-8 release assay the effect of cross linked Fab13.7 on HT1080 was analyzed, compared with ATROSAB (n=2, mean±SD), using 64 μg/ml of Fab-specific goat serum.

FIG. 19. Pharmacokinetic study of Fab13.7 and FabATR. Initial and terminal plasma half-live after single-dose injection (25 μg), as well as bioavailability (area under the curve) of ATROSAB were determined using C57BL/6J mice (n=3) homozygously bearing the extracellular domain of human TNFR1 at the locus of the mouse gene. Remaining active antibody in serum samples was detected by ELISA.

FIG. 20. Production and bioactivity of Fab13.7$_{PEG}$. a) genotype of Fab13.7PEG. b) Modification with Polyethylene glycole (PEG) of purified protein was analyzed by SDS-PAGE (12%, Coomassie-stained). Varying TCEP (Tris (2-carboxyethyl)phosphin) concentrations and PEG chains of different lengths (5 kDa, 20 kDa, 40 kDa) were used. c) Fab13.7$_{PEG}$ was tested by ELISA for binding to human TNFR1-Fc (n=3, Mean±SD). d) IL-6 release from HeLa cells triggered by Fab13.7$_{PEG}$ was analyzed as well as the inhibition of TNF-induced IL-6 release, using 0.1 nM recombinant human TNF (e, n=3, Mean±SD). f) Initial and terminal plasma half-live after single-dose injection (25 μg), as well as bioavailability (area under the curve) of Fab13.7$_{PEG}$ and the reference proteins Fab13.7 and ATROSAB were determined using C57BL/6J mice (n=3) homozygously bearing the extracellular domain of human TNFR1 at the locus of the mouse gene. Remaining active antibody in serum samples was detected by ELISA.

FIG. 21. Production and bioactivity of Fab13.7-MSA. a) genotype of Fab13.7-MSA. b) Purified protein was analyzed by SDS-PAGE (12%, Coomassie-stained) and subsequently by SEC (c, Yarra SEC-2000 column, flow rate 0.5 ml/min). d) Fab13.7-MSA was tested by ELISA for binding to human TNFR1-Fc (n=2, Mean+SD). e) IL-8 release from HT1080 cells triggered by Fab13.7-MSA was analyzed (n=1, Mean±SD of duplicates) as well as the inhibition of TNF-induced IL-8 release, using 0.1 nM recombinant human TNF (f, n=2, Mean±SD). g) Initial and terminal plasma half-live after single-dose injection (25 μg), as well as bioavailability (area under the curve) of Fab13.7-MSA and the reference proteins Fab13.7 and ATROSAB were determined using C57BL/6J mice (n=3) homozygously bearing the extracellular domain of human TNFR1 at the locus of the mouse gene. Remaining active antibody in serum samples was detected by ELISA.

FIG. 22. Production and bioactivity of IgG13.7$_{half}$. a) genotype of IgG13.7$_{half}$. b) Purified protein was analyzed by SDS-PAGE (12%, Coomassie-stained) and subsequently by SEC (c, Yarra SEC-2000 column, flow rate 0.5 ml/min). d) IgG13.7$_{half}$ was tested by ELISA for binding to human TNFR1-Fc (n=2, Mean±SD). e) IL-8 release from HT1080 cells triggered by IgG13.7$_{half}$ was analyzed (n=1, Mean±SD of duplicates) as well as the inhibition of TNF-induced IL-8 release, using 0.1 nM recombinant human TNF (f, n=2, Mean±SD). g) Initial and terminal plasma half-live after single-dose injection (25 μg), as well as bioavailability (area under the curve) of IgG13.7$_{half}$ and the reference proteins Fab13.7 and ATROSAB were determined using C57BL/6J mice (n=3) homozygously bearing the extracellular domain of human TNFR1 at the locus of the mouse gene. Remaining active antibody in serum samples was detected by ELISA.

FIG. 23. Production and bioactivity of Fab13.7-Fc$_{kih}$0DS. a) genotype of Fab13.7-Fc$_{kih}$0DS. b) Purified protein was analyzed by SDS-PAGE (12%, Coomassie-stained) and subsequently by SEC (c, Yarra SEC-3000 column, flow rate 0.5 ml/min). d) Fab13.7-Fc$_{kih}$0DS was tested by ELISA for binding to human TNFR1-Fc (n=2, Mean±SD). e) IL-8 release from HT1080 cells triggered by Fab13.7-Fc$_{kih}$0DS was analyzed (n=2, Mean±SD) as well as the inhibition of TNF-induced IL-8 release, using 0.1 nM recombinant human TNF (f, n=2, Mean±SD). g) Initial and terminal plasma half-live after single-dose injection (25 μg), as well as bioavailability (area under the curve) of Fab13.7-$Fc_{kih}$0DS and the reference proteins Fab13.7 and ATROSAB were determined using C57BL/6J mice (n=3) homozygously bearing the extracellular domain of human TNFR1 at the locus of the mouse gene. Remaining active antibody in serum samples was detected by ELISA.

Figure 24:
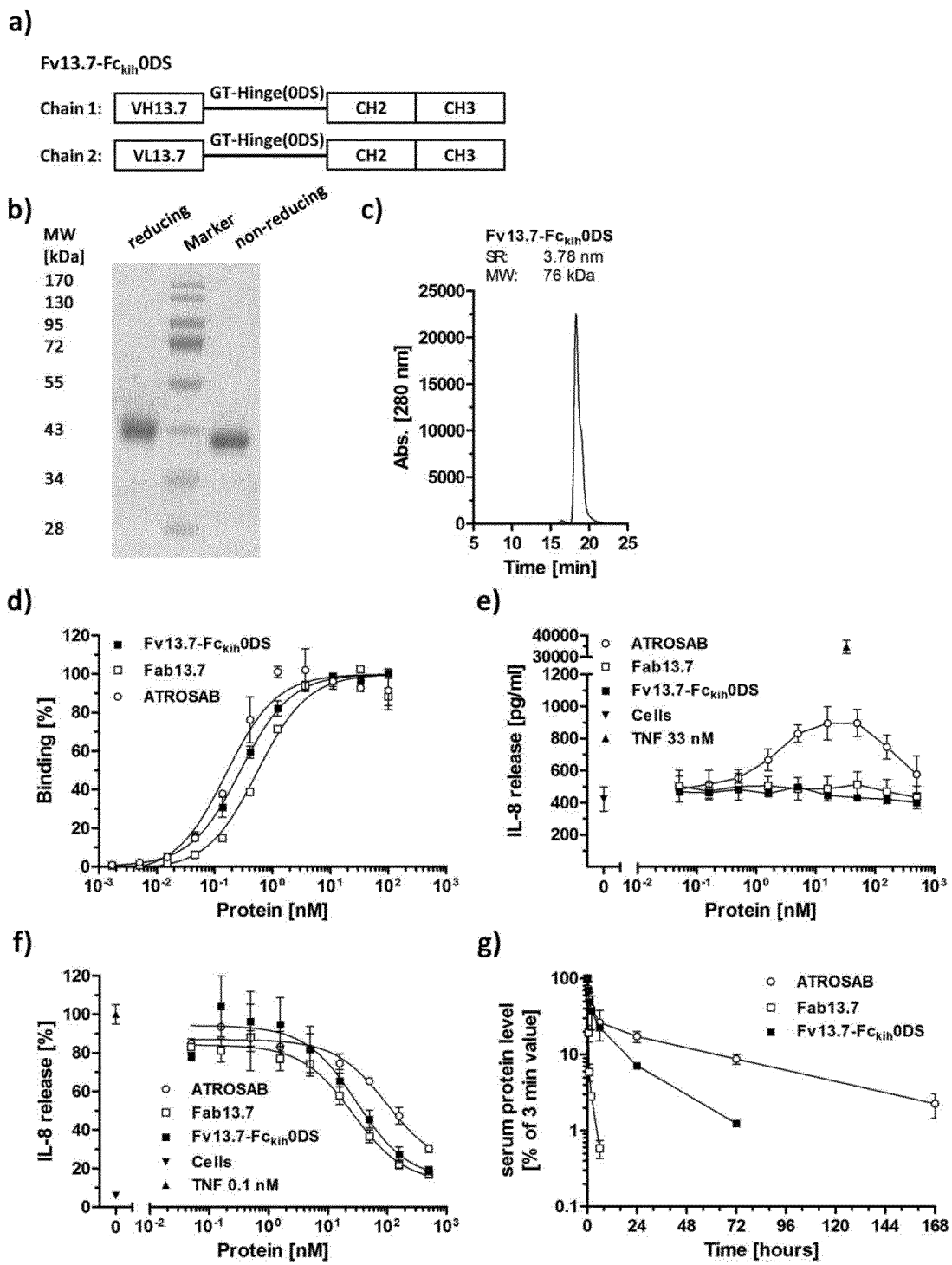

FIG. 24. Production and bioactivity of Fv13.7-$Fc_{kih}$0DS. a) genotype of Fv13.7-$Fc_{kih}$0DS. b) Purified protein was analyzed by SDS-PAGE (12%, Coomassie-stained) and subsequently by SEC (c, Yarra SEC-3000 column, flow rate 0.5 ml/min). d) Fv13.7-$Fc_{kih}$0DS was tested by ELISA for binding to human TNFR1-Fc (n=1, Mean±SD of duplicates). e) IL-8 release from HT1080 cells triggered by Fv13.7-$Fc_{kih}$0DS was analyzed (n=2, Mean±SD) as well as the inhibition of TNF-induced IL-8 release, using 0.1 nM recombinant human TNF (f, n=2, Mean±SD). g) Initial and terminal plasma half-live after single-dose injection (25 μg), as well as bioavailability (area under the curve) of Fv13.7-$Fc_{kih}$0DS and the reference proteins Fab13.7 and ATROSAB were determined using C57BL/6J mice (n=3) homozygously bearing the extracellular domain of human TNFR1 at the locus of the mouse gene. Remaining active antibody in serum samples was detected by ELISA.

FIG. 25. Antibody sequences (SEQ ID 1-33)
SEQ ID 1: CDRH1 of H398 or ATROSAB
SEQ ID 2: CDRH2 of H398 or ATROSAB
SEQ ID 3: CDRH3 of H398 or ATROSAB
SEQ ID 4: CDRL1 of H398 or ATROSAB
SEQ ID 5: CDRL2 of H398 or ATROSAB
SEQ ID 6: CDRL3 of H398 or ATROSAB
SEQ ID 7: CDRH2 variants of SEQ ID 2
SEQ ID 8: CDRL3 variants of SEQ ID 6
SEQ ID 9: CDRH2 variant IG11
SEQ ID 10: CDRH2 variants T12B or Fab13.7
SEQ ID 11: CDRL3 variant T12B
SEQ ID 12: VH sequence of IG11
SEQ ID 13: VH sequence of T12B or 13.5 or 13.7
SEQ ID 14: VH sequence of 13.1 or 13.3 or 13.6
SEQ ID 15: VH sequence of 13.2 or 13.4 or 13.8
SEQ ID 16: VL sequence of IG11
SEQ ID 17: VL sequence of T12B or 13.6 or 13.8
SEQ ID 18: VL sequence of 13.1 or 13.4 or 13.5
SEQ ID 19: VL sequence of 13.2 or 13.3 or 13.7
SEQ ID 20: VH sequence of scFvIZI06.1
SEQ ID 21: VL sequence of scFvIZI06.1
SEQ ID 22: ATROSAB VH
SEQ ID 23: ATROSAB VL
SEQ ID 24: human IgG Fc
SEQ ID 25: Heavy chain of Fab13.7
SEQ ID 26: Light chain of Fab13.7
SEQ ID 27: Heavy chain of Fab13.7$_{PEG}$
SEQ ID 28: Heavy chain of Fab13.7-MSA
SEQ ID 29: Heavy chain of IgG13.7$_{half}$
SEQ ID 30: Fd13.7-Fc0DS
SEQ ID 31: LC13.7-Fc0DS
SEQ ID 32: VH13.7-Fc0DS
SEQ ID 33: VL13.7-Fc0DS
SEQ ID 34: Fab13.7 MODIFICATION TO INSERT PEG
SEQ ID 35: Hinge$_{0DS}$
SEQ ID 36: Sequence introduced in FR1 of scFvFRK13.7
SEQ ID 37: Sequence introduced in FR1 of scFvFRK13.7
SEQ ID 38: Sequence introduced in FR3 of scFvFRK13.7
SEQ ID 39: Sequence introduced in FR1 of FRK13.1 and FRK13.2
SEQ ID 40: Sequence introduced in FR3 of FRK13.1 and FRK13.2
SEQ ID 41: Sequence introduced in FR3 of FRK13.1 and FRK13.2
SEQ ID 42-44: modified hinge regions The nomenclature as used herein shall have the following meaning:
VH CDR1=CDRH1
VH CDR2=CDRH2
VH CDR3=CDRH3
VL CDR1=CDRL1
VL CDR2=CDRL2
VL CDR3=CDRL3

Unless indicated otherwise, reference is herein made to the CDR sequences as numbered according to Kabat, i.e. as determined according to Kabat nomenclature (see Kabat et al., Sequences of Proteins of Immunological Interest, 5$^{th}$ Ed. Public Health Service, U.S. Department of Health and Human Services. (1991)), and in particular those CDR sequences as listed in the Figures. It is well understood that the invention and the scope of the claims shall also encompass the same antibodies and CDR, yet with a different numbering and designated CDR region, where CDR regions are defined according to the IMGT system (The international ImMunoGeneTics, Lefranc et al., 1999, Nucleic Acids Res. 27: 209-212).

DETAILED DESCRIPTION OF THE INVENTION

The use of the terms "a" and "an" and "the" and similar referents in the context of describing the invention (especially in the context of the following claims) are to be construed to cover both the singular and the plural, unless otherwise indicated herein or clearly contradicted by context.

The terms "comprising," "having," "including," and "containing" are to be construed as open-ended terms (i.e., meaning "including, but not limited to,") unless otherwise noted. For the purposes of the present invention the term "consisting of" is considered to be a preferred embodiment of the term "comprising of". If hereinafter a group is defined to comprise at least a certain number of embodiments, this is meant to also encompass a group which preferably consists of these embodiments only.

Herein the "inhibitor" is described as an "antibody construct" or an "antibody". The term "antibody construct" as used herein also simply referred to as "antibody" or "antibody of the invention", shall refer to non-naturally occurring antibodies which are artificial constructs engineered to monovalently bind to the huTNFR1 target, or obtained by cleaving a naturally-occurring antibody into fragments. To this end, the term "antibody" is understood to encompass polypeptides or proteins that consist of or comprise antibody domains, which are understood as constant and/or variable domains of the heavy and/or light chains of immunoglobulins, with or without a linker sequence. Polypeptides are understood as antibody domains, if comprising a beta-barrel structure consisting of at least two beta-strands of an antibody domain structure connected by a loop sequence. Antibody domains may be of native structure or modified by mutagenesis or derivatization, e.g. to modify the antigen binding properties or any other property, such as stability or functional properties, such as binding to the Fc receptors FcRn and/or Fcgamma receptor.

The antibody construct as used herein comprises at least one antigen-binding moiety, wherein only one antigen-binding moiety of the antibody is recognizing the huTNFR1 target. Thus, the binding of the antibody construct to the huTNFR1 receptor is only monovalently. In particular, the antigen-binding moiety comprises an antigen-binding site or an antibody domain that bears an antigen-binding site. Any of the variable antibody domains alone or in combination may be employed to build the antigen-binding site. Specifically, an antigen-binding site is formed by a combination of CDR sequences. Such combination of CDR sequences is also understood as a CDR binding site, e.g. the antigen binding pocket formed by three CDR sequences of one variable domain, such as the combination of CDRH1, CDRH2, and CDRH3, or the combination of CDRL1, CDRL2, and CDRL3, or else six CDR sequences of two variable domains, such as the combination of CDRH1, CDRH2, CDRH3, CDRL1, CDRL2, and CDRL3. Alternatively, an antigen-binding site may be employed that is derived from a natural ligand to the receptor, or an artificial construct.

Specifically, a CDR binding site of a single variable antibody domain may be used as antigen-binding site, such as a binding site of domains of the heavy and light chains of the variable region (such as dAb, Fd, VL, Vkappa, Vlambda, VH, VHH), or a binding site of pairs of variable antibody domains, such as a VH/VL pair.

Thus, the antibody construct comprising a CDR binding site may comprise a single variable antibody domain or a pair of variable binding domains, and optionally further comprise other variable domains, yet, with a different antigen-binding specificity, i.e. a bispecific or polyspecific antibody construct, wherein only one antigen-binding site is directed to huTNFR1, and at least one another antigen-binding site is directed to a target different from huTNFR1, because the antibody construct as further described herein is only monovalently binding to the huTNFR1 target. Optionally, the antibody construct further comprises constant antibody domains, or combinations of variable and/or constant antibody domains with or without a linking sequence or hinge region. Exemplary antibody constructs are Fab, F(ab'), (Fab)$_2$, scFv, Fv, or a full-length antibody.

Exemplary monovalent, monospecific binders are Fab, scFv, Fv, domain antibodies, IgG half-antibodies, or monovalent IgGs, such as a one-armed IgG consisting of a complete light chain, one complete heavy chain and an additional Fc chain lacking Fd (Fd=VH-CH1), which may be produced according to the knobs-into holes techniques (or other asymmetric Fc parts) so to avoid homodimerization of heavy chains.

Divalent formats may as well be used, wherein only one valency is recognizing the TNFR1 target, and the other valency is recognizing a different target. Thus, bispecific or oligospecific constructs comprising two or more antigen-binding sites may be used, as long as only one antigen-binding site is directed to the TNFR1 receptor.

The term "full-length antibody" is used to refer to any divalent antibody molecule comprising at least most of the Fc domain and other domains commonly found in a naturally occurring antibody monomer. This phrase is used herein to emphasize that a particular antibody molecule is not an antibody fragment.

The term "Fv" is herein understood as the region of variable domains which incorporates the CDR binding site, e.g. of VH, VL or VH/VL. The term "Fv", thus, particularly applies to either VH, VL, or the VH/VL which is the VH domain associated to a VL domain by an interaction between the beta-sheet structure of both variable domains, with or without a linker.

Moreover, the term "antibody" shall specifically include antibodies in the isolated form, which are substantially free of other antibodies directed against different target antigens or comprising a different structural arrangement of antibody domains. Still, an isolated antibody may be comprised in a combination preparation, containing a combination of the isolated antibody, e.g. with at least one other antibody, such as monoclonal antibodies or antibody fragments having different specificities, or a combination of further therapeutically active substances and/or auxiliary agents.

The term "antibody" shall apply to antibodies of animal origin, including human species, such as mammalian, including human, murine, rabbit, goat, lama, cow and horse, or avian, such as hen, which term shall particularly include recombinant antibodies which are based on a sequence of animal origin, e.g. human sequences. In particular, the term applies to antibody constructs comprising or consisting of humanized or human sequences, which is preferred when the antibody construct is provided for pharmaceutical purposes to treat a human subject.

In some embodiments, chimeric antibodies may be used with sequences of origin of different species, such as sequences of murine and human origin.

The term "chimeric" as used with respect to an antibody refers to those antibodies wherein one portion of each of the amino acid sequences of heavy and light chains is homologous to corresponding sequences in antibodies derived from a particular species or belonging to a particular class, while the remaining segment of the chain is homologous to corresponding sequences in another species or class. Typically the variable region of both light and heavy chains mimics the variable regions of antibodies derived from one species of mammals, while the constant portions are homologous to sequences of antibodies derived from another. For example, the variable region can be derived from presently known sources using readily available B-cells or hybridomas from non-human host organisms in combination with constant regions derived from, for example, human cell preparations.

The term "humanized" as used with respect to an antibody refers to a molecule having an antigen binding site that is substantially derived from an immunoglobulin from a non-human species, wherein the remaining immunoglobulin structure of the molecule is based upon the structure and/or sequence of a human immunoglobulin. The antigen binding site may either comprise complete variable domains fused onto constant domains or only the complementarity determining regions (CDR) grafted onto appropriate framework regions in the variable domains. Antigen-binding sites may be wild-type or modified, e.g. by one or more amino acid substitutions, preferably modified to resemble human immunoglobulins more closely. Some forms of humanized antibodies preserve all CDR sequences (for example a humanized mouse antibody which contains all six CDRs from the mouse antibody). Other forms have one or more CDRs which are altered with respect to the original antibody.

There is no limitation as to the technique of humanization of the antibody, as long as the antibody binds to the desired antigen. Examples of humanization include, without limitation thereto, complementarity determining region grafting (CDR grafting) (Jones et al. 1986, Nature 321, 522-525), specificity determining residue grafting (SDR grafting) (Kashmiri et al., 2005, Methods 36, 25-34), resurfacing of variable domains (Roguska et al., 1994, Proc. Natl. Acad.

Sci. USA 91, 969-973), structure-based selection and humanization by CDR grafting (Hwang et al., 2005, Methods 36, 35-42), and de-Immunization strategies (Hellendom et al., 2004, Cancer Cell International 4 (Suppl. I), 20).

In a specific embodiment of the present invention, the antibody described herein is a humanized antibody, which contains amino acid sequences of human origin and such of non-human, e.g. rodent origin.

In a preferred embodiment, the antibody described herein may comprise an Fc region derived from a humanized antibody obtainable by e.g. recombinant nucleic acid technology. In this regard the antibody, or at least one fragment thereof, may contain one or more mutations or variations, such as added, deleted or substituted amino acids or nucleic acids, as long as it has no negative effect on the interaction with huTNFR1. Further, the antibody may contain one or more mutations or variations, such as added, deleted or substituted amino acids or nucleic acids, which have a positive effect on the interaction of huTNFR1 and which improve the antagonistic activity of said molecule. In particular, such mutated variants have a better affinity and/or a better inhibitory activity.

For example, the antibody may be a humanized antibody having the same binding specificity as the murine antibody H398, yet, monovalently binding to the target huTNFR1, and is preferably derived from H398, using the H398 antibody as a parental antibody. Though the binding specificity is preferably the same, the fine specificity may change due to humanization or other mutation techniques.

The mouse anti-human TNFR1 monoclonal antibody H398 is characterized by the VH and VL sequences as depicted in WO2008113515A2. Upon humanization, humanized VH and VL sequences were obtained, which are characterized by sequences as depicted in WO2008113515A2 (IZI-06.1 VH (SEQ ID 20), IZI-06.1 VL (SEQ ID 21)). The humanized antibody has been converted into an IgG1 molecule (ATROSAB) containing a modified Fc region deficient in mediating effector functions, and still being characterized by the VH and VL sequences of IZI-06.1 VH and IZI-06.1 VL. The sequences of WO2008113515A2 are herein incorporated by reference.

Purified ATROSAB, produced in CHO cells, showed strong binding to human and rhesus TNFR1-Fc fusion protein and mouse embryonic fibroblasts transfected with a recombinant TNFR1 fusion protein with an affinity identical to the parental mouse antibody H398. Using chimeric human/mouse TNFR1 molecules, the epitope of ATROSAB was mapped to the N-terminal region (amino acid residues 1-70) comprising the first cysteine-rich domain (CRD1) and the A1 sub-domain of CRD2. In vitro, ATROSAB effectively inhibited typical TNF-mediated responses like apoptosis induction and activation of NFκB-dependent gene expression such as IL-6 and IL-8 production.

Since the H398 or ATROSAB antibody is characterized by a high avidity, yet, medium-affinity when measured for the Fab format (e.g. if the antigen-binding site is provided in the form of the respective Fab fragment), by QCM at physiological conditions, it was the aim to improve the therapeutic potential by increasing affinity to TNFR1. However, upon affinity maturation of ATROSAB, a complete, divalent derivative binding TNFR1 with higher affinity turned out to be highly agonistic, which would pose a problem to the treatment of patients.

The antibody described herein monovalently binds to the target, and thereby surprisingly overcomes such problem of agonistic activity at high affinities, even when the dissociation of the antibody from the receptor is low (low $k_{off}$ rate).

Preferably, the antibody described herein has a specificity to bind to the epitope that comprises or consists essentially of at least the membrane-distal CRD1 and subdomain A1 of CRD2 of huTNFR1.

In a specific embodiment the antibody described herein comprises one or more of the complementary determining regions (CDRs) of H398, such as described in WO2008/113515A2, or parts thereof, conferring binding to huTNFR1. The CDRs of H398 or ATROSAB may be present in any combination, for example two, three, four, five or six of said CDRs may be present. Additionally, multiple copies or genetic variants of any of the CDRs may be present in the huTNFR1-antibody described herein, as long as the antibody shows sufficient affinity towards human TNFR1.

The term "human" as used with respect to an antibody is understood to include antibodies having variable and constant regions derived from human germline immunoglobulin sequences. The human antibody described herein may include amino acid residues not encoded by human germline immunoglobulin sequences (e.g., mutations introduced by random or site-specific mutagenesis in vitro or by somatic mutation in vivo), for example in the CDRs. Human antibodies include antibodies isolated from human immunoglobulin libraries or from animals transgenic for one or more human immunoglobulin.

The term "antibody" specifically includes antibodies of any class or subclass. Depending on the amino acid sequence of the constant domain of their heavy chains, antibodies can be assigned to the major classes of antibodies IgA, IgD, IgE, IgG, and IgM, and several of these may be further divided into subclasses (isotypes), e.g., IgG1, IgG2, IgG3, IgG4, IgA1, and IgA2.

The term further applies to monoclonal or polyclonal antibodies, specifically a recombinant antibody, which term includes all antibodies and antibody structures that are prepared, expressed, created or isolated by recombinant means, such as antibodies originating from animals, e.g. mammalians including human, that comprises genes or sequences from different origin, e.g. murine, chimeric, humanized antibodies, or hybridoma derived antibodies. Further examples refer to antibodies isolated from a host cell transformed to express the antibody, or antibodies isolated from a recombinant, combinatorial library of antibodies or antibody domains, or antibodies prepared, expressed, created or isolated by any other means that involve splicing of antibody gene sequences to other DNA sequences.

It is understood that the term "antibody" also refers to derivatives of an antibody, in particular functionally active derivatives. An antibody derivative is understood as any combination of one or more antibody domains or antibodies and/or a fusion protein, in which any domain of the antibody may be fused or linked at any position of one or more other proteins or chemicals, such as other antibodies, e.g. a binding structure comprising CDR loops, a receptor polypeptide, but also ligands, scaffold proteins, enzymes, toxins and the like. A derivative of the antibody may be obtained by association or binding to other substances by various chemical techniques such as covalent coupling, electrostatic interaction, di-sulphide bonding etc. The other substances bound to the antibody may be lipids, carbohydrates, nucleic acids, organic and inorganic molecules or any combination thereof, e.g. prodrugs or drugs. Specific embodiments refer to binding the antibody to a hydrophilic polymer to obtain a functionally active derivative of an antibody construct coupled to a hydrophilic polymer, such as PEG, and/or fused to a polypeptide, such as human serum albumin, transferrin, Ig binding domains, PEG mimetic polypeptide extensions, an antibody Fc fragment, or a functional variant of any of the foregoing polypeptides. Such functionally active derivative is e.g. a PEGylated, HESylated, or PSAylated antibody construct. Such antibody construct is modified by linkage to a half-life extending moiety such as polyethylene glycol (PEGylation), glycosylated PEG, hydroxyl ethyl starch (HE-Sylation), or poly-sialic acids (PSA). Specifically the derivative is produced by covalent attachment of one or more molecules of the half-life extending moiety.

According to a specific aspect, the antibody construct described herein comprises a functionally active Fc variant, which is derived from any of the naturally-occurring variants of human IgG Fc (SEQ ID 24).

Functionally active Fc variants may be obtained by changing the sequence above and are characterized by having a biological activity similar to that displayed by the respective sequence, including the ability to stabilize an antibody or to confer a prolonged half-life. The preferred Fc variants as used in an antibody described herein comprise mutations to reduce the Fc effector functions.

Functionally active derivatives are particularly produced by fusion or covalent chemical modification that does not alter the primary amino acid sequence of the antibody itself. Derivatives may e.g. have desired properties including, for example, prolonging the circulation half-life, increasing the stability, reducing the clearance, or altering the immunogenicity.

In a specific embodiment of the present invention, the huTNFR1 antibody comprises an additional tag allowing specific interaction with a biologically acceptable compound. There is not a specific limitation with respect to the tag usable in the present invention, as far as it has no or tolerable negative impact on the monovalent binding of the huTNFR1-antibody to huTNFR1 or the immunogenic response when administered to a human being. Examples of suitable tags include His-tag, Myc-tag, FLAG-tag, Strep-tag, Calmodulin-tag, GST-tag, MBP-tag, and S-tag.

The antibody described herein may be conjugated to a label or reporter molecule, e.g. selected from the group consisting of organic molecules, enzyme labels, radioactive labels, colored labels, fluorescent labels, chromogenic labels, luminescent labels, haptens, digoxigenin, biotin, metal complexes, metals, colloidal gold and mixtures thereof. Antibodies conjugated to labels or reporter molecules may be used, for instance, in assay systems or diagnostic methods.

The antibody described herein may be conjugated to other molecules which allow the simple detection of said conjugate in, for instance, binding assays (e.g. ELISA) and binding studies.

It is understood that the term "antibody" also refers to variants of an antibody, including antibodies with functionally active CDR variants of a parent CDR sequence, and functionally active variant antibodies of a parent antibody.

Specifically, an antibody may be used which is derived from an antibody as herein exemplified by its CDR sequences and optionally by its VH and/or VL sequences. Thus, the exemplified antibodies may serve as parent antibody to obtain derivatives, wherein one or more of the CDR regions or CDR variants are produced while maintaining the functional activity.

Antibodies derived from a parent antibody or antibody sequence, such as a parent CDR or FR sequence, are herein particularly understood as mutants or variants of a parent sequence obtained by e.g. in silico or recombinant engineering or else by chemical derivatization or synthesis.

Specifically, an antibody derived from an antibody as described herein may comprise at least one or more of the CDR regions or CDR variants thereof, e.g. at least 3 CDRs of the heavy chain variable region and/or at least 3 CDRs of the light chain variable region, with at least one point mutation in at least one of the CDR or FR regions, or in the constant region of the HC or LC, being functionally active.

The term "variant" shall particularly refer to antibodies, such as mutant antibodies or fragments of antibodies, e.g. obtained by mutagenesis methods, in particular to delete, exchange, introduce inserts into a specific antibody amino acid sequence or region or chemically derivatize an amino acid sequence, e.g. in the constant domains to engineer the antibody stability, effector function or half-life, or in the variable domains to improve antigen-binding properties, e.g. by affinity maturation techniques available in the art. Any of the known mutagenesis methods may be employed, including point mutations at desired positions, e.g. obtained by randomization techniques. In some cases positions are chosen randomly, e.g. with either any of the possible amino acids or a selection of preferred amino acids to randomize the antibody sequences. The term "mutagenesis" refers to any art recognized technique for altering a polynucleotide or polypeptide sequence. Preferred types of mutagenesis include error prone PCR mutagenesis, saturation mutagenesis, or other site directed mutagenesis.

The term "variant" shall specifically encompass functionally active variants.

The term "functionally active variant" of a CDR sequence as used herein, is understood as a "functionally active CDR variant", and the "functionally active variant" of an antibody as used herein, is understood as "functionally active antibody variant". The functionally active variant means a sequence resulting from modification of this sequence (a parent antibody or a parent sequence) by insertion, deletion or substitution of one or more amino acids, or chemical derivatization of one or more amino acid residues in the amino acid sequence, or nucleotides within the nucleotide sequence, or at either or both of the distal ends of the sequence, e.g. in a CDR sequence the N-terminal and/or C-terminal 1 or 2 amino acids, and/or the centric 1 or amino acids (i.e. in the midst of the CDR sequence), and which modification does not affect, in particular impair, the activity of this sequence. In the case of a binding site having specificity to a selected target antigen, the functionally active variant of an antibody would still have the same or predetermined binding specificity, though this could be changed, e.g. to change the fine specificity to a specific epitope, the affinity, the avidity, the $K_{on}$ or $K_{off}$ rate, etc. For example, an affinity-matured antibody is specifically understood as a functionally active variant antibody. Hence, the modified CDR sequence in an affinity-matured antibody is understood as a functionally active CDR variant.

In a preferred embodiment the functionally active variant of a parent antibody a) is a biologically active fragment of the antibody, the fragment comprising at least 50% of the sequence of the molecule, preferably at least 60%, at least 70%, at least 80%, at least 90%, or at least 95% and most preferably at least 97%, 98% or 99%;

b) is derived from the antibody by at least one amino acid substitution, addition and/or deletion, wherein the functionally active variant has a sequence identity to the molecule or part of it, such as an antibody of at least 50% sequence identity, preferably at least 60%, more preferably at least 70%, more preferably at least 80%, still more preferably at least 90%, even more preferably at least 95% and most preferably at least 97%, 98% or 99%; and/or c) consists of the antibody or a functionally active variant thereof and additionally at least one amino acid or nucleotide heterologous to the polypeptide or the nucleotide sequence.

In one preferred embodiment of the invention, the functionally active variant of the antibody described herein is essentially identical to the variant described above, but differs from its polypeptide or the nucleotide sequence, respectively, in that it is derived from a homologous sequence of a different species.

Specifically, functionally active antibody constructs, variants or derivatives as described herein are functionally active with regard to the TNFR1 antigen binding, in particular the high affinity of binding (particularly as determined by the $K_D$ and $k_{off}$ rates), and further considering avoiding any potential agonistic side effects, e.g. as determined in a cell-based assay. Exemplary assays for determining inhibition of TNFR1 mediated cell death employ Kym-1 cells. Further exemplary assays for determining TNF- or LTalpha-mediated inflammatory response determine inhibition of IL-6 or IL-8 release from HeLa cells or HT1080 cells, respectively. Such assays are exemplified in the examples section.

Functionally active variants may be obtained, e.g. by changing the sequence of a parent antibody, e.g. an antibody comprising the same binding site as any of the antibodies as listed in the figures, but with modifications within an antibody region besides the binding site, or derived from such parent antibody by a modification within the binding site but that does not impair the antigen binding, and preferably would have substantially the same biological activity as the parent antibody or even an improved activity, including the ability to specifically or selectively bind TNFR1 antigen, e.g. with high affinity and optionally by a high association and a low dissociation to bind the antigen.

The primary function of the antibody construct as described herein is the function as an inhibitor of the TNF-huTNFR1 interaction. The term "inhibitor" as understood herein is a substance having the capability to a) modulate (e.g reduce or eliminate) TNFR1 signaling in vitro and/or in vivo, and/or b) to inhibit the TNFR1-mediated cell death in vitro and/or in vivo, and/or c) to inhibit TNF-mediated cellular stimulation to release inflammatory cytokines in vitro and/or in vivo, by inhibition of TNFR1 signaling or a different mechanism. Such capability or function is specifically considered to be the desired biological activity in accordance with the subject invention. In particular, the inhibitor as described herein interferes with the binding of one or more molecules TNF to one or more molecules of TNFR1 on the cell surface. For therapeutic applications, without being bound by theory, TNF-huTNFR1 interaction inhibitors of the subject invention can have the capability to inhibit huTNFR1 signaling in the presence of TNF, or huTNFR1 mediated cell death in the presence of TNF, or to inhibit cellular stimulation to release inflammatory cytokines in the presence of TNF. Treatment for an inflammatory disorder or disease can proceed by the TNF-huTNFR1 interaction inhibitor's anti-inflammatory activity, regardless of underlying mechanism. By downmodulating or blocking the TNF-huTNFR1 protein-protein interaction, an effect on inflammatory disease can be achieved.

As used herein, the term "signaling" and "signaling transduction" represents the biochemical process involving transmission of extracellular stimuli, via cell surface receptors through a specific and sequential series of molecules, to genes in the nucleus resulting in specific cellular responses to the stimuli.

Inhibition of the huTNFR1 interaction may lead to a downmodulation of the effects of TNFR1 signaling or signal transduction, as measured ex vivo in a cell-based assay or in vivo, in a dose-dependent way. The functional activity of the inhibitor or antibody constructs and variants or derivatives is specifically characterized by an inhibitory function which inhibits the TNF-huTNFR1 interaction or LTα-huTNFR1 interaction in vivo, as determined in an ex vivo cell-based assay. A further assay may be employed to exclude substantial side effects associated with cross-linking the TNFR1 receptor that would agonise the TNF-TNFR1 interaction. A suitable assay is determining the activity of the antibody or variant on HeLa or HT1080 cells for the absence of stimulatory activity to produce the inflammatory cytokines IL-6 or IL-8, respectively. An exemplary test is described in the examples section below.

Inhibition typically leads to a reduction of effects of huTNFR1 interaction or activity by at least 50%, or at least 60%, or at least 70%, or at least 80%, or at least 90%, or the maximum level. Methods for producing and characterizing an inhibitor or antibody described herein are well-known in the art. In a preferred embodiment, antibody variants are produced and screened for predefined properties using one or more cell-based assays employing huTNFR1 expressing cells or in vivo assays. For such assays, the antibody is typically added exogenously such that cells can be bound, e.g. in the presence and absence of TNF to determine the antagonistic and agonistic activity. These assays are typically based on the function of the immunoglobulin; that is, the ability of the antibody to bind to huTNFR1 and mediate some biochemical event, for example the blocking of TNF binding to said cells, e.g. in a competitive binding assay, TNF/receptor binding inhibition, the reduction of cytokine expression in the presence or absence of TNF, specifically inflammatory interleukins, such as IL-6 or IL-8, apoptosis, and the like.

Such assays often involve monitoring the response of cells to the antibody, for example cell survival, cell death, change in cellular morphology, or transcriptional activation such as cellular expression of a natural gene or reporter gene. For some assays additional cells or components, that is in addition to the target cells, may need to be added, for example serum complement, or effector cells such as peripheral blood monocytes (PBMCs), NK cells, macrophages, and the like. Such additional cells may be from any organism, preferably humans, mice, rat, rabbit, and monkey.

Methods for monitoring cell death or viability are known in the art, and include the use of dyes, immunochemical, cytochemical, and radioactive reagents. For example, caspase staining assays may enable apoptosis to be measured, and uptake or release of radioactive substrates or fluorescent dyes such as alamar blue may enable cell growth or activation to be monitored.

Transcriptional activation may also serve as a method for assaying function in cell-based assays. In this case, response may be monitored by assaying for natural genes or immunoglobulins which may be upregulated, for example the release of certain interleukins may be measured, or alternatively the readout may be via a reporter construct. Cell-based assays may also involve the measure of morphological changes of cells as a response to the presence of an antibody described herein.

The antibody described herein preferably has a TNF-antagonistic activity only (in particular, without detectable agonistic activity), thus, reducing the inflammatory reaction caused by an increased TNF level in the circulation that could result in undesired inflammatory responses, apoptosis and necrosis, organ failure and septic shock. The preferred antibody has an antagonistic activity corresponding to an $IC_{50}$ of less than 100 nM, preferably less than 20 nM, more preferred less than 10 nM, most preferred in the single digit nanomolar range or less, as measured in a cell-based assay employing TNF or LTalpha at a half-maximal saturation concentration, preferably in the range of 0.01-0.1 nM TNF and LTalpha, respectively, e.g. by a test system as further described by the examples below.

A potential TNF-mimetic agonistic activity is preferably measured in the same cell-based assay, however, without employing TNF, e.g. by a test system as further described by the examples below. The antibody described herein preferably has no significant agonistic activity, if the incubation of HeLa or HT1080 cells in the absence of TNF results in no or only marginal induction of cytokine, e.g. elevated IL-6 or IL-8 levels of less than 0.5 ng/ml at concentrations of at least 5 nM or around 10 nM of the antibody. Preferably there is no or only marginal or negative cytokine production, which can be determined by the amount of less than 10 pg/$10^5$ cells. In a preferred example the cytokine expression and release is less than 2.5 pg/100.000 cells in 18 h. Preferably the agonistic activity is thus below the basal level, or less than 2% of the response of a comparable TNF concentration, preferably less than 1% of the equivalent or maximal TNF response.

The antibody described herein preferably has no significant agonistic activity, if the incubation of HeLa or HT1080 cells in the absence of TNF results in only marginal induction of cytokine of less than 2% of the response of a comparable TNF concentration, preferably less than 1% of the equivalent TNF response.

It has been particularly proven that an exemplary antibody described herein did not trigger the expression or release of inflammatory cytokines, such as IL-6 or IL-8. Thereby the undesired inflammatory conditions or tissue damage can be avoided, despite of high affinity to bind the TNFR1. The reduction of such side reactions is particularly useful for providing pharmaceutical preparations to treat chronic disease.

The term "substantially the same biological activity" as used herein refers to the activity as indicated by substantially the same activity being at least 20%, at least 50%, at least 75%, at least 90%, e.g. at least 100%, or at least 125%, or at least 150%, or at least 175%, or e.g. up to 200%, or even a higher activity as determined for the comparable or parent antibody.

The preferred antibody constructs as described herein are functionally active with regard to the huTNFR1 antigen binding, preferably which have a high affinity to bind the antigen with a $K_D$ of less than $5 \times 10^{-9}$ M, or less than $4 \times 10^{-9}$ M, or less than $3 \times 10^{-9}$ M, or less than $2 \times 10^{-9}$ M, or less than $10^{-9}$ M, or less than $10^{-10}$ M. Specifically, the tendency of dissociation is low, with $k_{off}$ of less than $10^{-3}$ s$^{-1}$, or less than $5 \times 10^{-4}$ s$^{-1}$ or less than $10^{-5}$ s$^{-1}$. Specifically, the tendency of association is high, with $k_{on}$ of at least $10^5$ M$^{-1}$s$^{-1}$, or $10^6$ M$^{-1}$s$^{-1}$. Preferred antibody variants are still specifically recognizing the huTNFR1 target, with a possible increase in affinity and/or lower dissociation and/or higher association to effectively bind the target and maintain the antigen-antibody interaction over a prolonged period of time. Still, differences in $K_D$, $k_{off}$, and/or $k_{on}$ values may be 1, 2, or 3 logs, e.g. obtained by affinity maturation of the antibody.

The binding affinity of an antibody is usually characterized in terms of the concentration of the antibody, at which half of the antigen binding sites are occupied, known as the dissociation constant (Kd, or $K_D$). Usually a binder is considered a high affinity binder with a $K_D<10^{-8}$ M, in some cases, e.g. for therapeutic purposes with higher affinities, e.g. with a $K_D<10^{-9}$ M, even more preferred is a $K_D<10^{-10}$ M.

Yet, in a particularly preferred embodiment the antigen binding affinity is of medium affinity, e.g. with a $K_D$ of less than $10^{-7}$. Medium affinity binders may be provided, and specifically be used to engineer an affinity-matured variant with the desired affinity properties, which can be used as an inhibitor described herein.

Affinity maturation is the process by which antibodies with increased affinity for a target antigen are produced. Any one or more methods of preparing and/or using affinity maturation libraries available in the art may be employed in order to generate affinity matured antibodies in accordance with various embodiments of the invention disclosed herein. Exemplary such affinity maturation methods and uses, such as random mutagenesis, bacterial mutator strains passaging, site-directed mutagenesis, mutational hotspots targeting, parsimonious mutagenesis, antibody shuffling, light chain shuffling, heavy chain shuffling, CDR1 and/or CDR1 mutagenesis, and methods of producing and using affinity maturation libraries amenable to implementing methods and uses in accordance with various embodiments of the invention disclosed herein, include, for example, those disclosed in: Wark & Hudson, 2006, Advanced Drug Delivery Reviews 58: 657-670.

With structural changes of an antibody, including amino acid mutagenesis or as a consequence of somatic mutation in immunoglobulin gene segments, variants of a binding site to an antigen are produced and selected for greater affinities. Affinity matured antibodies may exhibit a several logfold greater affinity than a parent antibody. Single parent antibodies may be subject to affinity maturation. Alternatively pools of antibodies with similar binding affinity to the target antigen may be considered as parent structures that are varied to obtain affinity matured single antibodies or affinity matured pools of such antibodies.

The preferred affinity matured variant of an antibody described herein exhibits at least a 2-fold increase in affinity of binding, preferably at least a 5-, preferably at least 10-, preferably at least 50-, or preferably at least 100-fold increase. The affinity maturation may be employed in the course of the selection campaigns employing respective libraries of parent molecules, either with antibodies having medium binding affinity to obtain the antibody described herein. Alternatively, the affinity may be even more increased by affinity maturation of the antibody described herein to obtain the high values corresponding to a $K_D$ of less than $10^{-10}$ M, or even less than $10^{-11}$ M.

In certain embodiments, binding affinity is determined by an affinity ELISA assay. In certain embodiments binding affinity is determined by a BIAcore, ForteBio or MSD assays. In certain embodiments binding affinity is determined by a kinetic method. In certain embodiments binding affinity is determined by an equilibrium/solution method. In certain embodiments binding affinity is determined by standard quartz crystal microbalance (QCM) measurements, in particular at predetermined conditions, which resemble the physiological conditions (about 37° C., density about 50 Hz).

The term "functionally active variant" also includes naturally-occurring allelic variants, as well as mutants or any other non-naturally occurring variants. As is known in the art, an allelic variant is an alternate form of a (poly) peptide that is characterized as having a substitution, deletion, or addition of one or more amino acids that does essentially not alter the biological function of the polypeptide.

Functionally active variants may be obtained by sequence alterations in the polypeptide or the nucleotide sequence, e.g. by one or more point mutations, wherein the sequence alterations retains or improves a function of the unaltered polypeptide or the nucleotide sequence, when used in combination of the invention. Such sequence alterations can include, but are not limited to, (conservative) substitutions, additions, deletions, mutations and insertions.

Specific functionally active variants are antibody constructs comprising CDR variants. A CDR variant includes an amino acid sequence modified by at least one amino acid in the CDR region, wherein said modification can be a chemical or a partial alteration of the amino acid sequence, which modification permits the variant to retain the biological characteristics of the unmodified sequence. A partial alteration of the CDR amino acid sequence may be by deletion or substitution of one to several amino acids, e.g. 1 or 2, or even more, up to 3, 4 or 5 amino acids, or by addition or insertion of one to several amino acids, e.g. 1 or 2, or even more, up to 3, 4 or 5 amino acids, or by a chemical derivatization of one to several amino acids, e.g. 1 or 2, or even more, up to 3, 4 or 5 amino acids, or combination thereof. The substitutions in amino acid residues may be conservative substitutions, for example, substituting one hydrophobic amino acid for an alternative hydrophobic amino acid.

Conservative substitutions are those that take place within a family of amino acids that are related in their side chains and chemical properties. Examples of such families are amino acids with basic side chains, with acidic side chains, with non-polar aliphatic side chains, with non-polar aromatic side chains, with uncharged polar side chains, with small side chains, with large side chains etc.

A point mutation is particularly understood as the engineering of a polynucleotide that results in the expression of an amino acid sequence that differs from the non-engineered amino acid sequence in the substitution or exchange, deletion or insertion of one or more single (non-consecutive) or doublets of amino acids for different amino acids.

Some point mutations in the framework region would increase the manufacturability, e.g. by improving its expression by a recombinant production host cell line. Some embodiments would also include point mutations in the framework region to improve the stability in vivo and/or in vitro, e.g. as determined by its thermostability. For example, the VH sequence may comprise one or more, several point mutations, which have proved to substantially increase the thermostabilty of the antibody. Thermostabilized variants are e.g. variants of an antibody construct comprising the VH and VL sequences of IZI06.1 (VH: SEQ ID 20, VL: SEQ ID 21), wherein the VH domain sequence is a variation of the (parent) IZI06.1 VH sequence (SEQ ID 20) and comprises any of the amino acids (Kabat numbering):

a) in FR1 at position 1: Q or H;
b) in CDRH2
  i) at position 3: Y or V;
  ii) at position 5: Y, T, or S;
  iii) at position 6: S or Q;
  iv) at position 8: H or E;
  v) at position 10: Y or K;
  vi) at position 13: E or D.

A further preferred variation concerns the VL sequence (SEQ ID 21) and comprises the S91G point mutation in the CDRL3 (position 3).

Alternative germline sequences may be used for humanization purposes, which can lead to further FR variants comprising a limited number of point mutations and which variants would again have an increased thermostability.

An exemplary assay for determining the thermostability is provided in the examples section below.

Preferred point mutations refer to the exchange of amino acids of the same polarity and/or charge. In this regard, amino acids refer to twenty naturally occurring amino acids encoded by sixty-four triplet codons. These 20 amino acids can be split into those that have neutral charges, positive charges, and negative charges:

The "neutral" amino acids are shown below along with their respective three-letter and single-letter code and polarity:

Alanine: (Ala, A) nonpolar, neutral;
Asparagine: (Asn, N) polar, neutral;
Cysteine: (Cys, C) nonpolar, neutral;
Glutamine: (Gln, Q) polar, neutral;
Glycine: (Gly, G) nonpolar, neutral;
Isoleucine: (Ile, I) nonpolar, neutral;
Leucine: (Leu, L) nonpolar, neutral;
Methionine: (Met, M) nonpolar, neutral;
Phenylalanine: (Phe, F) nonpolar, neutral;
Proline: (Pro, P) nonpolar, neutral;
Serine: (Ser, S) polar, neutral;
Threonine: (Thr, T) polar, neutral;
Tryptophan: (Trp, W) nonpolar, neutral;
Tyrosine: (Tyr, Y) polar, neutral;
Valine: (Val, V) nonpolar, neutral; and
Histidine: (His, H) polar, positive (10%) neutral (90%).
The "positively" charged amino acids are:
Arginine: (Arg, R) polar, positive; and
Lysine: (Lys, K) polar, positive.
The "negatively" charged amino acids are:
Aspartic acid: (Asp, D) polar, negative; and
Glutamic acid: (Glu, E) polar, negative.

"Percent (%) amino acid sequence identity" with respect to the antibody sequences and homologs described herein is defined as the percentage of amino acid residues in a candidate sequence that are identical with the amino acid residues in the specific polypeptide sequence, after aligning the sequence and introducing gaps, if necessary, to achieve the maximum percent sequence identity, and not considering any conservative substitutions as part of the sequence identity. Those skilled in the art can determine appropriate parameters for measuring alignment, including any algorithms needed to achieve maximal alignment over the full length of the sequences being compared.

An antibody variant is specifically understood to include homologs, analogs, fragments, modifications or variants with a specific glycosylation pattern, e.g. produced by glycoengineering, which are functional and may serve as functional equivalents, e.g. binding to the specific targets and with functional properties.

An antibody described herein may or may not exhibit Fc effector function. Though the mode of action is mainly mediated by neutralizing antibodies without Fc effector functions, Fc can recruit complement and aid elimination of the target antigen, such as a toxin, from the circulation via formation of immune complexes.

Specific antibodies may be devoid of an active Fc moiety, thus, either composed of antibody domains that do not contain an Fc part of an antibody or that do not contain an Fcgamma receptor binding site, or comprising antibody domains lacking Fc effector function, e.g. by modifications to reduce Fc effector functions, in particular to abrogate or reduce ADCC and/or CDC activity. Alternative antibodies may be engineered to incorporate modifications to increase Fc effector functions, in particular to enhance ADCC and/or CDC activity.

The term "Fc fragment" or "Fc region" as used herein shall specifically include those mutants or functionally active variants with deficient Fc receptor-binding properties, e.g. glycoengineered Fc regions or those with downmodulated effector function and/or prolonged half-life.

The term "effector function" as used herein shall mean the effect mediated by an effector ligand binding to the Fc region of an antibody. Exemplary effector ligands are Fc receptors or Fc receptor-like molecules binding to immunoglobulins. An Fc receptor is a protein found on the surface of certain cells—including natural killer cells, macrophages, neutrophils, and mast cells—that contribute to the protective functions of the immune system. There are several different types of Fc receptors, which are classified based on the type of antibody that they recognize; those that bind the most common class of antibody, IgG, are called Fc-gamma receptors (FcγR or FcgR). The family of FcγRs includes several members: FcγRI (CD64), FcγRIIA (CD32a), FcγRIIB (CD32b), FcγRIIIA (CD16a), FcγRIIIB (CD16b). Among the effector molecules there are also complement proteins, such as C1q.

Another Fc receptor, the neonatal Fc receptor (FcRn) also binds IgG and is involved in preservation and half-life of this antibody. According to the invention it is preferred that the function mediated by FcRn is not downmodulated.

The term "downmodulate" shall refer to the reduction of an effect mediated by a gene or a group of genes, or a polypeptide, by gene mutation or downregulation of the gene expression or activity of gene expression products, such as nucleic acids or polypeptides, specifically by reduction of binding properties, like affinity, avidity or specificity, including inhibition of binding a ligand, such as an effector ligand, at least in part. Thereby an antibody exhibiting a reduced ADCC and/or CDC can be obtained.

Antibody-dependent cell-mediated cytotoxicity (ADCC) is the killing of antibody-coated target cells by cells with Fc receptors that recognize the constant region of the bound antibody. Most ADCC is mediated by NK cells that have the Fc receptor FcγRIII or CD16 on their surface. Typical assays employ target cells, like Ramos cells, incubated with serially diluted antibody prior to the addition of freshly isolated effector cells. The ADCC assay is then further incubated for several hours and % cytotoxicity detected. Usually the Target: Effector ratio is about 1:16, but may be 1:1 up to 1:50.

Complement-dependent cytotoxicity (CDC) is a mechanism of killing cells in which antibody bound to the target cell surface fixes complement, which results in assembly of the membrane attack complex that punches holes in the target cell membrane resulting in subsequent cell lysis. The commonly used CDC assay follows the same procedure as for ADCC determination, however, with complement containing serum instead of effector cells.

The antibody described herein has an Fc region deficient in mediating effector functions, preferably a downmodulated cytotoxic activity as determined by either of ADCC and CDC assay, preferably in a way to provide a significant decrease in the percentage of cytolysis as compared to a control. The absolute percentage decrease preferably is higher than 10%, more preferably higher than 20%, even more preferred higher than 30%, 40%, 50%, 60%, 70%, 80%, 90%. Most preferred the antibody is essentially free of at least one of ADCC or CDC activity, e.g. having less than 10% of the typical ADCC and/or CDC activity as compared to a native (unmodified) antibody. The term "essentially free" as used herein shall also refer to those antibody variants that are completely lacking such an activity as measured in a standard assay.

Specific point mutations within the Fc region are well-known in the art to effectively downmodulate the effector function. Specifically preferred mutations are employed in the region of the binding site on human IgG for the different Fcgamma receptors (FcgR), which would provide for abrogating immune recruitment via FcgR. The binding site on human and murine IgG for FcgR was mapped primarily to the lower hinge region composed of IgG residues 233-239. Additional broad segments, e.g. Gly316-Lys338 were determined for human FcγRI, Lys274-Arg301 and Tyr407-Arg416 for human FcγRIII. The 3.2-Å crystal structure of the human IgG1 Fc fragment with human FcgammaRIIIA delineated IgG1 residues Leu234-Ser239, Asp265-Glu269, Asn297-Thr299, and Ala327-Ile332 as involved in binding to FcγRIIIA. A review referring to high resolution mapping of human IgG1 for human FcγR receptors (FcγRI, FcγRIIA, FcγRIIB, and FcγRIIIA) is provided by Shields et al. 2001, J. Biol. Chem. 276:6591-604).

The antibody or Fc region may be glycosylated or not, depending on specific mutations or the choice of expression system, or glycoengineered to obtain a specific glyosylation pattern.

The term "glycoengineered" with respect to antibody sequences or Fc region shall refer to glycosylation variants having modified ADCC and/or CDC as a result of the glycoengineering. All antibodies contain carbohydrate structures at conserved positions in the heavy chain constant regions, with each isotype possessing a distinct array of N-linked carbohydrate structures, which variably affect protein assembly, secretion or functional activity. IgG1 type antibodies are glycoproteins that have a conserved N linked glycosylation site at Asn297 in each CH2 domain. The two complex bi-antennary oligosaccharides attached to Asn297 are buried between the CH2 domains, forming extensive contacts with the polypeptide backbone, and their presence is essential for the antibody to mediate effector functions such as antibody dependent cellular cytotoxicity (ADCC) (Lifely et al., 1995, Glycobiology 5: 813-822). Removal of N-Glycan at N297, eg through mutating N297, e.g. to A, or T299 typically results in aglycosylated Fc with reduced ADCC.

Major differences in antibody glycosylation occur between cell lines, and even minor differences are seen for a given cell line grown under different culture conditions. Expression in bacterial cells typically provides for an aglycosylated antibody that is essentially free of ADCC and/or CDC activity. CHO cells with tetracycline-regulated expression of β(1,4)-N-acetylglucosaminyltransferase III (GnTIII), a glycosyltransferase catalyzing formation of bisecting GlcNAc, was reported to have improved ADCC activity (Umana et al., 1999, Nature Biotech. 17:176-180). In addition to the choice of host cells, factors that affect glycosylation during recombinant production of antibodies include growth mode, media formulation, culture density, oxygenation, pH, purification schemes and the like.

The term "antigen-binding site" or "binding site" refers to the part of an antibody that participates in antigen binding. The antigen binding site is formed by amino acid residues of the N-terminal variable ("V") regions of the heavy ("H")

and/or light ("L") chains, or the variable domains thereof. Three highly divergent stretches within the V regions of the heavy and light chains, referred to as "hypervariable regions", are inter-posed between more conserved flanking stretches known as framework regions, The antigen-binding site provides for a surface that is complementary to the three-dimensional surface of a bound epitope or antigen, and the hypervariable regions are referred to as "complementarity-determining regions", or "CDRs." The binding site incorporated in the CDRs is herein also called "CDR binding site".

The term "antigen" as used herein is interchangeably with the terms "target" or "target antigen" shall refer to a whole target molecule or a fragment of such molecule recognized by an antibody binding site. Specifically, substructures of an antigen, e.g. a polypeptide or carbohydrate structure, generally referred to as "epitopes", e.g. B-cell epitopes or T-cell epitope, which are immunologically relevant, may be recognized by such binding site. The huTNFR1 antigen is an antigen comprising receptor structures which is capable to specifically bind trimeric TNF or LTα as a mono- or multimeric cytokine receptor on the surface of most human cells.

The term "huTNFR1" as used herein shall refer to CD120a TNFR1 (p55/60, TNFRSF1A tumor necrosis factor receptor superfamily, member 1A [*Homo sapiens* (human)], Gene ID: 7132) receptor of TNF, expressed ubiquitously on most human cells The term "epitope" as used herein shall in particular refer to a molecular structure which may completely make up a specific binding partner or be part of a specific binding partner to a binding site of an antibody. An epitope may either be composed of a carbohydrate, a peptidic structure, a fatty acid, an organic, biochemical or inorganic substance or derivatives thereof and any combinations thereof. If an epitope is comprised in a peptidic structure, such as a peptide, a polypeptide or a protein, it will usually include at least 3 amino acids, preferably 5 to 40 amino acids, and more preferably between about 10-20 amino acids. Epitopes can be either linear or conformational epitopes. A linear epitope is comprised of a single segment of a primary sequence of a polypeptide or carbohydrate chain. Linear epitopes can be contiguous or overlapping.

Conformational epitopes are comprised of amino acids or carbohydrates brought together by folding the polypeptide to form a tertiary structure and the amino acids are not necessarily adjacent to one another in the linear sequence. Specifically and with regard to polypeptide antigens a conformational or discontinuous epitope is characterized by the presence of two or more discrete amino acid residues, separated in the primary sequence, but assembling to a consistent structure on the surface of the molecule when the polypeptide folds into the native protein/antigen.

Herein the term "epitope" shall particularly refer to the epitope recognized by ATROSAB, which is an epitope that comprises or consists essentially of at least the membrane-distal CRD1 and subdomain A1 of CDR2 of huTNFR1.

The term "expression" is understood in the following way. Nucleic acid molecules containing a desired coding sequence of an expression product such as e.g. an antibody as described herein, and control sequences such as e.g. a promoter in operable linkage, may be used for expression purposes. Hosts transformed or transfected with these sequences are capable of producing the encoded proteins. In order to effect transformation, the expression system may be included in a vector; however, the relevant DNA may also be integrated into the host chromosome. Specifically the term refers to a host cell and compatible vector under suitable conditions, e.g. for the expression of a protein coded for by foreign DNA carried by the vector and introduced to the host cell.

Coding DNA is a DNA sequence that encodes a particular amino acid sequence for a particular polypeptide or protein such as e.g. an antibody. Promoter DNA is a DNA sequence which initiates, regulates, or otherwise mediates or controls the expression of the coding DNA. Promoter DNA and coding DNA may be from the same gene or from different genes, and may be from the same or different organisms.

Recombinant cloning vectors will often include one or more replication systems for cloning or expression, one or more markers for selection in the host, e.g. antibiotic resistance, and one or more expression cassettes.

"Vectors" used herein are defined as DNA sequences that are required for the transcription of cloned recombinant nucleotide sequences, i.e. of recombinant genes and the translation of their mRNA in a suitable host organism.

An "expression cassette" refers to a DNA coding sequence or segment of DNA that code for an expression product that can be inserted into a vector at defined restriction sites. The cassette restriction sites are designed to ensure insertion of the cassette in the proper reading frame. Generally, foreign DNA is inserted at one or more restriction sites of the vector DNA, and then is carried by the vector into a host cell along with the transmissible vector DNA. A segment or sequence of DNA having inserted or added DNA, such as an expression vector, can also be called a "DNA construct".

Expression vectors comprise the expression cassette and additionally usually comprise an origin for autonomous replication in the host cells or a genome integration site, one or more selectable markers (e.g. an amino acid synthesis gene or a gene conferring resistance to antibiotics such as zeocin, kanamycin, G418 or hygromycin), a number of restriction enzyme cleavage sites, a suitable promoter sequence and a transcription terminator, which components are operably linked together. The term "vector" as used herein includes autonomously replicating nucleotide sequences as well as genome integrating nucleotide sequences. A common type of vector is a "plasmid", which generally is a self-contained molecule of double-stranded DNA that can readily accept additional (foreign) DNA and which can readily be introduced into a suitable host cell. A plasmid vector often contains coding DNA and promoter DNA and has one or more restriction sites suitable for inserting foreign DNA. Specifically, the term "vector" or "plasmid" refers to a vehicle by which a DNA or RNA sequence (e.g. a foreign gene) can be introduced into a host cell, so as to transform the host and promote expression (e.g. transcription and translation) of the introduced sequence.

The term "host cell" as used herein shall refer to primary subject cells transformed to produce a particular recombinant protein, such as an antibody as described herein, and any progeny thereof. It should be understood that not all progeny are exactly identical to the parental cell (due to deliberate or inadvertent mutations or differences in environment), however, such altered progeny are included in these terms, so long as the progeny retain the same functionality as that of the originally transformed cell. The term "host cell line" refers to a cell line of host cells as used for expressing a recombinant gene to produce recombinant polypeptides such as recombinant antibodies. The term "cell line" as used herein refers to an established clone of a particular cell type that has acquired the ability to proliferate over a prolonged period of time. Such host cell or host cell line may be maintained in cell culture and/or cultivated to produce a recombinant polypeptide.

The term "isolated" or "isolation" as used herein with respect to a nucleic acid, an antibody or other compound shall refer to such compound that has been sufficiently separated from the environment with which it would naturally be associated, so as to exist in "substantially pure" form. "Isolated" does not necessarily mean the exclusion of artificial or synthetic mixtures with other compounds or materials, or the presence of impurities that do not interfere with the fundamental activity, and that may be present, for example, due to incomplete purification. In particular, isolated nucleic acid molecules of the present invention are also meant to include those which are not naturally occurring, e.g. codon-optimized nucleic acids or cDNA, or chemically synthesized.

Likewise, the isolated antibody as further described herein is specifically non-naturally occurring, e.g. as provided in a combination preparation with another antibody or active agent, which combination does not occur in nature, or as a derivative or variant of a naturally-occurring antibody, or an optimized or affinity-matured variant of a naturally-occurring antibody, or an antibody with a framework-region which is engineered to improve the stability of the antibody. By such optimizing or engineering the antibody comprises one or more synthetic structures or sequences or characteristics, which would not be found in the context of the antibody in nature.

With reference to nucleic acids described herein, the term "isolated nucleic acid" is sometimes used. This term, when applied to DNA, refers to a DNA molecule that is separated from sequences with which it is immediately contiguous in the naturally-occurring genome of the organism in which it originated. For example, an "isolated nucleic acid" may comprise a DNA molecule inserted into a vector, such as a plasmid or virus vector, or integrated into the genomic DNA of a prokaryotic or eukaryotic cell or host organism. When applied to RNA, the term "isolated nucleic acid" refers primarily to an RNA molecule encoded by an isolated DNA molecule as defined above. Alternatively, the term may refer to an RNA molecule that has been sufficiently separated from other nucleic acids with which it would be associated in its natural state (i.e., in cells or tissues). An "isolated nucleic acid" (either DNA or RNA) may further represent a molecule produced directly by biological or synthetic means and separated from other components present during its production.

With reference to polypeptides or proteins, such as isolated antibodies described herein, the term "isolated" shall specifically refer to compounds that are free or substantially free of material with which they are naturally associated such as other compounds with which they are found in their natural environment, or the environment in which they are prepared (e g. cell culture) when such preparation is by recombinant DNA technology practiced in vitro or in vivo. Isolated compounds can be formulated with diluents or adjuvants and still for practical purposes be isolated—for example, the polypeptides or polynucleotides can be mixed with pharmaceutically acceptable carriers or excipients when used in diagnosis or therapy.

The term "recombinant" as used herein shall mean "being prepared by or the result of genetic engineering". A recombinant host specifically comprises an expression vector or cloning vector, or it has been genetically engineered to contain a recombinant nucleic acid sequence, in particular employing nucleotide sequence foreign to the host. A recombinant protein is produced by expressing a respective recombinant nucleic acid in a host.

The antibody construct further described herein may be a recombinant antibody. To this end, the term "recombinant antibody", as used herein, includes antibodies that are prepared, expressed, created or isolated by recombinant means, such as (a) antibodies isolated from an animal (e.g., a mouse) that is transgenic or transchromosomal for human immunoglobulin genes or a hybridoma prepared therefrom, (b) antibodies isolated from a host cell transformed to express the antibody, e.g., from a transfectoma, (c) antibodies isolated from a recombinant, combinatorial human antibody library or library of antigen-binding sequences of an antibody, and (d) antibodies prepared, expressed, created or isolated by any other means that involve splicing of human immunoglobulin gene sequences to other DNA sequences. Such recombinant antibodies comprise antibodies engineered to include rearrangements and mutations which occur, for example, during antibody maturation. In accordance with the present invention there may be employed conventional molecular biology, microbiology, and recombinant DNA techniques within the skill of the art. Such techniques are explained fully in the literature. See, e.g., Maniatis, Fritsch & Sambrook, "Molecular Cloning: A Laboratory Manual, Cold Spring Harbor, (1982).

The antibody described herein is preferably provided as a recombinant protein produced by a recombinant expression system employing a host cell, e.g. by expression in the periplasmic space of *E. coli* or by expression as a secreted protein in a eukaryotic expression system such as yeast or mammalian, e.g. by CHO, HEK or human production host cell lines.

Chinese hamster ovary (CHO) cells have been most commonly used for antibody production. In addition to providing suitable glycosylation patterns, these cells allow consistent generation of genetically stable, highly productive clonal cell lines. They can be cultured to high densities in simple bioreactors using serum free media, and permit the development of safe and reproducible bioprocesses.

Host cells are most preferred, when being established, adapted, and completely cultivated under serum free conditions, and optionally in media which are free of any protein/peptide of animal origin.

"Specific" binding, recognizing or targeting as used herein, means that the binder, e.g., antibody or antigen-binding moiety, exhibits appreciable affinity for the target antigen or a respective epitope in a heterogeneous population of molecules. Thus, under designated conditions (e.g., immunoassay), a binder specifically binds to the target antigen and does not bind in a significant amount to other molecules present in a sample. The specific binding means that binding is selective in terms of target identity, high, medium or low binding affinity or avidity, as selected. Selective binding is usually achieved if the binding constant or binding dynamics is at least 10-fold different (understood as at least 1 log difference), preferably the difference is at least 100-fold (understood as at least 2 logs difference), and more preferred a least 1000-fold (understood as at least 3 logs difference) as compared to another target. Differential binding may be determined by an immunoassay, preferably immunoblotting, ELISA or other immunological methods. The specificity of an antibody molecule for a particular target can be determined by competition assays, e.g. as described in Harlow, et al., ANTIBODIES: A LABORATORY MANUAL, Cold Spring Harbor Laboratory Press, Cold Spring Harbor, N.Y., 1988). Selective binding can be engineered or improved by recombinant antibody optimization methods known in the art. For example, certain regions of the variable regions of the immunoglobulin chains described herein may be subjected to one or more optimization strategies, including light chain shuffling, destinational mutagenesis, CDR amalgamation, and directed mutagenesis of selected CDR and/or framework regions.

The inhibitor described herein is specifically comprising an antibody which has the same specificity, or the same antigen-binding site as determined by the specific CDR sequences (SEQ ID 1-6 or functional CDR variants thereof) to bind the TNFR1 target, or binding the same epitope or overlapping epitopes as the H398 or ATROSAB.

Use of the term "having the same specificity", "having the same binding site" or "binding the same epitope" indicates that equivalent monoclonal antibodies exhibit the same or essentially the same, i.e. similar immunoreaction (binding) characteristics and compete for binding to a pre-selected target binding sequence. The relative specificity of an antibody molecule for a particular target can be relatively determined by competition assays, e.g. as described in Harlow, et al., ANTIBODIES: A LABORATORY MANUAL, Cold Spring Harbor Laboratory Press, Cold Spring Harbor, N.Y., 1988).

Competition herein means a greater relative inhibition than about 30% as determined by competition ELISA analysis or by ForteBio analysis. It may be desirable to set a higher threshold of relative inhibition as criteria of what is a suitable level of competition in a particular context, e.g., where the competition analysis is used to select or screen for new antibodies designed with the intended function of the binding of the antigen. Thus, for example, it is possible to set criteria for the competitive binding, wherein at least 40% relative inhibition is detected, or at least 50%, at least 60%, at least 70%, at least 80%, at least 90% or even at least 100%, before an antibody is considered sufficiently competitive.

The term "subject" as used herein shall refer to a warm-blooded mammalian, particularly a human being or a non-human animal. In particular the medical use described herein or the respective method of treatment applies to a subject in need of prophylaxis or treatment of a disease condition associated with inflammation. The subject may be a patient at risk of or suffering from inflammatory disease, including early stage or late stage disease. The term "patient" includes human and other mammalian subjects that receive either prophylactic or therapeutic treatment. The term "treatment" is thus meant to include both prophylactic and therapeutic treatment.

A subject is e.g. treated for prophylaxis or therapy of inflammatory disease conditions. In particular, the subject is treated, which is either at risk of acute or chronic inflammatory disease or developing such disease or disease recurrence, or a subject that is suffering from such inflammatory disease.

Specifically, the term "therapy" refers to therapeutic measures which are intended to encompass administration to cure the disease or reduce the symptoms of disease.

Specifically, the term "prophylaxis" refers to preventive measures which are intended to reduce the risk of disease occurrency, or recurrence of disease.

The inhibitor described herein may specifically regulate cell survival by inhibiting TNF-TNFR1 interaction, preventing the activation of signalling pathways downstream of the TNFR, thereby minimizing the pro-inflammatory programme it would initiate in immune cells and decreasing the pathology of autoimmune and inflammatory diseases. Using the inhibitor to prevent the TNFR1 interaction with its TNF ligand would decrease the expansion and survival of pathogenic cell populations and decrease the production of pro-inflammatory cytokines and ameliorate TNF-mediated inflammation. In the context of autoimmune disease, the TNF-TNFR interactions occur mainly during an immune response. The functions of specific immune-cell types are controlled by the TNF-TNFR interactions, and may be regulated by the inhibitor as described herein.

Among the inflammatory diseases there are the indications of an anti-TNF therapeutic. Thus, the inhibitor or antibody described herein is used as an alternative to conventional anti-TNF therapeutics.

Specifically, the pharmaceutical composition described herein is suitable for treating any of the following diseases or inflammatory conditions (or inflammatory disease) associated therewith, which diseases are selected from the group consisting of autoimmune diseases, rheumatoid arthritis, psoriasis, psoriatic arthritis, juvenile arthritis, ankylosing spondylitis, Crohn's disease (Morbus Crohn), multiple sclerosis, congestive heart failure, metabolic disease, cytokine release syndrome, septic shock, acute and chronic neurodegenerative disease, including stroke, Alzheimer and Parkinson disease. Further appropriate indications include colitis ulcerosa, pancreatitis, COPD, and other chronic inflammatory and/or autoimmune diseases, acute fulminant viral or bacterial infections, metabolic diseases, chronic neurodegenerative diseases, genetically inherited diseases with TNF/TNFR1 as the causative pathologic mediator, preferably selected from periodic fever syndrome and Cherubism, and cancer.

The term "therapeutically effective amount", used herein interchangeably with any of the terms "effective amount" or "sufficient amount" of a compound, e.g. an antibody described herein, is a quantity or activity sufficient to, when administered to the subject effect beneficial or desired results, including clinical results, and, as such, an effective amount or synonym thereof depends upon the context in which it is being applied.

An effective amount is intended to mean that amount of a compound that is sufficient to treat, prevent or inhibit such diseases or disorder. In the context of disease, therapeutically effective amounts of the antibody as described herein are specifically used to treat, modulate, attenuate, reverse, or affect a disease or condition that benefits from an inhibition of the TNF-TNFR1 interaction.

The amount of the compound that will correspond to such an effective amount will vary depending on various factors, such as the given drug or compound, the pharmaceutical formulation, the route of administration, the type of disease or disorder, the identity of the subject or host being treated, and the like, but can nevertheless be routinely determined by one skilled in the art.

A preferred pharmaceutical composition described herein comprises a therapeutically effective amount of the huTNFR1 antibody as defined above and optionally one or more additional components selected from the group consisting of a pharmaceutically acceptable carrier, pharmaceutically acceptable salts, an auxiliary agent, a stabilizer, a diluent and a solvent, or any combination thereof.

According to the invention a method of treating a patient comprises the step of administering a therapeutically effective amount of the above-defined huTNFR1-antibody to a patient in need thereof. A therapeutically effective amount typically is in the range of 0.5-500 mg, preferably 1-400 mg, even more preferred up to 300 mg, up to 200 mg, up to 100 mg or up to 10 mg, though higher doses may be indicated e.g. for treating acute disease conditions.

In one embodiment, an antibody described herein is the only therapeutically active agent administered to a patient. Alternatively, the antibody described herein is administered in combination with one or more other therapeutic agents, including but not limited to TNF antagonists, anti-inflammatory agents, cytokines, growth factors, or other therapeutic agents. The TNFR1-antagonistic antibody may be administered concomitantly or consecutively with one or more other therapeutic regimens, preferably with anti-TNF therapeutics, such as anti-TNF antibodies. The antibody described herein is preferably administered to the patient as a first-line treatment, or as a second-line therapy where anti-TNF therapeutics were not efficient, either as acute or chronic treatment. The specifically preferred medical use is for treating chronic disease.

Moreover, a treatment or prevention regime of a subject with a therapeutically effective amount of the antibody described herein may consist of a single administration, or alternatively comprise a series of applications. For example, the antibody may be administered at least once a year, at least once a half-year or at least once a month. However, in another embodiment, the antibody may be administered to the subject from about one time per week to about a daily administration for a given treatment. The length of the treatment period depends on a variety of factors, such as the severity of the disease, either acute or chronic disease, the age of the patient, the concentration and the activity of the antibody format. It will also be appreciated that the effective dosage used for the treatment or prophylaxis may increase or decrease over the course of a particular treatment or prophylaxis regime. Changes in dosage may result and become apparent by standard diagnostic assays known in the art. In some instances, chronic administration may be required.

Once antibodies with the desired binding properties are identified, such antibodies, including antibody fragments can be produced by methods well-known in the art, including, for example, hybridoma techniques or recombinant DNA technology.

Recombinant monoclonal antibodies can, for example, be produced by isolating the DNA encoding the required antibody chains and transfecting a recombinant host cell with the coding sequences for expression, using well known recombinant expression vectors, e.g. the plasmids described herein or expression cassette(s) comprising the nucleotide sequences encoding the antibody sequences. Recombinant host cells can be prokaryotic and eukaryotic cells, such as those described above.

According to a specific aspect, the nucleotide sequence may be used for genetic manipulation to humanize the antibody or to improve the affinity, or other characteristics of the antibody. For example, the constant region may be engineered to more nearly resemble human constant regions to avoid immune response, if the antibody is used in clinical trials and treatments in humans. It may be desirable to genetically manipulate the antibody sequence to obtain greater affinity to the target. It will be apparent to one of skill in the art that one or more polynucleotide changes can be made to the antibody and still maintain its binding ability to the target antigen.

The production of antibody molecules, by various means, is generally well understood. U.S. Pat. No. 6,331,415 (Cabilly et al.), for example, describes a method for the recombinant production of antibodies where the heavy and light chains are expressed simultaneously from a single vector or from two separate vectors in a single cell. Wibbenmeyer et al. (1999, Biochim Biophys Acta 1430:191-202) and Lee and Kwak (2003, J. Biotechnology 101:189-198) describe the production of monoclonal antibodies from separately produced heavy and light chains, using plasmids expressed in separate cultures of host cells. Various other techniques relevant to the production of antibodies are provided in, e.g., Harlow, et al., ANTIBODIES: A LABORATORY MANUAL, Cold Spring Harbor Laboratory Press, Cold Spring Harbor, N.Y., (1988).

According to a specific aspect, the antibody described herein may be sequenced and the polynucleotide sequence may then be cloned into a vector for expression or propagation. The sequence encoding the antibody may be maintained in vector in a host cell and the host cell can then be expanded and frozen for future use. Production of recombinant monoclonal antibodies in cell culture can be carried out through cloning of antibody genes from B cells by means known in the art.

In another aspect, the invention provides an isolated nucleic acid comprising a coding sequence for production of a recombinant antibody described herein.

An antibody encoding nucleic acid can have any suitable characteristics and comprise any suitable features or combinations thereof. Thus, for example, an antibody-encoding nucleic acid, in the form of DNA, RNA, or a hybrid thereof, and may include non-naturally-occurring bases and a modified backbone, e.g., a phosphorothioate backbone that promotes stability of the nucleic acid, or both. Preferably the nucleic acid may be a codon-optimized sequence. The nucleic acid advantageously may be incorporated in an expression cassette, vector or plasmid described herein, comprising features that promote desired expression, replication, and/or selection in target host cell(s). Examples of such features include an origin of replication component, a selection gene component, a promoter component, an enhancer element component, a polyadenylation sequence component, a termination component, and the like, numerous suitable examples of which are known.

The present disclosure further provides the recombinant DNA constructs comprising one or more of the nucleotide sequences described herein. These recombinant constructs are used in connection with a vector, such as a plasmid, phagemid, phage or viral vector, into which a DNA molecule encoding any disclosed antibody is inserted.

Monoclonal antibodies are produced using any method that produces antibody molecules by cell lines in culture, e.g. cultivating recombinant eukaryotic (mammalian or insect) or prokaryotic (bacterial) host cells. Examples of suitable methods for preparing monoclonal antibodies include the hybridoma methods of Köhler & Milstein (1975, Nature 256:495-497) and the human B-cell hybridoma method (Kozbor, 1984, J. Immunol. 133:3001; and Brodeur et al., 1987, Monoclonal Antibody Production Techniques and Applications, (Marcel Dekker, Inc., New York), pp. 51-63).

Antibodies described herein may be identified or obtained employing a hybridoma method. In such method, a mouse or other appropriate host animal, such as a hamster, is immunized to elicit lymphocytes that produce or are capable of producing antibodies that will specifically bind to the protein used for immunization. Alternatively, lymphocytes may be immunized in vitro. Lymphocytes then are fused with myeloma cells using a suitable fusing agent, such as polyethylene glycol, to form a hybridoma cell.

Culture medium in which hybridoma cells are growing is assayed for production of monoclonal antibodies directed against the antigen. Preferably, the binding specificity of monoclonal antibodies produced by hybridoma cells is determined by immunoprecipitation or by an in vitro binding assay, such as radioimmunoassay (RIA) or enzyme-linked immunoabsorbent assay (ELISA).

Monoclonal antibodies (mAbs) may then be purified from hybridoma supernatants for further testing for its specific binding of the target antigen, and engineering of antibodies, e.g. for different diagnostic or therapeutic purposes.

huTNFR1-specific antibodies, in some instances, emerge through screening against the huTNFR1 antigen. To increase the likelihood of isolating differentially binding clones one would apply multiple selective pressures by processively screening against different antigens or epitopes.

Screening methods for identifying antibodies with the desired selective binding properties may be done by display technologies using a library displaying antibody sequences or antigen-binding sequences thereof (e.g. using phage, bacterial, yeast or mammalian cells; or in vitro display systems translating nucleic acid information into respective (poly)peptides). Reactivity can be assessed based on ELISA, Western blotting or surface staining with flow cytometry, e.g. using standard assays.

Isolated antigen(s) may e.g. be used for selecting antibodies from an antibody library, e.g. a phage-, phagemid- or yeast-displayed antibody library.

The invention moreover provides pharmaceutical compositions which comprise an inhibitor or antibody as described herein and a pharmaceutically acceptable carrier or excipient. These pharmaceutical compositions can be administered in accordance with the present invention as a bolus injection or infusion or by continuous infusion. Pharmaceutical carriers suitable for facilitating such means of administration are well-known in the art.

Pharmaceutically acceptable carriers generally include any and all suitable solvents, dispersion media, coatings, antibacterial and antifungal agents, isotonic and absorption delaying agents, and the like that are physiologically compatible with an antibody or related composition or combination described herein. Further examples of pharmaceutically acceptable carriers include sterile water, saline, phosphate buffered saline, dextrose, glycerol, ethanol, and the like, as well as combinations of any thereof.

In one such aspect, an antibody can be combined with one or more carriers appropriate a desired route of administration, antibodies may be, e.g. admixed with any of lactose, sucrose, starch, cellulose esters of alkanoic acids, stearic acid, talc, magnesium stearate, magnesium oxide, sodium and calcium salts of phosphoric and sulphuric acids, acacia, gelatin, sodium alginate, polyvinylpyrrolidine, polyvinyl alcohol, and optionally further tableted or encapsulated for conventional administration. Alternatively, an antibody may be dissolved in saline, water, polyethylene glycol, propylene glycol, carboxymethyl cellulose colloidal solutions, ethanol, corn oil, peanut oil, cotton-seed oil, sesame oil, tragacanth gum, and/or various buffers. Other carriers, adjuvants, and modes of administration are well known in the pharmaceutical arts. A carrier may include a controlled release material or time delay material, such as glyceryl monostearate or glyceryl distearate alone or with a wax, or other materials well known in the art.

Additional pharmaceutically acceptable carriers are known in the art and described in, e.g. REMINGTON'S PHARMACEUTICAL SCIENCES. Liquid formulations can be solutions, emulsions or suspensions and can include excipients such as suspending agents, solubilizers, surfactants, preservatives, and chelating agents.

Pharmaceutical compositions are contemplated wherein the inhibitor or antibody described herein and one or more therapeutically active agents are formulated. Stable formulations of the antibody described herein are prepared for storage by mixing said antibody having the desired degree of purity with optional pharmaceutically acceptable carriers, excipients or stabilisers, in the form of lyophilized formulations or aqueous solutions. The formulations to be used for in vivo administration are sterile. This is readily accomplished by filtration through sterile filtration membranes or other methods. The antibody and other therapeutically active agents disclosed herein may also be formulated as immunoliposomes, and/or entrapped in microcapsules.

Administration of the pharmaceutical composition comprising an inhibitor or antibody described herein, may be done in a variety of ways, including orally, subcutaneously, intravenously, intranasally, intraotically, transdermally, mucosal, topically, e.g., gels, salves, lotions, creams, etc., intraperitoneally, intramuscularly, intrapulmonary, e.g. employing inhalable technology or pulmonary delivery systems, vaginally, parenterally, rectally, or intraocularly.

Exemplary formulations as used for parenteral administration include those suitable for subcutaneous, intramuscular or intravenous injection as, for example, a sterile solution, emulsion or suspension.

In one embodiment, the antibody described herein is the only therapeutically active agent administered to a subject, e.g. as a disease modifying or preventing monotherapy.

In another embodiment, the antibody described herein is combined with further active substances, e.g. in a mixture or kit of parts, to treat a subject in need of therapy or prophylaxis, such as a disease modifying or preventing combination therapy.

The combination with one or more other therapeutic or prophylactic agents, may include standard treatment, e.g. antibiotics, steroid and non-steroid inhibitors of inflammation, e.g. methotrexate and/or paracetamol and/or other antibody based therapy. The combination may specifically comprise agents which are used for treating the primary disease, where inflammatory processes would lead to secondary inflammatory disease conditions. The primary disease is e.g. cancer and the combination would e.g. include antiproliferative chemotherapeutics and/or cytostatic agents.

In a combination therapy, the antibody may be administered as a mixture, or concomitantly with one or more other therapeutic regimens, e.g. either before, simultaneously or after concomitant therapy.

The biological properties of the antibody or the respective pharmaceutical preparation described herein may be characterized ex vivo in cell, tissue, and whole organism experiments. As is known in the art, drugs are often tested in vivo in animals, including but not limited to mice, rats, rabbits, dogs, cats, pigs, and monkeys, in order to measure a drug's efficacy for treatment against a disease or disease model, or to measure a drug's pharmacokinetics, pharmacodynamics, toxicity, and other properties. The animals may be referred to as disease models. Therapeutics are often tested in mice, including but not limited to nude mice, SCID mice, xenograft mice, and transgenic mice (including knockins and knockouts). Such experimentation may provide meaningful data for determination of the potential of the antibody to be used as a therapeutic or as a prophylactic with the appropriate half-life, effector function, inhibitor activity and/or immune response upon passive immunotherapy. Any organism, preferably mammals, may be used for testing. For example because of their genetic similarity to humans, primates, monkeys can be suitable therapeutic models, and thus may be used to test the efficacy, toxicity, pharmacokinetics, pharmacodynamics, half-life, or other property of the subject agent or composition. Tests in humans are ultimately required for approval as drugs, and thus of course these experiments are contemplated. Thus, the antibody and respective pharmaceutical compositions described herein may be tested in humans to determine their therapeutic or prophylactic efficacy, toxicity, immunogenicity, pharmacokinetics, and/or other clinical properties.

According to the invention an antibody construct targeting human TNFR1 with no agonistic cross-reactivity was produced. Selective inhibition of TNFR1 provides the opportunity to neutralize the pro-inflammatory activity or inflammatory responses of TNF. Specifically, a monovalently high affinity binder is provided which surprisingly not only avoids the undesired side effects of a corresponding divalent antibody, but more surprisingly is not converted into an agonist upon crosslinking by anti-human Ig antibodies (ADA) potentially developing in the course of repeated dosing typical for chronic disease treatment schedules.

An anti-TNFR1 antibody called ATROSAB, prepared according to WO2012035141A1 is a humanized antibody produced in mammalian cells and showed a similar binding and neutralizing behavior as the parental mouse H398 IgG. It did not show agonistic activity that would have been expected with such a full-length antibody.

Yet, the ATROSAB antibody surprisingly turned out to have agonistic activity as soon as a variant was produced with increased affinity. Thus, affinity maturation was in principle avoided to reduce undesired side effects. The present invention is now based on the surprising finding that an antibody construct that monovalently binds to the huTNFR1 receptor would not show such agonistic activity, even if affinity was increased to a $K_D$ of less than $10^{-8}$M and specifically even if the $k_{off}$ was substantially lowered.

The inhibitor described herein is a potent TNFR1-selective antagonist, and will permit new therapeutic options for diseases where anti-TNF therapeutics are indicated or where anti-TNF therapeutics failed or even exacerbate disease progression, including multiple sclerosis, congestive heart failure, metabolic diseases (type II diabetes), cytokine release syndrome, septic shock, acute (stroke) and chronic (Alzheimer and Parkinson disease) neurodegenerative diseases. The inhibitor can be an especially useful therapeutic alternative in diseases already known to clinically respond to anti-TNF treatment and particularly in those diseases where specific blockage of TNFR1 and maintenance of TNFR2 function appears as a promising therapeutic approach.

The subject matter of the following definitions is considered embodiments of the present invention:

1. An inhibitor of the huTNFR1 receptor which is a human or humanized antibody construct that monovalently recognizes huTNFR1 through an antigen-binding moiety with a $K_D$ of less than $5\times10^{-9}$ M and a $k_{off}$ of less than $10^{-3}$ s$^{-1}$ as determined for the Fab format by quartz crystal microbalance (QCM) at 37° C.

2. The inhibitor of definition 1, which directly inhibits the TNF-huTNFR1 receptor interaction or the huTNFR1 receptor interaction with lymphotoxin alpha, as determined in a cell-based assay, preferably by an assay for inhibition of TNFR1 mediated cell death in Kym-1 cells with an IC$_{50}$ value of less than $5.0\times10^{-9}$, or by an assay for inhibition of IL-6 release from HeLa cells with an IC$_{50}$ value of less than $4.0\times10^{-8}$, or by an assay for inhibition of IL-8 release from HT1080 cells with an IC$_{50}$ value of less than $2.0\times10^{-8}$.

3. The inhibitor of definitions 1 or 2, wherein the antigen-binding moiety comprises a VH and a VL domain, wherein at least one of the VH and VL domains is an affinity matured functional variant of a parent domain comprising at least one point mutation in any of the complementary determining region (CDR) sequences, wherein
a) the parent VH domain is characterized by the CDR sequences: SEQ ID 1 (CDRH1), SEQ ID 2 (CDRH2), and SEQ ID 3 (CDRH3); and
b) the parent VL domain is characterized by the CDR sequences: SEQ ID 4 (CDRL1), SEQ ID 5 (CDRL2), and SEQ ID 6 (CDRL3);
which CDR sequences are according to the Kabat numbering scheme.

4. The inhibitor of definition 3, wherein the at least one point mutation is in any of SEQ ID 2 (CDRH2) and/or SEQ ID 6 (CDRL3), preferably wherein the CDRH2 sequence is SEQ ID 7, and the CDRL3 sequence is SEQ ID 8.

5. The inhibitor of definitions 4 or 5, wherein the antigen-binding moiety is

A
selected from the group consisting of group members i) to ii), wherein
i)
is a antigen-binding moiety which comprises
a) a CDRH1 sequence identified by SEQ ID 1;
b) a CDRH2 sequence identified by SEQ ID 10;
c) a CDRH3 sequence identified by SEQ ID 3;
d) a CDRL1 sequence identified by SEQ ID 4;
e) a CDRL2 sequence identified by SEQ ID 5; and
f) a CDRL3 sequence identified by SEQ ID 11;
and
ii)
is a antigen-binding moiety which comprises
a) a CDRH1 sequence identified by SEQ ID 1;
b) a CDRH2 sequence identified by SEQ ID 10;
c) a CDRH3 sequence identified by SEQ ID 3;
d) a CDRL1 sequence identified by SEQ ID 4;
e) a CDRL2 sequence identified by SEQ ID 5; and
f) a CDRL3 sequence identified by SEQ ID 6;
or
B
an antigen-binding moiety which is a functionally active variant of a parent antigen-binding moiety that is any of the group members of A.

6. The inhibitor of definition 5, wherein the functionally active variant comprises
a) at least one functionally active CDR variant of any of the CDR sequences of the parent antibody; and/or
b) at least one point mutation in the framework region of any of the VH or VL sequences.

7. The inhibitor of any of definitions 1 to 6, wherein the antibody construct is selected from the group consisting of Fab molecules, scFv molecules, disulfide-stabilized Fv (dsFv), half-IgG1 antibodies, and Fv domains, or a functionally active derivative of any of the foregoing, preferably wherein the antibody construct is coupled to a hydrophilic polymer, such as PEG, and/or fused to a polypeptide, such as human serum albumin, transferrin, albumin-binding domains or peptides, Ig binding domains, PEG-mimetic polypeptide extensions, an antibody Fc fragment, an antibody Fc fragment carrying mutations to allow for preferred heterodimerization, or a functional variant of any of the foregoing polypeptides.

8. The inhibitor of definition 7, wherein the antibody construct is any of a Fab, scFv, dsFv, or Fv domains, which is fused to an antibody Fc fragment, wherein the Fc consists of a heterodimer of CH2 and CH3 domains, wherein the CH2 and/or CH3 domains carry one or more point mutations which allow preferential heterodimerization over homodimerization.

9. The inhibitor of any of definitions 1 to 8, wherein the antibody construct is PEGylated, HESylated, or PSAylated.

10. The inhibitor of any of definitions 1 to 9, wherein the antibody construct comprises Fv domains with increased affinity to bind the huTNFR1 as compared to parent Fv domains wherein the parent Fv domains are characterized by a parent VH domain identified as SEQ ID 12 and a parent VL domain identified as SEQ ID 16.

11. The inhibitor of definition 10, wherein at least one of the VH and VL domains is an affinity matured functional variant of the parent domain, comprising at least one point mutation in any of the CDR or framework (FR) sequences.

12. The inhibitor of definition 11, wherein
a) the VH domain comprises or consists of a sequence selected from the group consisting of SEQ ID 12-15;
b) the VL domain comprises or consists of a sequence selected from the group consisting of SEQ ID 16-19; or
c) the at least one of Fv domains comprises a functionally active variant of any of a) or b), wherein the functionally active variant comprises at least one point mutation in any of the CDR or FR sequences.

13. The inhibitor of any of definitions 10 to 12,
wherein the Fv domains are a combination of a VH and a VL domain, which are
A
selected from the group consisting of group members i) to ix), wherein
i)
VH comprises or consists of SEQ ID 13, and
VL comprises or consists of SEQ ID 17;
ii)
VH comprises or consists of SEQ ID 14, and
VL comprises or consists of SEQ ID 18;
iii)
VH comprises or consists of SEQ ID 15, and
VL comprises or consists of SEQ ID 19;
iv)
VH comprises or consists of SEQ ID 14, and
VL comprises or consists of SEQ ID 19;
v)
VH comprises or consists of SEQ ID 15, and
VL comprises or consists of SEQ ID 18;
vi)
VH comprises or consists of SEQ ID 13, and
VL comprises or consists of SEQ ID 18;
vii)
VH comprises or consists of SEQ ID 14, and
VL comprises or consists of SEQ ID 17;
viii)
VH comprises or consists of SEQ ID 13, and
VL comprises or consists of SEQ ID 19;
and
ix)
VH comprises or consists of SEQ ID 15, and
VL comprises or consists of SEQ ID 17;
or
B
the Fv domains are a combination of a VH and a VL domain, wherein any of the VH and VL domains is a functionally active variant of a parent domain of any of the group members of A.

14. The inhibitor of any of definitions 10 to 13, wherein the antibody construct has an increased thermostability of at least 60° C., or at least 61° C., or at least 62° C. or at least 63° C., or at least 64° C., or at least 65° C., as determined by dynamic light scattering wherein the antibody construct comprises Fv domains which are functional variants of parent Fv domains with at least one point mutation in the framework region of any of the VH or VL sequences.

15. A pharmaceutical preparation comprising the inhibitor of any of definitions 1 to 14 and a pharmaceutically acceptable carrier.

16. The preparation of definition 15, which is formulated for parenteral use, preferably by intravenous or subcutaneous administration.

17. Method of producing an inhibitor of any of definitions 1 to 14 employing a recombinant mammalian expression system to express the antibody construct.

18. Method according to definition 17, wherein a CHO production cell line is employed.

19. The inhibitor of any of definitions 1 to 14, for use in treating a human subject in need of an anti-TNF therapy.

20. The inhibitor for use according to definition 19, wherein the inhibitor is repeatedly administered to the subject.

21. The inhibitor for use according to definition 19 or 20, wherein the subject has developed anti-DMARD or anti-drug antibodies.

22. The inhibitor for use according to any of definitions 19 to 21, as first line treatment where anti-TNF therapies or non-biologic DMARD therapeutics are indicated, or as second line treatment where anti-TNF or non-biologic DMARD therapeutics failed.

23. The inhibitor for use according to any of definitions 20 to 22, wherein the subject is suffering from
a) acute or chronic inflammation of joints, skin and gut; and/or
b) autoimmune diseases, rheumatoid arthritis, psoriasis, psoriatic arthritis, juvenile arthritis, ankylosing spondylitis, Crohn's disease, multiple sclerosis, congestive heart failure, metabolic disease, cytokine release syndrome, septic shock, acute and chronic neurodegenerative disease, stroke, Alzheimer and Parkinson disease, colitis ulcerosa, pancreatitis, COPD, acute fulminant viral or bacterial infections, metabolic diseases, chronic neurodegenerative diseases, genetically inherited diseases with TNF/TNFR1 as the causative pathologic mediator, periodic fever syndrome, Cherubism, and cancer.

The present invention is further illustrated by the following examples without being limited thereto.

EXAMPLES

Example 1: Binding and Bioactivity of ATROSAB and H398

ATROSAB (full-length antibody produced according to WO02012035141) and its parental mouse antibody H398 (as described in WO2008113515A2) exhibit similar binding activity to human TNFR1 with $EC_{50}$ values of 0.25 nM and 0.15 nM in standard ELISA, respectively (FIG. 1a). Furthermore, similar affinities ($K_D$ values) of 0.35 nM for ATROSAB and 0.23 nM in the case of H398 were determined by QCM technology under conditions of high receptor density (FIGS. 1b and c).

Despite similar binding in ELISA and QCM, H398 showed a 10- to 12-fold stronger inhibition of TNF- or LT-induced IL-8 release from HT1080 cells compared with ATROSAB (FIG. 2). Considering that the receptors in both, ELISA and QCM measurements (performed on a high density chip), are overrepresented compared with the in vitro situation on HT1080 cells in the IL-8 release assay, it was decided to repeat QCM measurements using a chip with lower receptor density. As shown in FIG. 3, a $K_D$ value of 4.5 nM was obtained for ATROSAB, and for H398 $K_D$ value of 1.6 nM was obtained (see also Table 1). Interestingly, while the $K_D$ value of ATROSAB and H398 differed by a factor of 2.8, the association rate ($k_{on}$) of ATROSAB was 2.6-fold faster than the $k_{on}$ of H398 and the dissociation-rate ($k_{off}$) of H398 was about 7.6-fold slower than the dissociation of ATROSAB (FIG. 3, Table 1). Thus, competing with TNF or LT for receptor binding, ATROSAB (faster on-rate) occupies free receptors faster and H398 (slower off-rate) blocks occupied receptors longer.

Taking into account that in the setting of the standard IL-8 release assay (see below), receptors underlie continuous internalization and internalized receptors do still mediate signaling, the antibody that stays longer bound to the receptor (slower off-rate) might be the stronger inhibitor. A pH-dependent effect due to the acidified conditions in the endosomal compartment could be excluded, as binding of ATROSAB and H398 to human TNFR1-Fc in ELISA did not differ significantly among each other in experiments, performed at pH 5.4, pH 6.4, pH 7.4 and pH 8.4 (data not shown). Hence, it was decided to put efforts into the development of "off-rate matured" variants of ATROSAB.

TABLE 1

Binding and Bioactivity of ATROSAB and H398

| | ATROSAB | H398 | Factor |
|---|---|---|---|
| $EC_{50}$, ELISA [nM] | 0.25 | 0.15 | 1.7 |
| $K_D$, high density chip [nM] | 0.35 | 0.23 | 1.5 |
| $IC_{50}$, TNF [nM] | 42 | 4.1 | 10 |
| $IC_{50}$, LT [nM] | 7.6 | 0.65 | 12 |
| $K_D$, low density chip [nM] | 4.5 | 1.6 | 2.8 |
| $k_{off}$, low density chip [$s^{-1}$] | $4.7 \times 10^{-3}$ | $6.2 \times 10^{-4}$ | 7.6 |

Example 2: Phage Display Part 1—Site Directed Mutagenesis and Equilibrium Selection In previous work (PhD thesis of Kirstin Zettlitz, 2010), ATROSAB was subjected to affinity maturation using phage display libraries of individually randomized CDRH1, CDRH2, CDRL1, and CDRL2. Within these CDRs, positions identified in a model structure of IZI06.1 to be exposed in the antigen-binding site were randomized. Selections were performed under equilibrium conditions using soluble biotinylated huTNFR1-Fc in combination with streptavidin-coated magnetic Dynabeads. Selection conditions are presented in Table 2. Although preferred residues were identified for all four CDRs, only mutations in CDRH2 (Table 3) were found to show some improvements in TNFR1 binding. ScFvIG11 was isolated from round 6 and revealed binding to TNFR1-Fc with a two-fold higher $K_D$ compared with scFvIZI06.1 (ATROSAB) as determined by QCM. ScFvIG11 was selected for further experiments due to its nearly three-fold reduced off-rate constant $k_{off}$ of $2.6 \times 10^{-4}$ $s^{-1}$ compared with scFvIZI06.1 ($7.6 \times 10^{-4}$ $s^{-1}$), indicating slower dissociation of the antibody from the antibody-receptor complex. A sequence alignment of scFvIZI06.1 and scFvIG11 is shown in FIG. 4.

TABLE 2

Conditions for equilibrium selection using biotinylated antigen.

| Round | Antigen (nM) | Incubation | Phage | Beads | Wash, MPBST (PBS) |
|---|---|---|---|---|---|
| 0 | moR1, 20 nM | 1 h, RT | 10 µl = 2 × 10¹¹ | 500 µg | => use supernatant for selection |
| 1st | 10 nM | 4 h, RT | 10 µl = 2 × 10¹¹ | 500 µg | 3 (1) x |
| 2nd | 10 nM | o/n, 4° C.; 1 h, RT | 10 µl = 4 × 10¹⁰ | 500 µg | 15 (5) x |
| 3rd | 1 nM | o/n, 4° C.; 1 h, RT | 1 µl = 4 × 10⁹ | 100 µg | 20 (10) x |
| 4th | 1 nM | 3 h, RT | 1 µl = 4 × 10⁹ | 100 µg | 10, 1 h, RT (10) x |
| 5th | 0.1 nM | o/n, 4° C.; 1 h, RT | 1 µl = 4 × 10⁹ | 100 µg | 10, 2 h, RT (10) x |
| 6th | 0.1 nM | 3 d, 4° C.; 1 h, RT | 1 µl = 4 × 10⁹ | 100 µg | 10, 2 h, RT (10) x |

TABLE 3

Positions for site directed mutagenesis, library L2a

| CDRH2 (Kabat) | 502a3456789602345 |
|---|---|
| scFvIZI06.1 | EIYPYSGHAYYNEKFKA |
| Randomized residues | X.X.XX.X.X..X.... |
| Calculated diversity | 2.68 × 10⁸ |
| library size | 2.57 × 10⁸ |
| Functionality | 73% |

Example 3: Phage Display Part 2—Random Mutagenesis and Competitive Selection

The library used for the following selection experiments was generated by error-prone PCR of the whole sequence comprising VH and VL of scFvIG11 (6.2×10⁵ colony forming units). Ten analyzed single clones revealed an overall mutagenesis rate of 7.5 mutations per kilo base pair (7.5/kbp). Within the CDRs, covering 25% of the whole scFv sequence (180 of 729 bp), 15 of 55 mutations were observed (27%), indicating a rather equal distribution of mutations.

Selection of the Affinity Matured Clone scFvT12B

A negative selection round using human TNFR2 was performed prior to panning against human TNFR1, to retain receptor selectivity during the selection process. Displayed scFv fragments with improved binding behavior were selected, employing human TNFR1-Fc immobilized to immunotubes. Total binding changes of the selection pool were recorded by polyclonal phage ELISA after each round, demonstrating an about two-fold improvement after three selection rounds (FIG. 5a, selection conditions are reviewed in Table 4).

TABLE 4

Selection Conditions

| Round | Antigen | Phages | Competition |
|---|---|---|---|
| 1 | 1 µg/ml | 10 µl | — |
| 2 | 0.1 µg/ml | 1 µl | — |
| 3 | 0.01 µg/ml | 1 µl | 10 nM* |

*Unlabeled human TNFR1 in solution was used for competition for both, selection on DynaBeads and in Immunotubes.

Candidate phages, showing the strongest binding to human TNFR1 in ELISA (Table 5), were expressed as soluble scFv fragments and subject to kinetic analysis by QCM, using a sensor chip with a moderate receptor density. The clone scFvT12B revealed the slowest release from the receptor, indicated by the lowest $k_{off}$ value (FIG. 5b, Table 5).

TABLE 5

Relative $EC_{50}$ and $k_{off}$ values of candidates of Phage, Display Library EP03 compared with scFvIZI06.1

| Clone | $EC_{50}$ | $k_{off}$ |
|---|---|---|
| IZI06.1 | 1 | 1 |
| IG11 | n.d. | 0.31 |
| T12B | 0.017 | 0.25 |
| B12B | 0.021 | 0.77 |
| T2A | 0.023 | 0.47 |
| T1C | 0.009 | 0.76 |
| B8E | 0.046 | 0.41 |
| T12E | 0.047 | 0.50 |
| T7B | 0.062 | 0.47 |
| T9H | 0.041 | 0.38 |
| B6F | 0.251 | 0.66 |
| T10D | 0.006 | 0.72 |

Taken together, scFvT12B showed best binding characteristics in the QCM off-rate screening, supposed to be the key attribute for the improvement of receptor blockade. The DNA sequence of scFvT12B was changed at three positions compared with scFvIG11. Q1H and T53S in the CDRH2 of the heavy chain variable domain (VH) as well as S91G in the CDRL3 of the light chain variable domain (VL, FIG. 4).

Characterization of scFvT12B

The soluble antibody fragments scFvT12B, scFvIZI06.1 and scFvIG11 were produced in the periplasm of E. coli TG1 and proper expression was confirmed by SDS-PAGE, where minor contaminations in the purified samples could be observed (FIG. 6a). Concentration-dependent binding to human TNFR1 was demonstrated in ELISA, revealing $EC_{50}$ values of 3.8 nM, 2.6 nM and 2.0 nM for scFvIZI06.1, scFvIG11 and scFvT12B, respectively (FIG. 6b, Table 6). Hence, scFvT12B showed an improved binding under the applied conditions of 1.3-fold compared with scFvIG11. $K_D$ values, as determined by QCM, were 28.9 nM for scFvIZI06.1, 24.9 for scFvIG11 and 6.0 for scFvT12B, representing an 4.1-fold improved binding of scFvT12B compared with scFvIG11 (FIG. 6c, Table 6). The change in affinity originated from an improved association- (2.1-fold increased $k_{on}$) and dissociation-rate constant (2.0-fold decreased $k_{off}$, Table 6). Finally, scFvT12B blocked TNF induced interleukin-8 release in vitro with an improved antagonistic activity compared with scFvIZI06.1 and scFvIG11 (FIG. 6d). Obtained data could not be converged towards a standard inhibition curve due to an increasing signal at high concentrations of applied scFv. However, approximated concentrations of half-maximal inhibition reflected an about seven-fold stronger blockade of human TNFR1 by scFvT12B compared with scFvIG11 (Table 6).

TABLE 6

Characterization of scFvT12B compared with scFvIZI06.1 and scFvIG11. Improvement is indicated as factor regarding the values of scFvIG11.

| | scFvIZI06.1 | scFvIG11 | scFvT12B | Improved |
|---|---|---|---|---|
| $EC_{50}$ (nM) | 3.8 | 2.6 | 2.0 | 1.3 |
| $k_{on}$ ($M^{-1}s^{-1}$) | $5.0 \times 10^5$ | $1.5 \times 10^5$ | $3.0 \times 10^5$ | 2.1 |
| $k_{off}$ ($s^{-1}$) | $1.4 \times 10^{-2}$ | $3.6 \times 10^{-3}$ | $1.8 \times 10^{-2}$ | 2.0 |
| $K_D$ (nM) | 28.9 | 24.9 | 6.0 | 4.1 |
| $IC_{50}$ (nM)* | ~200 | ~300 | ~45 | ~6.7 |

*approximated $IC_{50}$ values, originating from evaluation of the obtained Il-8 data upon exclusion of the last 1-2 data points.

Example 3: Repeated Humanization of H398

As mentioned above, H398 proved to be more efficient in blocking TNF-mediated cellular responses compared with ATROSAB (Zettlitz et al. 2010), thus the humanization process that resulted in scFvIZI06.1 (ATROSAB) was recapitulated. To identify alternative human germline genes, humanness over sequence identity was prioritized and clones of rather low homology to scFvH398 for the repeated humanization of VH and VL were used. The genes, named 3-11*01 and 1-39*02, were selected due to their profound humanness (Abhinandan and Martin 2007), indicated by positive z-scores of higher value (Table 7). CDR sequences of the murine antibody H398 were transferred to the framework of the chosen germline sequences, resulting in the antibody fragment scFvFRK13. Analysis of the canonical structures of the newly generated scFv using auto-generated SDR templates (Copyright© 1995, Andrew C. R. Martin, UCL) indicated atypical amino acids at position H71 and L2. Hence, these residues were substituted by the amino acids used for the generation of ATROSAB (VH: R71A, VL: I2V). Changes in the amino acid sequence of heavy and light chain of the humanized scFv before (scFvFRK13.1) and after amino acid substitution (scFvFRK13.2), compared with scFvIZI06.1, are reviewed in an alignment in FIG. 7.

TABLE 7

Humanization of H398.

| Locus | Clone | Identity | BLAST score | z-score |
|---|---|---|---|---|
| H398-VH | — | — | — | -2.023 |
| 1-69*08 | DP88 | 60.2% | 127 | 0.317* |
| 3-11*01 | DP35 | 45.9% | 109 | 1.987 |

| Locus | Clone | Identity | BLAST score | Z-score |
|---|---|---|---|---|
| H398-VL | — | — | — | -1.829 |
| 2D-28*01 | DPK15 | 79.0% | 161 | -1.401* |
| 1-39*02 | DPK9 | 54.0% | 109 | 1.204 |

*germline gene used for the humanized IZI06.1 (ATROSAB scFv)

Expression and Characterization of scFvFRK13

Besides scFvFRK13.1 and scFvFRK13.2, combinations of their heavy and light chain variable domains and combinations with the heavy or light chain of scFvT12B were cloned and produced (FIG. 8). ScFv fragments were analyzed in SDS-PAGE under reducing conditions, demonstrating integer expression and clean purification only for scFvFRK13.5 and scFvFRK13.7 (FIG. 8b). Bands of higher and lower molecular weight were observed for all other constructs, indicating contaminations of the protein samples or degradation products. In addition, only scFvFRK13.5 and scFvFRK13.7 showed clean peaks in size exclusion chromatography, corresponding to the calculated molecular weight (FIG. 8c). Lower signals of shorter retention time were detected for both proteins, possibly representing the existence of dimeric scFv or aggregates of higher order. These findings indicate that the newly humanized VH domains result in unstable scFv molecules.

Receptor binding of scFvFRK13.1-13.8 was further analyzed in ELISA (FIG. 9a), using the scFv antibodies T12B and IZI06.1 as control proteins. While scFvFRK13.5, scFvFRK13.7 and scFvT12B bound to human TNFR1 with comparable $EC_{50}$ values of around 1 nM (Table 8), the remaining set of scFvs showed weak binding only at concentrations above 100 nM. Similarly, scFvFRK13.5, scFvFRK13.7 and scFvT12B inhibited TNF-induced IL-8 release from HT1080 cells with $IC_{50}$ values of around 300 nM. The control protein scFvIZI06.1 showed TNFR1 blockade with an $IC_{50}$ value of 932 nM (FIG. 9b, Table 8). Moreover, the thermal stability was investigated by dynamic light scattering. ScFvFRK13.5 and scFvFRK13.7 displayed melting temperatures of 63° C. and 65° C., compared with 59° C. and 55° C. of scFvIZI06.1 and scFvT12B, respectively (FIG. 10). Of note, scFvIZI06.1 showed already an increase in mean count rates at lower temperature, indicating partial destabilization of the protein structure. In contrast, the signals of scFvT12B, scFvFKR13.5 and scFvFRK13.7 were nearly constant below the melting point, revealing improved stability also at the lower temperature range.

TABLE 8

Characterization of humanized scFvH398 antibody fragments.

|  | H398 | IZI | T12B | FRK13.5 | FRK13.7 |
|---|---|---|---|---|---|
| Z-score VH | −2.023 | −0.419 | −0.500 | 0.760 | 0.698 |
| Z-score VL | −1.829 | −1.172 | −1.225 | 0.188 | 0.051 |
| $EC_{50}$ (nM) | n.d. | 3.07 | 1.14 | 1.06 | 1.09 |
| $IC_{50}$ (nM) | n.d. | 932 | 309 | 367 | 284 |
| $T_m$ (° C.) | n.d. | 59 | 55 | 63 | 65 |

In summary, scFv antibodies containing a newly humanized VH domain could not be expressed properly and seemed to destruct binding to human TNFR1. ScFvFRK13.7, containing the re-humanized VL domain and the VH domain of scFvT12B, was expressed to sufficient purity and bound to huTNFR1-Fc equally strong compared with the "off-rate matured" single-chain Fv antibody scFvT12B. In addition, scFvFRK13.7 revealed improved thermal stability.

Example 4: Conversion of scFvFRK13.7 into an IgG and a Fab Fragment

Heavy and light chain variable domains of scFvFRK13.7 were introduced into the background of ATROSAB IgG and ATROSAB Fab by standard cloning and PCR techniques. IgG-FRK13.7 and Fab-FRK13.7 are in the following referred to as IgG13.7 and Fab13.7, respectively. Proteins were produced transiently in HEK293T cells and purified by protein A (IgG13.7) or antibody (Fab13.7) affinity chromatography. IgG13.7 was subject to an additional preparative SEC (FPLC), due to minor peaks at higher molecular weight. Expression and protein integrity was monitored by SDS-PAGE under reducing (FIG. 11a) and non-reducing conditions (FIG. 11c) as well as by size exclusion chromatography (SEC, FIG. 11c). ATROSAB and FabATROSAB (FabATR) were used as controls in all experiments. All four proteins showed bands correlating with the calculated molecular weight during electrophoresis. Similarly, the observed absorption peaks in gel filtration confirmed homogenous protein preparations, all of apparent molecular weights in agreement with the expected sizes. Fab13.7 and IgG13.7 retained their specificity for human TNFR1 in ELISA compared with human TNFR2 and both mouse TNF receptors (FIG. 12).

Binding of FRK13.7 Antibodies to Human TNFR1

IgG13.7 and Fab13.7 bound to human TNFR1-Fc in ELISA with $EC_{50}$ values of 1.4 nM for Fab13.7 as well as 0.76 nM in the case of IgG13.7. The control proteins ATROSAB and FabATR showed 1.4-fold and 8.7-fold weaker binding compared with IgG13.7 and Fab13.7, respectively, indicated by higher $EC_{50}$ values (FIG. 13).

Moreover, evaluation of the binding dynamics was performed by quartz crystal microbalance, using sensor chips of moderate (86 Hz) or high (184 Hz) receptor density. The control antibody ATROSAB revealed a clear biphasic interaction with human TNFR1-Fc at moderate receptor density, composed of proportions with either high or low affinity, as represented by $K_D$ values of 0.38 nM and 78 nM, respectively (FIG. 14a, Table 9). In contrast, IgG13.7 showed in a OneToTwo binding analysis $k_{off}$ values in the range of $1.77 \times 10^{-4}$ to $9.30 \times 10^{-4}$ (data not shown), resulting in very low amounts of dissociating protein and thereby hardly detectable differences between mono- and bivalently binding and dissociating subpopulations. Therefore IgG13.7 was tested on a high-density chip, where the bivalent interaction was clearly dominating and the contribution of the monovalent interaction to the binding signal could be largely disregarded, allowing for the evaluation in a OneToOne analysis. The determined $K_D$ value of 0.11 nM reflected a 3.5-fold improvement compared with ATROSAB considering the bivalent binding situation (FIG. 14c). The monovalent control protein FabATR dissociated almost completely from the chip of moderate receptor density during the detection period (five minutes), revealing a dissociation rate constant ($k_{off}$) of $1.5 \times 10^{-2}$ s$^{-1}$ and a $K_D$ value of 30 nM (FIG. 14b). In contrast, the dissociation of Fab13.7 from the antibody-receptor complex was considerably slower, indicated by the $k_{off}$ value of $7.3 \times 10^{-4}$ s$^{-1}$, while the association rate constant ($k_{on}$) was nearly identical compared with FabATR. This resulted in a 19-fold stronger affinity of Fab13.7 to human TNFR1 with a $K_D$ value of 1.6 nM (FIG. 14d, Table 9).

TABLE 9

Affinity Determination of IgG13.7 and Fab13.7

|  | ATROSAB | IgG13.7 | FabATR | Fab13.7 |
|---|---|---|---|---|
| Bmax1 (Hz) | 16.8 |  | 6.36 | 8.93 |
| Bmax2 (Hz) | 10.73 | 55.93 |  |  |
| $k_{on}1$ (M$^{-1}$s$^{-1}$) | $2.82 \times 10^5$ |  | $5.01 \times 10^5$ | $4.70 \times 10^5$ |
| $k_{off}1$ (s$^{-1}$) | $2.19 \times 10^{-2}$ |  | $1.50 \times 10^{-2}$ | $7.32 \times 10^{-4}$ |
| $K_D1$ (nM) | 78 |  | 30 | 1.6 |
| $k_{on}2$ (M$^{-1}$s$^{-1}$) | $1.06 \times 10^6$ | $5.35 \times 10^5$ |  |  |
| $k_{off}2$ (s$^{-1}$) | $4.07 \times 10^{-4}$ | $5.92 \times 10^{-5}$ |  |  |
| $K_D2$ (nM) | 0.38 | 0.11 |  |  |

Thus, the monovalent antibody construct of ATROSAB (FabATR) has proven to be a far inferior binder to the huTNFR1 as compared to Fab13.7. Affinity of scFv IZI-06.1 binding to the huTNFR1 is alike FabATR, if the scFv affinity is measured in the Fab format. Though prior art measurements of scFv IZI-06.1 can show better results (because of avidity effects of dimerized scFv molecules), the affinity of binding (in the Fab format) is far inferior and equals the FabATR.

in single treatment. Fab13.7 and the control proteins ATROSAB and FabATR inhibited TNF-mediated cell death with $IC_{50}$ values of 4.7 nM, 24 nM and 37 nM, respectively, confirming the observations of the interleukin release assays (FIG. 17b, Table 10).

TABLE 10

Bioactivity of ATROSAB and FRK13.7 Antibodies

| | TNF (33 nM) | ATROSAB | FabATR | IgG13.7 | Fab13.7 | Cells |
|---|---|---|---|---|---|---|
| TNFR1 stimulation | | | | | | |
| IL-8 release (pg/ml) | 20850 | 240 | 128 | 4231 | 138 | 137 |
| IL-6 release (pg/ml) | 1667 | 231 | 179 | 1454 | 101 | 191 |
| Cytotoxicity (%) | 92 | — | — | up to 100 | — | — |
| Inhibition of cellular responses to 0.1 nM (IL-6, IL-8) or 0.01 nM TNF (cytotoxicity) | | | | | | |
| $IC_{50, IL-8}$ (nM) | — | 118 | 151 | — | 19 | — |
| $IC_{50, IL-6}$ (nM) | — | 179 | 145 | — | 31 | — |
| $IC_{50, Cytotox}$ (nM) | — | 24 | 37 | — | 4.7 | — |

In Vitro Bioactivity and Pharmacokinetics of scFv-FRK13.7 Derived Proteins

To investigate the influence of affinity maturation and re-humanization on the per se antagonistic antibody ATROSAB, the potential of scFvFRK13.7-derived IgG and Fab for the induction of interleukin-8 and -6 release from HT1080 and HeLa cells, respectively, was tested. ATROSAB, which was included as control, showed the described marginal receptor activation only in the case of IL-8 (Richter et al. 2013), in the performed IL-6 release experiments stimulation above the cellular background was not observed (FIGS. 15b and c). The monovalent control protein FabATR did neither stimulate IL-8 nor IL-6 release from the respective cell type. Consistently, increased interleukin release induced by Fab13.7 compared with untreated cells was not observed. However, IgG13.7 clearly stimulated the release of IL-8 and IL-6, resulting in interleukin levels of 20% to 87% compared with the effect of 33 nM TNF, which was around the maximum response stimulated by TNF in previous experiments.

Interestingly, IL-8 release from HT1080 cells triggered by 0.1 nM TNF was inhibited by ATROSAB and FabATR with comparable $IC_{50}$ values of 118 nM and 151 nM, respectively (FIG. 16a). Similarly, ATROSAB and FabATR revealed equally strong inhibition of IL-6 release from HeLa cells, caused by 0.1 nM TNF (FIG. 16b, Table 10). Due to its agonistic activity, a concentration of half-maximal inhibition ($IC_{50}$) of IgG13.7 was not determined. In contrast, Fab13.7 inhibited IL-8 and IL-6 release in response to 0.1 nM TNF in a dose-dependent manner with $IC_{50}$ values of 18.7 nM and 31.4 nM, respectively, revealing a 5.8-fold to 6.2-fold improved TNF neutralization compared with the full length IgG ATROSAB.

Furthermore, the potential of the whole length IgG and the Fab fragment originating from scFvFRK13.7 to promote or inhibit TNFR1 mediated cell death in Kym-1 cells was investigated. Consistent with the control proteins ATROSAB and FabATR, stimulation by Fab13.7 did not lead to any detectable cytotoxicity (FIG. 17a). On the other hand, IgG13.7 eradicated nearly 100% of Kym-1 cells at a broad range of concentrations, equivalent to the positive control TNF, which was used at 33 nM. To investigate the inhibitory capacity of the non-agonistic Fab13.7, Kym-1 cells were incubated with 0.01 nM TNF, killing around 90% of the cells In order to evaluate the risk of a potentially agonistic activity of Fab13.7 in the presence of drug-specific antibodies, the bioactivity of Fab13.7 on HT1080 cells in combination with a polyclonal anti human Fab serum isolated from goat was tested. In standard binding ELISA, binding of the human Fab specific goat serum to Fab13.7 could be shown (FIG. 18a), however, increased stimulatory activity above the cellular background of Fab13.7 together with 64 µg/ml of the serum in the IL-8 release assay was not detected (FIG. 18b). Yet, ATROSAB showed clearly increased induction of IL-8 in response to co-treatment with the anti human Fab serum (FIG. 18b). Similar results were obtained in previous experiments using ATROSAB together with an anti human Fc antibody (unpublished, data not shown).

The pharmacokinetic properties of FabATR and Fab13.7 were analyzed using transgenic C57BL/6J mice having the extracellular domain of TNFR1 replaced by the human counterpart (FIG. 19). Initial half-lives of around 0.25 hours indicated a rapid distribution in the body. Both Fab fragments were removed from the blood quickly by terminal half-lives of 1.7 hours for FabATR and 1.56 hours in the case of Fab13.7. These results revealed an unchanged pharmacokinetic profile of the evolved TNFR1 antagonistic Fab13.7, compared with the Fab fragment of ATROSAB. A summary of the data is depicted in Table 11.

TABLE 11

Pharmacokinetic Analysis of FabATR and Fab13.7

| | Initial | Terminal | Area under the curve [%*h] | |
|---|---|---|---|---|
| Construct | half-life [h] | half-life [h] | % of 3 min | % of ID |
| FabATR | 0.24 ± 0.02 | 1.56 ± 0.07 | 45.24 ± 2.68 | 51.91 ± 6.04 |
| Fab13.7 | 0.25 ± 0.06 | 1.7 ± 0.15 | 41.99 ± 5.53 | 36.04 ± 5.23 |

Example 5: PEGylated Derivative of Fab13.7

In order to circumvent the rather short circulation time of Fab13.7 in vivo, several strategies, intended to increase the hydrodynamic radius on the one hand and to enable FcRn-mediated drug recycling on the other hand, were subject to investigation.

Firstly, Fab13.7 (Fd: SEQ ID 25, light chain: SEQ ID 26) was modified at the heavy chain constant domain 1 (CH1) as described (Choy et al. 2002). Briefly, parts of the naturally occurring amino acid sequence of the IgG1 hinge region including the first cystein residue, followed by two alanine residues was added C-terminally to the CH1 domain ( . . . DKTHTCAA (SEQ ID 34), FIG. 20a, SEQ ID 27, light chain see Fab13.7, SEQ ID 26), resulting in Fab13.7'. $PEG_{400.000}$ was conjugated to Fab13.7' using 0.625 mM TCEP in order to reduce potentially formed disulfide linkages of the newly introduced cysteine residue (FIG. 20b). The thereby generated Fab13.7$_{PEG}$ bound to immobilized human TNFR1-Fc fusion protein in ELISA with 2.6-fold increased $EC_{50}$ values as compared to unmodified Fab13.7 (FIG. 20c, Table 12). Fab13.7$_{PEG}$ showed no significant activation of TNFR1 in vitro, as determined in an IL-8 release assay using HT1080 cells (FIG. 20d). Under the same assay conditions, Fab13.7$_{PEG}$ inhibited the IL-8 release from HT1080 cells, induced by 0.1 nM soluble TNF, with a 4.9-fold higher $IC_{50}$ value when compared to Fab13.7. (FIG. 20e, Table 12). Modification of Fab13.7 with $PEG_{400.000}$ resulted in an improved in vivo pharmacokinetic profile. Compared to Fab13.7, initial and terminal half-life and the area under the curve were increased by factors of 3.8, 18.0 and 22.2, respectively (FIG. 20f, Table 12).

Example 7: IgG-13.7 Half Antibody

To create a monovalent IgG molecule containing the intact Fab13.7 proportion and, in addition, the FcRn binding site which is located at the CH2-CH3 transition, the amino acid compositions of the IgG1 hinge region and Fc part were changed in order to avoid heavy chain dimerization (FIG. 22a, heavy chain IgG13.7$_{half}$: SEQ ID 29, light chain see Fab13.7, SEQ ID 26). Briefly the two cysteines of the hinge region were replaced by serines (C224S, C227S) in order to obstruct the formation of inter-chain disulfide linkages. Four additional mutations were introduced into the CH3 domain (P393A, F403R, Y405R, K407D), intended to obstruct homomeric CH3-CH3 interactions (see also Gu et al. 2015, SEQ ID 29, light chain see Fab13.7, SEQ ID 26). The thereby generated IgG13.7$_{half}$ showed one single band in SDS-PAGE under non-reducing conditions, corresponding to the calculated molecular weight of 73 kDa (FIG. 22b). Under reducing conditions two bands were observed, accounting for heavy and light chain. Size exclusion chromatography confirmed integrity of the protein structure and the absence of aggregated or oligomerized protein fractions (FIG. 21c). IgG13.7$_{half}$ bound to immobilized human

TABLE 12

Bioactivity of monovalent Fab13.7 Variants

| Molecule | ELISA Binding $EC_{50}$ [nM] | IL-8 Inhibition $IC_{50}$ [nM] | Initial Half-Life [h] | Terminal Half-Life [h] | Area Under The Curve [%*h] |
|---|---|---|---|---|---|
| Fab13.7$_{PEG}$ | 5.0 | 98.2 | 0.92 ± 0.04 | 28.04 ± 6.76 | 1008.03 ± 142.42 |
| Fab13.7-MSA | 0.7 | 65.5 | 1.85 ± 0.31 | 6.71 ± 0.85 | 966.20 ± 13.97 |
| IgG13.7$_{half}$ | 0.8 | 63.3 | 0.89 ± 0.38 | 3.51 ± 0.32 | 205.03 ± 56.18 |
| Fab13.7-Fc$_{kih}$0DS | 0.5 | 61.2 | 1.67 ± 0.51 | 13.88 ± 0.69 | 967.64 ± 101.82 |
| Fv13.7-Fc$_{kih}$0DS | 0.3 | 30.7 | 0.97 ± 0.23 | 16.38 ± 0.49 | 701.30 ± 119.62 |

*Varying values detected in different single experiments

Example 6: Fab13.7 MSA Fusion Protein

In another approach, Fab13.7 was genetically fused to mouse serum albumin (MSA), connected by a 12 amino acid linker (FIG. 21a, Fd-MSA: SEQ ID 28, light chain see Fab13.7, SEQ ID 26). The thereby generated Fab13.7-MSA showed one single band in SDS-PAGE under non-reducing conditions, corresponding to the calculated molecular weight of 114 kDa (FIG. 21b). Under reducing conditions two bands were observed, accounting for the dissociated light chain and the Fd fragment, fused to the MSA moiety. Size exclusion chromatography confirmed integrity of the protein structure and the absence of aggregated or oligomerized protein fractions (FIG. 20c). Fab13.7-MSA bound to immobilized human TNFR1-Fc fusion protein in ELISA with a 1.7-fold increased $EC_{50}$ value as compared to unmodified Fab13.7 (FIG. 21d, Table 12) and showed no significant activation of TNFR1 in vitro, as determined in an IL-8 release assay using HT1080 cells (FIG. 21e). Under the same assay conditions, Fab13.7-MSA inhibited the IL-8 release from HT1080 cells, induced by 0.1 nM soluble TNF, with a 1.9-fold higher $IC_{50}$ value when compared to Fab13.7. (FIG. 21f, Table 12). Fusion of Fab13.7 to MSA resulted in an improved in vivo pharmacokinetic profile. Compared to Fab13.7, initial and terminal half-life as well as the area under the curve were increased by factors of 7.8, 4.3 and 21.3, respectively (FIG. 21g, Table 12).

TNFR1-Fc fusion protein in ELISA with a 1.9-fold increased $EC_{50}$ value as compared to unmodified Fab13.7 (FIG. 22d, Table 12) and showed no significant activation of TNFR1 in vitro, as determined in an IL-8 release assay using HT1080 cells (FIG. 22e). Under the same assay conditions, IgG13.7$_{half}$ inhibited the IL-8 release from HT1080 cells, induced by 0.1 nM soluble TNF, with a 1.8-fold higher $IC_{50}$ value when compared to Fab13.7. (FIG. 22f, Table 12). Fusion of Fab13.7 to a monomeric Fc part resulted in an improved in vivo pharmacokinetic profile. Compared to Fab13.7, initial and terminal half-life as well as the area under the curve of IgG13.7$_{half}$ were increased by factors of 3.7, 2.3 and 4.5, respectively (FIG. 22g, Table 12).

Example 8: Monovalent Fab13.7-Fc Fusion Protein

In order to overcome the limited improvement of pharmacokinetic properties in the case of IgG13.7$_{half}$, Fd and light chain of Fab13.7 were both fused to a protein moiety consisting of FcγR-silenced CH2 and CH3 domains, which contained additional mutations that foster hetero-dimerization applying the "knobs-into-holes" modifications (FIG. 23a, Merchant et al. 2013, Fd13.7-Fc$_{hole}$: SEQ ID 30, LC13.7-Fc$_{knob}$: SEQ ID 31). Briefly, in addition to the mutations in CH1, hinge region and CH2, which were reported to suppress binding to Fcγ receptors (Armour et al. 1999, Richter et al. 2013, Shields et al. 2001, Zettlitz et al. 2010) and the above described cysteine to serine changes in the hinge region, the mutations T366S, L368A and Y407V were introduced into the CH3 domain, connected to the Fd fragment, while a single threonine residue of the CH3 domain linked to the Fab13.7 light chain was changed to tryptophane (T366W). The thereby generated Fab13.7-Fc$_{kih}$0DS (Fab13.7 connected to an Fc part with knobs-into-holes [kih] driven hetero-dimerization and no disulfide [0DS] bonds in hinge region) showed one single band in SDS-PAGE under non-reducing conditions, corresponding to the calculated molecular weight of 98 kDa for the whole protein (FIG. 23b). Under reducing conditions two bands were observed, accounting for heavy and light chain. Size exclusion chromatography confirmed integrity of the protein structure and the absence of aggregated or oligomerized protein fractions (FIG. 23c). Fab13.7-Fc$_{kih}$0DS bound to immobilized human TNFR1-Fc fusion protein in ELISA with similar activity as compared to unmodified Fab13.7 (FIG. 23d, Table 12) and showed no significant activation of TNFR1 in vitro, as determined in an IL-8 release assay using HT1080 cells (FIG. 23e). Under the same assay conditions, Fab13.7-Fc$_{kih}$0DS inhibited the IL-8 release from HT1080 cells, induced by 0.1 nM soluble TNF, with a 2.3-fold higher IC$_{50}$ value when compared to Fab13.7. (FIG. 23f, Table 12). Fusion of Fab13.7 to a hetero-dimeric Fc part resulted in an improved in vivo pharmacokinetic profile. Compared to Fab13.7, initial and terminal half-life as well as the area under the curve of Fab13.7-Fc$_{kih}$0DS were increased by factors of 7.0, 8.9 and 21.3, respectively (FIG. 23g, Table 12).

Example 9: Monovalent Fv13.7-Fc Fusion Protein

In another format, the variable domains (VH, VL) of Fv13.7 were separately fused to the hinge region of Fc chains (VH-hinge-Fc(knob), VL-hinge-Fc(hole)) as described for Fab13.7-Fc$_{kih}$0DS (FIG. 24a, VH13.7-Fc$_{hole}$: SEQ ID 32, VL13.7-Fc$_{knob}$: SEQ ID 33). The thereby generated Fv13.7-Fc$_{kih}$0DS showed one single band in SDS-PAGE under reducing and non-reducing conditions, accounting for both individual polypeptide chains, which are of similar molecular weight, resulting in a calculated MW of 98 kDa for the whole protein (FIG. 24b). Size exclusion chromatography confirmed integrity of the protein structure and the absence of aggregated or oligomerized protein fractions (FIG. 24c). Fv13.7-Fc$_{kih}$0DS bound to immobilized human TNFR1-Fc fusion protein in ELISA with slightly increased activity as compared to unmodified Fab13.7 (FIG. 24d, Table 12) and showed no significant activation of TNFR1 in vitro, as determined in an IL-8 release assay using HT1080 cells (FIG. 24e). Under the same assay conditions, Fv13.7-Fc$_{kih}$0DS inhibited the IL-8 release from HT1080 cells, induced by 0.1 nM soluble TNF, with a similar IC$_{50}$ value when compared to Fab13.7. (FIG. 24f, Table 12). Fusion of Fv13.7 to a hetero-dimeric Fc part resulted in an improved in vivo pharmacokinetic profile. Compared to Fab13.7, initial and terminal half-life as well as the area under the curve of Fv13.7-Fc$_{kih}$0DS were increased by factors of 4.1, 10.5 and 15.4, respectively (FIG. 24g, Table 12).

The present data demonstrate the improved antagonistic potency of Fab13.7 compared with ATROSAB and FabATR, originating from a considerably slower dissociation of the antibody receptor complex. As similar IC$_{50}$ values were observed for ATROSAB and FabATR in interleukin release and cytotoxicity assays, the presence of only one receptor binding site instead of two, does not seem to reduce the capacity to inhibit TNF-mediated TNFR1 activation. In contrast, the absence of a second binding site for human TNFR1 eliminated the agonistic potency observed in the case of IgG13.7. Moreover, no agonistic activity of Fab13.7 was detectable alone or in the presence of a polyclonal goat serum specific for human Fab, intended to restore bi- or multivalency by antibody mediated cross-linking. This could possibly indicate a reduced risk of inflammation-related side effects in the in vivo situation, even in the case of an anti-drug immune response. Lastly, due to the reduced size and the lack of FcRn-mediated drug recycling, Fab13.7 exhibits a rather short circulation time in the blood, compared with whole IgG molecules. The implementation of half-life extension strategies allow to overcome this disadvantage underlined the potential of Fab13.7 to be modified successfully in order to meet the needs of long circulation in the human body concerning future clinical application.

Example 10: Specific Materials and Methods of Standard Assays

Materials

Horseradish peroxidase (HRP)-conjugated anti-mouse IgG (Fc specific) antibody, HRP-conjugated anti-human IgG (whole molecule, Fc specific, Fab specific) antibodies, respectively, were purchased from Sigma (Taufkirchen, Germany). HRP-conjugated antibody targeting the His-tag of scFv antbodies was purchased from Santa Cruz Biotechnology (Santa Cruz, USA). The human rhabdomyosarcoma cell line Kym-1 was grown in RPMI 1640 medium, 10% FCS, 2 mM L-glutamine and HT1080 wt cells and HeLa cells were grown RPMI 1640 medium, 5% FCS, 2 mM L-glutamine. Human TNFR2-Fc fusion protein (Mohler et al. 1993, The Journal of Immunology 151. Jg., Nr. 3, S. 1548-1561). Chemicals were purchased from Roth (Karlsruhe, Germany) while enzymes (cloning and PCR) and supplemental reagents were purchased from ThermoFisher (Munich, Germany). Any different source of consumables is clearly stated below.

Expression of TNFR1-Fc Fusion Proteins

DNA encoding the extracellular region of human TNFR1 (aa 29-211), mouse TNFR1 (aa 30-212), and mouse TNFR2 (aa 23-258) was produced synthetically (Geneart, Regensburg, Germany) using the sequence information of UniProtKB (Swiss-Prot) entry P19438 (human (*Homo sapiens*) TNFR1), P20333 (human (*Homo sapiens*) TNFR2), and P25119 (mouse (*Mus musculus*) TNFR2), introducing appropriate restriction sites between the individual domains, and cloned into pSecTagL1-Fc (modified from pSecTag-FcHis, (Muller et al. J. Immunol. Methods (2008) 339(1): 90-8)). HEK293 cells were transfected with plasmid DNA using lipofectamine (Invitrogen, Karlsruhe, Germany) and stably transfected clones were selected in the presence of zeocin as described (Muller et al. J. Biol. Chem (2007) 282(17):12650-60). Cells were expanded in RPMI, 5% FCS, 2 mM L-glutamine to 90% confluence. For protein production, the medium was substituted with Opti-MEM I (Invitrogen, Karlsruhe Germany) and supernatant was collected every 3-4 days. Proteins were purified from cell culture supernatant as described below.

Expression of scFv Antibody Fragments in the Periplasm of *E. coli* TG1

A starting culture of *E. coli* TG1 containing the expression plasmid was incubated overnight in 20 ml 2×TY (100 µg/ml Ampicillin, 1% glucose) at 37° C. The next day, 1 liter 2×TY (100 µg/ml Ampicillin, 0.1% glucose) was inoculated with 10 ml of the over-night culture and incubated shaking at 37° C. until an OD [600 nm] of 0.8 to 1.0 was reached. Subsequent to the addition of 1 ml IPTG (final concentration 1 mM), the culture was incubated at room temperature for additional 3 to 4 hours. Bacteria were harvested by centrifugation at 4500*g and the pellet was resuspended in PPB to a final volume of 50 ml. To release the antibody fragments from the periplasm, 0.25 ml of lysozyme (10 mg/ml in ddH2O) were added and the suspension, followed by incubation on ice for 30 minutes. Prior to the next centrifugation step (10,000*g, 10 minutes, 4° C.), the remaining spheroblasts were stabilized by the addition of 0.5 ml of 1 M MgSO4. The supernatant was dialyzed over night at 4° C. against PBS. Antibody fragments were purified from the dialyzed solution after an additional centrifugation step (1000*g, 15 min, 4° C.) as described below.

Expression of IgG13.7 and Fab3.7 after Transient Transfection

HEK293 cells were cultivated until five 175 cm$^2$ bottles reached 70-90% confluency. 100 µg of the vector DNA and 250 µl Lipofectamine were first mixed individually, each with 7 ml Opti-MEM and then mixed together and incubated for 30 minutes at RT. The transfection mix was adjusted to a volume of 25 ml using Opti-MEM, the culture medium of each bottle was replaced by 5 ml of the transfection solution and the cells were incubated at 37° C., 5% C02 for 4-6 hours. Production was started by replacing the transfection medium by 50 ml Opti-MEM, which was replaced every second day until at least one liter was collected. Supernatants were sterile filtered and purified as described below.

Protein Purification—Immobilized Metal Affinity Chromatography (IMAC)

Sterile filtered tissue culture supernatants or dialyzed periplasmatic extracts were incubated with Ni-NTA (Ni-NTA Agarose, 64-17-5, Macherey-Nagel, Dueren, Germany) rolling at 4° C. over night. In order to collect the purification resin, the beads containing supernatants were loaded to a Poly-Prep® chromatography column by gravity flow or moderate vacuum pressure. Washing was performed using IMAC buffer containing 20 mM Imidazol until almost no protein could be detected in the flow through by a concomitant Bradford test (90 µl Bradford reagent (500-0006, BIO-RAD, Munich, Germany)+10 µl sample mixed in a 96-well microtiter plate). Protein was eluted from the resin with 250 mM Imidazol in IMAC buffer and fractions of 500 µl were collected. The protein containing fractions (determined by Bradford quick test as described) were pooled and dialyzed against PBS.

Protein Purification—Antibody and Protein a Affinity Chromatography

Procedure was performed exactly as described for IMAC, using either TOYOPEARL® AFrProtein A-650F (protein A resin, 22805, Tosoh, Stuttgart, Germany) or HiTrap KappaSelect (kappa chain selective antibody fragments conjugated to a agarose matrix, 17-5458-12, GE Healthcare, Chalfont St Giles, GB) resins. Washing was performed using PBS and proteins were eluted from the resin with 100 mM glycine at pH 2-3. Eluted fractions were directly pooled and immediately dialyzed against PBS.

Preparative Size Exclusion Chromatography

In the case of aggregated or multimeric assembled protein in the preparations, an additional size exclusion step was performed using the Äkta purifier. Proteins were separated on a Superdex 200 10/300 GL column at a flow rate of 0.5 ml/min using PBS as liquid phase. Fractions of 200 µl were collected and the peak containing samples were pooled for further experiments.

Protein Characterization—Poly-Acryamide Gel Electrophoresis (SDS-PAGE)

SDS-PAGE was performed strictly according to Laemmli 1970, using 3 µg of protein preparations and the indicated percentages of stacking and separation gel.

Protein Characterization—Size Exclusion Chromatography (SEC)

To determine the hydrodynamic radius, 30 µg purified protein samples were analyzed using the Waters 2695 HPLC in combination with a Phenomenex Yarra SEC-2000 column (300×7.8 mm, flow rate of 0.5 ml/min). The mobile phase was 0.1 M Na2HPO4/NaH2PO4, 0.1 M Na2SO4, pH 6.7. The following standard proteins were used: Thyroglobulin (669 kDa), Apoferritin (443 kDa), Alcohol dehydrogenase (150 kDa), BSA (66 kDa), Carbonic anhydrase (29 kDa), FLAG peptide (1 kDa).

Protein Characterization—Thermal Stability by Dynamic Light Scattering

Stability to increasing temperatures was measured by dynamic light scattering using the ZetaSizer Nano ZS (Malvern, Herrenberg, Germany). Around 100 µg of the purified protein samples were adjusted to a total volume of 1 ml by the use of PBS and applied to a quartz cuvette. Kilo counts per second (kcps) were measured, indicating the size of denatured protein particles in the solution, which increases while the protein aggregates upon heating. Temperature was increased stepwise from 35° C. to 80° C. (1° C. intervals, 2 minutes equilibration prior to each measurement).

Enzyme-Linked Immunosorbent Assay (ELISA)

Microtiter plates were coated with 100 µl of the indicated protein (1 µg/ml in PBS, see Table 3.3) and incubated at 4° C. over night. The residual binding sites were blocked with 2% MPBS (skim milk in PBS, 200 µl per well) at room temperature for 2 hours and subsequently washed twice with PBS. 100 µl of the samples diluted in 2% MPBS were incubated at room temperature for 1 hour prior to the last incubation step with 100 µl of the HRP conjugated detection antibodies in 2% MPBS. In the case of competition experiments, both analyzed protein samples were prepared individually (either titrated or diluted to a single concentration) and mixed before they were applied to the plate. Bound protein was detected with 100 µl TMB substrate solution, the HRP-reaction was stopped by the addition of 50 µl 1 M H2SO4 and the absorption at the wavelength of 450 nm was measured using the Infinite microtiter plate reader (TECAN, Maennedorf, Switzerland). Between each incubation step and in advance of the detection, the plates were washed three times with PBST and twice with PBS.

Affinity Measurements Using the Quartz Christal Microbalance

Real-time binding dynamics in protein-protein interactions were determined by quartz crystal microbalance measurements (A-100 C-Fast or Cell-200 C-Fast, Attana, Stockholm, Sweden). One of the binding partners (ligand, e.g. TNFR1-Fc) was chemically immobilized on a carboxyl sensor chip according to the manufacturer's protocol at different densities (nearly 200 Hz in the case of saturating conditions to confirm previously published results and 50-100 Hz, in particular at about 50 Hz, to establish conditions of lower receptor density, better resembling the situation on the cellular surface). Binding experiments were performed with samples (analyte) diluted in PBST (PBS, 0.1% Tween 20) at pH 7.4 with a flow rate of 25 µl/min at 37° C. The chip was regenerated with 25 µl 5 mM NaOH or 20 mM glycine, pH 2.0. Every third measurement, an injection of running buffer was measured which was subtracted from the binding curve. Data were collected using the software provided by Attana for the particular device and analyzed by Attaché Office Evaluation software (Attana, Stockholm, Sweden) and TraceDrawe (ridgview instruments, Vange, Sweden).

Kym-1 Cytotoxicity Assay

Kym-1 cells ($1\times10^4$ per well) were seeded into 96-well microtiter plates and incubated over night at 37° C. and 5% $CO_2$. The proteins were diluted in RPMI 1640+10% FCS. If two protein species were used together in competition experiments, both samples were prepared individually (either titrated or diluted to a single concentration) and mixed before they were applied to the plate. Plates were incubated at 37° C., 5% CO2 for 24 hours before the supernatant was discarded and 50 µl crystal violet solution was added to the cells. Subsequently, the plates were washed in dd$H_2$O for 20 times and dried. The remaining violet dye, resulting from living and adherent cells, which were fixed by the methanol contained in the staining solution, was dissolved by the addition of 100 µl methanol upon shaking at RT for 10 minutes. Plates were measured using the Infinite microtiter-plate reader (Tecan, Maennedorf, Switzerland).

Interleukin Release Assay $2\times10^4$ HeLa or HT1080 cells per well were seeded into a 96 well microtiter plate and grown in 100 µl RPMI 1640+5% FCS over night. The next day, the supernatants were exchanged in order to remove constitutively produced cytokines. The cells were incubated with dilution series of samples in RPMI 1640+5% FCS at 37° C., 5% $CO_2$. In the case of competition experiments, both analyzed protein samples were prepared individually (either titrated or diluted to a single concentration) and mixed before they were applied to the plate. Non-stimulated cells served as control. After 16-20 hours, the plates were centrifuged at 500 g for 5 minutes and cell supernatants were analyzed directly by ELISA, which was performed according to the protocol of the manufacturer. Supernatants were diluted in RPMI 1640 (without FCS) and antibodies were diluted in Reagent Diluent (0.1% BSA, 0.05% Tween 20, 20 mM TRIS, 150 mM NaCl, pH7.5). The coated microtiter plates were blocked using 2% BSA (Bovine Serum Albumin) in PBS and washing as well as detection and measuring were performed as described above for ELISA. Sandwich ELISA kits for the detection of IL-6 and IL-8 in the cell culture supernatant were purchased from ImmunoTools, (Friesoythe, Germany).

Pharmacokinetics

Transgenic C57BL/6J mice, bearing the gene of the extracellular domain of human TNFR-1 at the locus of the particular mouse gene (C57BL/6J-huTNFRSF1Aecdtm1UEG/izi), were injected intravenously with 12 µg to 25 µg of the analyzed proteins. C57BL/6J of an unaltered genetic background served as control. Blood samples were collected after 3 min, 30 min, 1 h, 3 h and 6 h as well as after 3 days and 7 days and incubated on ice immediately. Serum was separated by centrifugation (13.000 g, 4° C., 10 minutes) and stored at −20° C. Remaining protein in the serum was detected by binding ELISA as described above. Data were displayed as percentage of the 3 min value. Alternatively, the ELISA signal at the injection time was interpolated from the obtained curves and set to the initial in vivo concentration on the basis of the injected dose and the average blood volume of the mice, resulting in the indicated concentrations at the measurement time points Phage Display—Cloning of Acceptor Vector pHENIS_s-cFvIG11-fsSTOP The DNA sequence encoding for scFvIG11 was amplified by PCR (described above) from the template pHENIS-scFvL2a_huBR6_IG11 (Zettlitz 2010b) using the primers NcoI_VHIZI06.1_back and BstZ17I_fsSTOP_BssHII_for. The obtained DNA fragment, containing a frame shift in combination with stop a codon, was inserted again into pHENISscFvL2a_huBR6_IG11 after digestion with NcoI and BstZ17I, resulting in the acceptor vector pHENIS_s-cFvIG11-fsSTOP.

Phage Display—Generation of Selection Library EP03

The selection library EP03 for the affinity maturation of scFvIG11, resulting in scFvT12B was generated by error prone PCR using the GeneMorph II Random Mutagenesis Kit (200550, Agilent Technologies, Santa Clara, Calif., USA) according to the manufacturers protocol. The Template DNA pHENIS-scFvLib2a_huBR6_IG11 was amplified by the use of the primers LMB2 and fdSeq1. Intended to generate a moderate incidence of mutations, 0.1 µg template DNA were used in a 30 cycles PCR reaction. The resulting PCR-Product was cloned into the acceptor vector pHENIS_scFvIG11_fsSTOP after digestion by the enzymes NcoI and NotI. Ligation was performed over night at 16° C. The next day, ligated DNA was precipitated by the addition of ¹⁄₁₀ of the ligation mix volume (LMV) of 3 M NaAc pH 5.2, 5 µl Glycogen (20 µg/µl) and 2.7 LMV of 100% Ethanol. Following an 1 hour incubation at −80° C., the DNA was centrifuged (13.000*g, RT, 5 minutes) and the air-dried pellet was resuspended in 40 µl ddH2O and frozen again at −20° C. in 2-4 µl aliquots. 3.18.3. Preparation of Electrocompetent *E. coli* TG1 Transferring 5 ml of an over-night culture of *E. coli* TG1 grown in SOB medium (containing 1% glucose) to 500 ml fresh SOB, a culture was inoculated and grown until an OD [600 nm] of 0.5-1.0 was reached. Cells were chilled on ice subsequently for at least 15 minutes and harvested by centrifugation (2000*g, 4° C., 15 min). The cell pellet was gently resuspended in 200 ml ice cold ddH2O (firstly using 20 ml, another 180 ml were added after resuspension). The centrifugation/resuspension cycle was repeated for a second time exactly as described, the resuspended cells were then kept on ice for 30 minutes and centrifuged again (2000*g, 4° C., 15 min). Bacteria were resuspended in 50 ml of 10% glycerol, incubated on ice for another 30 minutes and collected again by centrifugation (1500*g, 4° C., 15 min). The resulting pellet was resuspended to a final volume of 500 to 1000 µl, kept on ice and used directly for electroporation.

Phage Display—Electroporation of *E. coli* TG1

Electrocompetent *E. coli* TG1 (StrataGen, Kirkland, Wash., USA) were freshly prepared and 40 µl of the cell suspension was mixed with a frozen aliquot of ligated DNA. After 1 minute incubation on ice, the DNA bacteria mix was transferred to an electroporation cuvette (BIO-RAD, Munich, Germany) and electroporated immediately (17 kV/cm, 200Ω, 25 µF, GenePulser® XCell, BIO-RAD, Munich, Germany). Subsequently, the transformed cells were rescued by flushing the cuvette with 1 ml of LB, transferred to a culture tube and incubated shaking at 37° C. for 1 hour, prior to plating on LBamp agar plates. For control purposes, 10 µl, 1 µl and 0.1 µl of a transformed sample were plated separately onto LBamp agar plates, as well as 2.5 µl of electroporation samples containing either 2 µl ddH2O or 1 µl pUC DNA (0.1 ng/µl) mixed with the competent cells.

Phage Display—Preparation of Helper Phages

*E. coli* TG from an over-night culture, which was started with bacteria freshly streaked on a minimal plate, were used to inoculate a 500 ml 2×TY culture (OD [600 nm] 0.05-0.07). At an OD [600 nm] of 0.4 to 0.5, 1 ml VSC M13 helper phages (StrataGen, Kirkland, Wash., USA) were added and the culture was incubated for 30 minutes without shaking at 37° C. and for another 30 minutes, shaking at 37° C. Subsequently, Kanamycin was added to a final concentration of 30 µg/ml and the culture was incubated shaking at 30° C. over night. Finally, bacteria were separated by centrifugation (4000*g, 45 min, RT) and the phage containing supernatant was stored at −20° C. in 1 ml aliquots.

Phage Display—Phage Rescue and Precipitation

Transformed bacteria were collected from LB agar plates and 50 ml 2×TY (2% glucose, 100 µg/ml Ampicillin) were inoculated to a starting OD [500 nm] of 0.05-0.07. When the culture reached an OD [600 nm] of 0.4-0.5 after shaking incubation at 37° C., 1 ml of VSC M13 helper phages were added and the culture was incubated at 37° C. first without shaking (30 minutes) and then shaking (30 min). Subsequently, the bacteria were harvested by centrifugation (4000*g, RT, 15 min), resuspended in 50 ml fresh 2×TY containing 100 µg/ml Ampicillin and 30 µg/ml Kanamycin and incubated, shaking, at 30° C. over night. The next day, bacteria were centrifuged (4000*g, RT, 30 min) and 10 ml of 20% PEG6000 were added to 40 ml of the supernatant, gently mixed and rolled at 4° C. for 1 hour. Precipitated phages were dissolved in 1 ml PBS after centrifugation (4000*g, RT, 30 min) and centrifuged again at 13.000*g and RT for 10 min. The bacteria-free supernatant, containing the amplified phages was used immediately for selection (or stored at 4° C. for later usage).

Phage Display—Immunotube Selection

Immunotubes were coated with human TNFR1-Fc or human TNFR2-Fc at concentrations decreasing with each selection round (Round 1: 1 and 0.1 µg/ml, round 2: 0.1 and 0.01 µg/ml, etc.; huTNFR2 always was coated using 2 µg/ml). Tubes were blocked with 2% MPBS. 1 or 10 µl precipitated phages were added to 1 ml 2% MPBS and incubated in human TNFR2-Fc coated tubes to eliminate cross-reactive phages. This negative selection was performed exclusively prior to the first round of selection. Following 1 hour incubation at RT, the supernatant was transferred to immunotubes coated with human TNFR1-Fc and incubated for an additional hour. Starting at round 2, soluble human TNFR1-Fc was added to the immunotube at a final concentration of 5 µg/ml in order to capture quickly dissociating phages and to hinder their binding to the immobilized receptors. The supernatant was subsequently discarded and the tubes were washed 10 times with PBST (0.1% Tween 20) and 10 times with PBS. Phages were eluted with 1 ml of 100 mM TEA (triethylamine) upon incubation for 7 minutes. The eluted phages were neutralized immediately using 500 µl of 1 M TrisHCl buffer (pH 7.5) and added to 8.5 ml of early log phase E. coli TG1. Incubation was performed as described above for transduction (37° C., standing, 30 min; 37° C., shaking, 30 min). Bacteria were separated by centrifugation (4000*g, RT, 10 min) and plated to LBamp plates.

Phage Display—Biotinylation of Receptor-Fc Fusion Proteins

Human TNFR1-Fc and human TNFR2-Fc were biotinylated upon mixing protein samples with a 20-fold molar excess of Sulfo-NHS-SS-Biotin (Pierce, Rockford, USA) and incubation at RT for 2 hours. Remaining free Sulfo-NHS-SS-Biotin was removed from the sample by dialysis against PBS at 4° C. over night. Successful biotinylation of TNFR1-Fc and TNFR2-Fc was tested in standard binding ELISA to immobilized TNF. Bound receptor-Fc fusion proteins were detected by PolyHRP-Strep. ELISA was performed as described above.

Phage Display—Equilibrium Selection on Magnetic Dynabeads

In order to remove phages binding to human TNFR2 or the fused Fc moiety in a crossreactive manner, 1 µl or 10 µl of precipitated phages were added to 1 ml 2% MPBS, containing 0.1 µM human TNFR2-Fc and incubated rolling at RT for 1 hour. Subsequently, 50 µl of magnetic streptavidin-coated Dynabeads were added to the selection mix and rolled for another 5 minutes. Beads were then separated by placing the 2 ml reaction tube into an magnetic device (DYNAL® MPC®-S, Life Technologies, Carlsbad, Calif., USA), the selection mix was transferred to a new 2 ml reaction tube and human TNFR1-Fc was added to the selection mix (Round 1: 10 nM/1 nM, round 2: 1 nM/0.1 nM, round 3: 0.1 nM/0.01 nM). After incubation at RT (rolling for 1 hour), 10 µl Dynabeads were added to the selection mix and incubated and separated as described for the negative selection round with human TNFR2-Fc. The supernatant was discarded and 1 ml 10 mM DTT (Dithiotreitol) was added to the beads to release the bound phages from the antigen. Transduction was performed as described for the immunotube selection.

Phage Display—Polyclonal Phage ELISA

Changes in over all binding of the phage pool was tested by polyclonal phage ELISA. The experimental procedure is described in the ELISA section, here the antigen which was subject to phage display selection was used for coating. 10 µl of precipitated phages were mixed with 90 µl of 2% MPBS, applied to the microtiter plate and the bound phages were detected using an anti-M13-HRP antibody (27942101, GE Healthcare, Chalfont St Giles, GB).

Phage Display—Screening of Phage Display Selections

100 µl 2×TY LBamp per well of 1 to 4 microtiter plates were inoculated by single clones (100 to 400 colonies), which were picked from the plates after transduction of the final selection round and incubated shaking at 37° C. When clouding was visible, 25 µl LB containing VCS M13 helper phages (1 ml per microtiter plate) were added and incubated for transduction as described. Subsequently, 25 µl LB containing 240 µg/ml Kanamycin (final concentration 30 µg/ml) were added to the microtiter plate and the plate was incubated at 30° C., shaking over night. The next day, bacteria were separated by centrifugation (500*g, RT, 5 min) and the supernatants were mixed 1:1 with 2% MPBS and analyzed by ELISA as described in the polyclonal phage ELSIA, either in one point measurements or titrated.

Phage Display—Off-Rate Screening of Phage Containing Bacteria Culture Supernatants The dissociation rate constant of scFv-bearing phages was determined by off-rate screening, using the QCM technology. Phage rescue was performed similar to the described protocol, however, it was down scaled to a 5 ml LB culture. 100 µl of an overnight culture (or a purified scFv preparation) were used for inoculation and VSC M13 helper phages were added when the cultures showed visible clouding. The following steps were carried out as above mentioned. Without precipitation, phage containing supernatants were diluted 1:2 in PBST (0.1% Tween 20) and applied to a sensor chip, immobilized with huTNFR1-Fc at a moderate density of (48 Hz). The running buffer was mixed 1:1 with LB as well, to minimize buffer effects. The mean value of three measurements was analyzed using the Attaché office software (Attana, Stockholm, Sweden).

Coupling of Fab13.7 to Polyethylene Glycol

The cysteine modified Fab13.7 (Fab13.7') was coupled to metoxy-PEG40kDa2Maleimide (mPEG-Mal). The day before, proteins were reduced by adding TCEP (Tris(2-carboxyethyl)phosphin, f.c. 5 mM) and incubating for 2 hours at room temperature. Then TCEP was removed by dialysis in D-Tube™ Dialyzer Mini (MW cut-off 6-8 kDa) against nitrogen-saturated 1× Nellis buffer (10 mM Na2HPO4/NaH2PO4 buffer, 0.2 mM EDTA, 30 mM NaCl, pH 6.7) overnight at 4° C. using a magnetic stirrer. Reduced Fab13.7' was mixed with mPEG-Mal in a molar ration of 1:10 (protein:mPEG-Mal) and incubated for 1 hour at room temperature. In order to avoiding re-oxidation of Fab13.7', incubation was overlayed with nitrogen. Finally, free and reactive maleimide groups were quenched by adding L-cysteine (f.c. 100 µM) for 10 minutes at room temperature.

REFERENCES

Abhinandan K R, Martin A C. Analyzing the "degree of humanness" of antibody sequences. J Mol Biol. 2007 369(3):852-62.

Richter F, Liebig T, Guenzi E, Herrmann A, Scheurich P, Pfizenmaier K, Kontermann R E. Antagonistic TNF receptor one-specific antibody (ATROSAB): receptor binding and in vitro bioactivity. PLoS One. 2013 8(8): e72156. doi: 10.1371/journal.pone.0072156. eCollection 2013.

Zettlitz K A, Lorenz V, Landauer K, Münkel S, Herrmann A, Scheurich P, Pfizenmaier K, Kontermann R. ATROSAB, a humanized antagonistic anti-tumor necrosis factor receptor one-specific antibody. MAbs. 2010 2(6):639-47.

Armour K L, Clark M R, Hadley A G, Williamson L M. Recombinant human IgG molecules lacking Fcgamma receptor I binding and monocyte triggering activities. Eur J Immunol. 1999 August; 29(8):2613-24.

Choy E H, Hazleman B, Smith M, Moss K, Lisi L, Scott D G, Patel J, Sopwith M, Isenberg D A. Efficacy of a novel PEGylated humanized anti-TNF fragment (CDP870) in patients with rheumatoid arthritis: a phase II double-blinded, randomized, dose-escalating trial. Rheumatology (Oxford). 2002 October; 41(10):1133-7.

Gu J, Yang J, Chang Q, Liu Z, Ghayur T, Gu J. Identification of Anti-EGFR and Anti-ErbB3 Dual Variable Domains Immunoglobulin (DVD-Ig) Proteins with Unique Activities. PLoS One. 2015; 10(5): e0124135. Published online 2015 May 21. doi: 10.1371/journal.pone.0124135

Merchant M, Ma X, Maun H R, Zheng Z, Peng J, Romero M, Huang A, Yang N Y, Nishimura M, et al. Monovalent antibody design and mechanism of action of onartuzumab, a MET antagonist with anti-tumor activity as a therapeutic agent Proc Natl Acad Sci USA. 2013 Aug. 6; 110(32): E2987-E2996. Published online 2013 Jul. 23. doi: 10.1073/pnas.1302725110

Shields R L, Namenuk A K, Hong K, Meng Y G, Rae J, Briggs J, Xie D, Lai J, Stadlen A, Li B, Fox J A, Presta L G. High resolution mapping of the binding site on human IgG1 for Fc gamma RI, Fc gamma RII, Fc gamma RIII, and FcRn and design of IgG1 variants with improved binding to the Fc gamma R. J Biol Chem. 2001 Mar. 2; 276(9):6591-604. Epub 2000 Nov. 28.

The invention claimed is:

1. An inhibitor of the human tumor necrosis factor receptor 1 (huTNFR1) receptor which is a human or humanized antibody construct that monovalently recognizes huTNFR1 through an antigen-binding moiety, wherein the antigen-binding moiety comprises
a heavy chain variable (VH) domain that comprises the complementarity-determining regions (CDR) sequences CDRH1, CDRH2, and CDRH3, and
a light chain variable (VL) domain that comprises the CDR sequences CDRL1, CDRL2, and CDRL3, wherein:
a) the CDRH1 sequence is identified as SEQ ID NO: 1;
b) the CDRH2 sequence is identified as SEQ ID NO: 10;
c) the CDRH3 sequence is identified as SEQ ID NO: 3;
d) the CDRL1 sequence is identified as SEQ ID NO: 4;
e) the CDRL2 sequence is identified as SEQ ID NO: 5; and
f) the CDRL3 sequence is identified as SEQ ID NO: 11.

2. The inhibitor of claim 1, wherein the antibody construct comprises an antibody selected from the group consisting of Fab molecules, scFv molecules, disulfide-stabilized Fv (dsFv), half-IgG1 antibodies, and Fv domains.

3. The inhibitor of claim 2, wherein the antibody construct is any of a Fab, scFv, dsFv, or Fv domains, which is fused to an antibody Fc fragment, wherein the Fc.

4. The inhibitor of claim 1, wherein the antibody construct is modified by linkage to polyethylene glycol (PEGylation), glycosylated PEG, hydroxyl ethyl starch (HESylation), or poly-sialic acids (PSA).

5. The inhibitor of claim 1, wherein the VH domain is an affinity-matured variant of a parent VH domain identified as SEQ ID NO:12; and the VL domain is an affinity matured-variant of a parent VL domain identified as NO:SEQ ID 16.

6. The inhibitor of claim 1, wherein
a) the VH domain comprises or consists of SEQ ID NO: 13, or a functionally active variant thereof comprising at least 95% sequence identity to of any of SEQ ID NO: 13; and/or
b) the VL domain comprises or consists of a sequence selected from the group consisting of SEQ ID NO: 17 or SEQ ID NO: 19, or a functionally active variant thereof comprising at least 95% sequence identity to SEQ ID NO: 17 or SEQ ID NO: 19.

7. The inhibitor of claim 1,
comprising a combination of a VH and a VL domain, which is selected from the group consisting of group members i) to ii), wherein
i)
VH comprises or consists of SEQ ID NO: 13, and
VL comprises or consists of SEQ ID NO: 17;
and
ii)
VH comprises or consists of SEQ ID NO: 13, and
VL comprises or consists of SEQ ID NO: 19.

8. The inhibitor of claim 1, wherein the antibody construct has a thermostability of at least 60° C., as determined by dynamic light scattering.

9. A pharmaceutical preparation comprising the inhibitor of claim 1 and a pharmaceutically acceptable carrier.

10. The inhibitor of claim 1, for use in treating a human subject suffering from a disease where anti-tumor necrosis factor (TNF) therapies or non-biologic disease-modifying anti-rheumatic drugs (DMARD) are indicated.

11. The inhibitor for use according to claim 10, wherein the subject has developed anti-drug antibodies.

12. The inhibitor for use according to claim 10, wherein the subject is suffering from
a) acute or chronic inflammation of joints, skin and gut; and/or
b) autoimmune diseases, rheumatoid arthritis, psoriasis, psoriatic arthritis, juvenile arthritis, ankylosing spondylitis, Crohn's disease, multiple sclerosis, congestive heart failure, metabolic disease, cytokine release syndrome, septic shock, acute and chronic neurodegenerative disease, stroke, Alzheimer's and Parkinson's disease, colitis ulcerosa, pancreatitis, chronic obstructive pulmonary disease (COPD), acute fulminant viral or bacterial infections, metabolic diseases, chronic neurodegenerative diseases, genetically inherited diseases with TNF/TNFR1 as the causative pathologic mediator, periodic fever syndrome, cherubism, and cancer.

13. The pharmaceutical preparation of claim 9, wherein the preparation is formulated for parenteral use.

14. The pharmaceutical preparation of claim 13, wherein the parenteral use is by intravenous or subcutaneous administration.

15. The inhibitor of claim 10, which is for use as first-line treatment, or as second-line treatment where anti-TNF or non-biologic DMARD therapeutics failed.

16. An isolated nucleic acid encoding the inhibitor of claim 1.

17. An expression vector comprising the nucleic acid of claim 16.

18. A isolated recombinant host cell comprising the nucleic acid of claim 16.

19. A method of producing an inhibitor by employing a recombinant mammalian expression system to express the antibody construct.

20. The method of claim 19, wherein a Chinese Hamster Ovary (CHO) production cell line is employed.

21. A method of treating a human subject in need of an anti-TNF therapy, by administering an effective amount of the inhibitor of claim 1.

22. The method of claim 21, wherein the subject is suffering from a disease where anti-TNF therapies or non-biologic DMARD therapeutics are indicated, preferably as first line treatment, or as second line treatment where anti-TNF or non-biologic DMARD therapeutics failed.

23. The method of claim 21, wherein the subject has developed anti-drug antibodies.

24. The method of claim 21, wherein the subject is suffering from
   a) acute or chronic inflammation of joints, skin and gut; and/or
   b) autoimmune diseases, rheumatoid arthritis, psoriasis, psoriatic arthritis, juvenile arthritis, ankylosing spondylitis, Crohn's disease, multiple sclerosis, congestive heart failure, metabolic disease, cytokine release syndrome, septic shock, acute and chronic neurodegenerative disease, stroke, Alzheimer's and Parkinson's disease, colitis ulcerosa, pancreatitis, COPD, acute fulminant viral or bacterial infections, metabolic diseases, chronic neurodegenerative diseases, genetically inherited diseases with TNF/TNFR1 as the causative pathologic mediator, periodic fever syndrome, cherubism, and cancer.

* * * * *

UNITED STATES PATENT AND TRADEMARK OFFICE
CERTIFICATE OF CORRECTION

PATENT NO. : 10,689,452 B2
APPLICATION NO. : 16/091456
DATED : June 23, 2020
INVENTOR(S) : Roland Kontermann et al.

Page 1 of 1

It is certified that error appears in the above-identified patent and that said Letters Patent is hereby corrected as shown below:

In the Claims

In Column 104, Line 55, Claim 19, insert --of claim 1-- after "inhibitor".

Signed and Sealed this
Fourth Day of August, 2020

Andrei Iancu
*Director of the United States Patent and Trademark Office*

SEQUENCE LISTING

<160> NUMBER OF SEQ ID NOS: 44

<210> SEQ ID NO 1
<211> LENGTH: 5
<212> TYPE: PRT
<213> ORGANISM: Artificial Sequence
<220> FEATURE:
<223> OTHER INFORMATION: CDR Sequence

<400> SEQUENCE: 1

Asp Phe Tyr Ile Asn
1               5

<210> SEQ ID NO 2
<211> LENGTH: 17
<212> TYPE: PRT
<213> ORGANISM: Artificial Sequence
<220> FEATURE:
<223> OTHER INFORMATION: CDR Sequence

<400> SEQUENCE: 2

Glu Ile Tyr Pro Tyr Ser Gly His Ala Tyr Tyr Asn Glu Lys Phe Lys
1               5                   10                  15

Ala

<210> SEQ ID NO 3
<211> LENGTH: 6
<212> TYPE: PRT
<213> ORGANISM: Artificial Sequence
<220> FEATURE:
<223> OTHER INFORMATION: CDR Sequence

<400> SEQUENCE: 3

```
Trp Asp Phe Leu Asp Tyr
1               5

<210> SEQ ID NO 4
<211> LENGTH: 16
<212> TYPE: PRT
<213> ORGANISM: Artificial Sequence
<220> FEATURE:
<223> OTHER INFORMATION: CDR Sequence

<400> SEQUENCE: 4

Arg Ser Ser Gln Ser Leu Leu His Ser Asn Gly Asn Thr Tyr Leu His
1               5                   10                  15

<210> SEQ ID NO 5
<211> LENGTH: 7
<212> TYPE: PRT
<213> ORGANISM: Artificial Sequence
<220> FEATURE:
<223> OTHER INFORMATION: CDR Sequence

<400> SEQUENCE: 5

Thr Val Ser Asn Arg Phe Ser
1               5

<210> SEQ ID NO 6
<211> LENGTH: 9
<212> TYPE: PRT
<213> ORGANISM: Artificial Sequence
<220> FEATURE:
<223> OTHER INFORMATION: CDR Sequence

<400> SEQUENCE: 6

Ser Gln Ser Thr His Val Pro Tyr Thr
1               5

<210> SEQ ID NO 7
<211> LENGTH: 17
<212> TYPE: PRT
<213> ORGANISM: Artificial Sequence
<220> FEATURE:
<223> OTHER INFORMATION: CDR Sequence
<220> FEATURE:
<221> NAME/KEY: MISC_FEATURE
<222> LOCATION: (3)..(3)
<223> OTHER INFORMATION: X is any of Y or V
<220> FEATURE:
<221> NAME/KEY: MISC_FEATURE
<222> LOCATION: (5)..(5)
<223> OTHER INFORMATION: X is any of Y, T or S
<220> FEATURE:
<221> NAME/KEY: MISC_FEATURE
<222> LOCATION: (6)..(6)
<223> OTHER INFORMATION: X is any of S or Q
<220> FEATURE:
<221> NAME/KEY: MISC_FEATURE
<222> LOCATION: (8)..(8)
<223> OTHER INFORMATION: X is any of H or E
<220> FEATURE:
<221> NAME/KEY: MISC_FEATURE
<222> LOCATION: (10)..(10)
<223> OTHER INFORMATION: X is any of Y or K
<220> FEATURE:
<221> NAME/KEY: MISC_FEATURE
<222> LOCATION: (13)..(13)
<223> OTHER INFORMATION: X is any of E or D

<400> SEQUENCE: 7

Glu Ile Xaa Pro Xaa Xaa Gly Xaa Ala Xaa Tyr Asn Xaa Lys Phe Lys
1               5                   10                  15
```

Ala

```
<210> SEQ ID NO 8
<211> LENGTH: 9
<212> TYPE: PRT
<213> ORGANISM: Artificial Sequence
<220> FEATURE:
<223> OTHER INFORMATION: CDR Sequence
<220> FEATURE:
<221> NAME/KEY: MISC_FEATURE
<222> LOCATION: (3)..(3)
<223> OTHER INFORMATION: X is any of S or G

<400> SEQUENCE: 8

Ser Gln Xaa Thr His Val Pro Tyr Thr
1               5

<210> SEQ ID NO 9
<211> LENGTH: 17
<212> TYPE: PRT
<213> ORGANISM: Artificial Sequence
<220> FEATURE:
<223> OTHER INFORMATION: CDR Sequence

<400> SEQUENCE: 9

Glu Ile Val Pro Thr Gln Gly Glu Ala Lys Tyr Asn Asp Lys Phe Lys
1               5                   10                  15

Ala

<210> SEQ ID NO 10
<211> LENGTH: 17
<212> TYPE: PRT
<213> ORGANISM: Artificial Sequence
<220> FEATURE:
<223> OTHER INFORMATION: CDR Sequence
<220> FEATURE:
<221> NAME/KEY: MISC_FEATURE
<222> LOCATION: (5)..(5)
<223> OTHER INFORMATION: X is any of S or G

<400> SEQUENCE: 10

Glu Ile Val Pro Xaa Gln Gly Glu Ala Lys Tyr Asn Asp Lys Phe Lys
1               5                   10                  15

Ala

<210> SEQ ID NO 11
<211> LENGTH: 9
<212> TYPE: PRT
<213> ORGANISM: Artificial Sequence
<220> FEATURE:
<223> OTHER INFORMATION: CDR Sequence
<220> FEATURE:
<221> NAME/KEY: MISC_FEATURE
<222> LOCATION: (3)..(3)
<223> OTHER INFORMATION: X is any of G or S

<400> SEQUENCE: 11

Ser Gln Xaa Thr His Val Pro Tyr Thr
1               5

<210> SEQ ID NO 12
<211> LENGTH: 115
<212> TYPE: PRT
<213> ORGANISM: Artificial Sequence
<220> FEATURE:
<223> OTHER INFORMATION: VH Sequence

<400> SEQUENCE: 12
```

```
Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Asp Phe
            20                  25                  30

Tyr Ile Asn Trp Val Arg Gln Ala Pro Gly Gln Gly Leu Glu Trp Ile
        35                  40                  45

Gly Glu Ile Val Pro Thr Gln Gly Glu Ala Lys Tyr Asn Asp Lys Phe
    50                  55                  60

Lys Ala Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Trp Asp Phe Leu Asp Tyr Trp Gly Gln Gly Thr Thr Val Thr
                100                 105                 110

Val Ser Ser
        115

<210> SEQ ID NO 13
<211> LENGTH: 115
<212> TYPE: PRT
<213> ORGANISM: Artificial Sequence
<220> FEATURE:
<223> OTHER INFORMATION: VH Sequence

<400> SEQUENCE: 13

His Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Asp Phe
            20                  25                  30

Tyr Ile Asn Trp Val Arg Gln Ala Pro Gly Gln Gly Leu Glu Trp Ile
        35                  40                  45

Gly Glu Ile Val Pro Ser Gln Gly Glu Ala Lys Tyr Asn Asp Lys Phe
    50                  55                  60

Lys Ala Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Trp Asp Phe Leu Asp Tyr Trp Gly Gln Gly Thr Thr Val Thr
                100                 105                 110

Val Ser Ser
        115

<210> SEQ ID NO 14
<211> LENGTH: 115
<212> TYPE: PRT
<213> ORGANISM: Artificial Sequence
<220> FEATURE:
<223> OTHER INFORMATION: VH Sequence

<400> SEQUENCE: 14

Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Phe
            20                  25                  30

Tyr Ile Asn Trp Ile Arg Gln Ala Pro Gly Lys Gly Leu Glu Trp Val
        35                  40                  45

Ser Glu Ile Tyr Pro Tyr Ser Gly His Ala Tyr Tyr Asn Glu Lys Phe
```

```
                    50                  55                  60
Lys Ala Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                     85                  90                  95

Ala Arg Trp Asp Phe Leu Asp Tyr Trp Gly Gln Gly Thr Thr Val Thr
                100                 105                 110

Val Ser Ser
        115

<210> SEQ ID NO 15
<211> LENGTH: 115
<212> TYPE: PRT
<213> ORGANISM: Artificial Sequence
<220> FEATURE:
<223> OTHER INFORMATION: VH Sequence

<400> SEQUENCE: 15

Gln Val Gln Leu Val Glu Ser Gly Gly Gly Leu Val Lys Pro Gly Gly
  1               5                  10                  15

Ser Leu Arg Leu Ser Cys Ala Ala Ser Gly Phe Thr Phe Ser Asp Phe
                 20                  25                  30

Tyr Ile Asn Trp Ile Arg Gln Ala Pro Gly Lys Gly Leu Glu Trp Val
                 35                  40                  45

Ser Glu Ile Tyr Pro Tyr Ser Gly His Ala Tyr Tyr Asn Glu Lys Phe
     50                  55                  60

Lys Ala Arg Phe Thr Ile Ser Ala Asp Asn Ala Lys Asn Ser Leu Tyr
 65                  70                  75                  80

Leu Gln Met Asn Ser Leu Arg Ala Glu Asp Thr Ala Val Tyr Tyr Cys
                     85                  90                  95

Ala Arg Trp Asp Phe Leu Asp Tyr Trp Gly Gln Gly Thr Thr Val Thr
                100                 105                 110

Val Ser Ser
        115

<210> SEQ ID NO 16
<211> LENGTH: 113
<212> TYPE: PRT
<213> ORGANISM: Artificial Sequence
<220> FEATURE:
<223> OTHER INFORMATION: VL Sequence

<400> SEQUENCE: 16

Asp Ile Val Met Thr Gln Ser Pro Leu Ser Leu Pro Val Thr Pro Gly
  1               5                  10                  15

Glu Pro Ala Ser Ile Ser Cys Arg Ser Ser Gln Ser Leu Leu His Ser
                 20                  25                  30

Asn Gly Asn Thr Tyr Leu His Trp Tyr Leu Gln Lys Pro Gly Gln Ser
                 35                  40                  45

Pro Gln Leu Leu Ile Tyr Thr Val Ser Asn Arg Phe Ser Gly Val Pro
     50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Ser Gln Ser
                     85                  90                  95

Thr His Val Pro Tyr Thr Phe Gly Gly Gly Thr Lys Val Glu Ile Lys
                100                 105                 110
```

Arg

<210> SEQ ID NO 17
<211> LENGTH: 113
<212> TYPE: PRT
<213> ORGANISM: Artificial Sequence
<220> FEATURE:
<223> OTHER INFORMATION: VL Sequence

<400> SEQUENCE: 17

```
Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Asn Thr Tyr Leu His Trp Tyr Leu Gln Lys Pro Gly Gln Ser
        35                  40                  45

Pro Gln Leu Leu Ile Tyr Thr Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Gly
                85                  90                  95

Thr His Val Pro Tyr Thr Phe Gly Gly Gly Thr Lys Val Glu Ile Lys
            100                 105                 110

Arg
```

<210> SEQ ID NO 18
<211> LENGTH: 112
<212> TYPE: PRT
<213> ORGANISM: Artificial Sequence
<220> FEATURE:
<223> OTHER INFORMATION: VL Sequence

<400> SEQUENCE: 18

```
Asp Ile Gln Met Thr Gln Ser Pro Ser Ser Leu Ser Ala Ser Val Gly
1               5                   10                  15

Asp Arg Val Thr Ile Thr Cys Arg Ser Ser Gln Ser Leu Leu His Ser
            20                  25                  30

Asn Gly Asn Thr Tyr Leu His Trp Tyr Gln Gln Lys Pro Gly Lys Ala
        35                  40                  45

Pro Lys Leu Leu Ile Tyr Thr Val Ser Asn Arg Phe Ser Gly Val Pro
    50                  55                  60

Ser Arg Phe Ser Gly Ser Gly Ser Gly Thr Asp Phe Thr Leu Thr Ile
65                  70                  75                  80

Ser Ser Leu Gln Pro Glu Asp Phe Ala Thr Tyr Tyr Cys Ser Gln Ser
                85                  90                  95

Thr His Val Pro Tyr Thr Phe Gly Gly Gly Thr Lys Val Glu Ile Lys
            100                 105                 110
```

<210> SEQ ID NO 19
<211> LENGTH: 112
<212> TYPE: PRT
<213> ORGANISM: Artificial Sequence
<220> FEATURE:
<223> OTHER INFORMATION: VL Sequence

<400> SEQUENCE: 19

```
Asp Val Gln Met Thr Gln Ser Pro Ser Ser Leu Ser Ala Ser Val Gly
1               5                   10                  15
```

```
Asp Arg Val Thr Ile Thr Cys Arg Ser Ser Gln Ser Leu Leu His Ser
                20                  25                  30

Asn Gly Asn Thr Tyr Leu His Trp Tyr Gln Gln Lys Pro Gly Lys Ala
         35                  40                  45

Pro Lys Leu Leu Ile Tyr Thr Val Ser Asn Arg Phe Ser Gly Val Pro
     50                  55                  60

Ser Arg Phe Ser Gly Ser Gly Ser Gly Thr Asp Phe Thr Leu Thr Ile
 65                  70                  75                  80

Ser Ser Leu Gln Pro Glu Asp Phe Ala Thr Tyr Tyr Cys Ser Gln Ser
                 85                  90                  95

Thr His Val Pro Tyr Thr Phe Gly Gly Gly Thr Lys Val Glu Ile Lys
                100                 105                 110

<210> SEQ ID NO 20
<211> LENGTH: 115
<212> TYPE: PRT
<213> ORGANISM: Artificial Sequence
<220> FEATURE:
<223> OTHER INFORMATION: VH Sequence

<400> SEQUENCE: 20

Gln Val Gln Leu Val Gln Ser Gly Ala Glu Val Lys Lys Pro Gly Ser
 1               5                  10                  15

Ser Val Lys Val Ser Cys Lys Ala Ser Gly Tyr Thr Phe Thr Asp Phe
                20                  25                  30

Tyr Ile Asn Trp Val Arg Gln Ala Pro Gly Gln Gly Leu Glu Trp Ile
         35                  40                  45

Gly Glu Ile Tyr Pro Tyr Ser Gly His Ala Tyr Tyr Asn Glu Lys Phe
 50                  55                  60

Lys Ala Arg Val Thr Ile Thr Ala Asp Lys Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Trp Asp Phe Leu Asp Tyr Trp Gly Gln Gly Thr Thr Val Thr
                100                 105                 110

Val Ser Ser
        115

<210> SEQ ID NO 21
<211> LENGTH: 113
<212> TYPE: PRT
<213> ORGANISM: Artificial Sequence
<220> FEATURE:
<223> OTHER INFORMATION: VL Sequence

<400> SEQUENCE: 21

Asp Ile Val Met Thr Gln Ser Pro Leu Ser Leu Pro Val Thr Pro Gly
 1               5                  10                  15

Glu Pro Ala Ser Ile Ser Cys Arg Ser Ser Gln Ser Leu Leu His Ser
                20                  25                  30

Asn Gly Asn Thr Tyr Leu His Trp Tyr Leu Gln Lys Pro Gly Gln Ser
         35                  40                  45

Pro Gln Leu Leu Ile Tyr Thr Val Ser Asn Arg Phe Ser Gly Val Pro
     50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Ser Gln Ser
                 85                  90                  95
```

Thr His Val Pro Tyr Thr Phe Gly Gly Gly Thr Lys Val Glu Ile Lys
                100                 105                 110
Arg

<210> SEQ ID NO 22
<211> LENGTH: 115
<212> TYPE: PRT
<213> ORGANISM: Artificial Sequence
<220> FEATURE:
<223> OTHER INFORMATION: VH Sequence

<400> SEQUENCE: 22

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Asp Phe
            20                  25                  30

Tyr Ile Asn Trp Val Arg Gln Ala Pro Gly Gln Gly Leu Glu Trp Ile
        35                  40                  45

Gly Glu Ile Tyr Pro Tyr Ser Gly His Ala Tyr Tyr Asn Glu Lys Phe
    50                  55                  60

Lys Ala Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Trp Asp Phe Leu Asp Tyr Trp Gly Gln Gly Thr Thr Val Thr
            100                 105                 110

Val Ser Ser
        115

<210> SEQ ID NO 23
<211> LENGTH: 113
<212> TYPE: PRT
<213> ORGANISM: Artificial Sequence
<220> FEATURE:
<223> OTHER INFORMATION: VL Sequence

<400> SEQUENCE: 23

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Asn Thr Tyr Leu His Trp Tyr Leu Gln Lys Pro Gly Gln Ser
        35                  40                  45

Pro Gln Leu Leu Ile Tyr Thr Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Ser
                85                  90                  95

Thr His Val Pro Tyr Thr Phe Gly Gly Gly Thr Lys Val Glu Ile Lys
            100                 105                 110

Arg

<210> SEQ ID NO 24
<211> LENGTH: 227
<212> TYPE: PRT
<213> ORGANISM: Artificial Sequence
<220> FEATURE:

<223> OTHER INFORMATION: human IgG Fc sequence

<400> SEQUENCE: 24

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Asp Glu Leu Thr Lys Asn Gln Val Ser
    130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Lys
225

<210> SEQ ID NO 25
<211> LENGTH: 218
<212> TYPE: PRT
<213> ORGANISM: Artificial Sequence
<220> FEATURE:
<223> OTHER INFORMATION: Heavy chain sequence

<400> SEQUENCE: 25

His Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Asp Phe
            20                  25                  30

Tyr Ile Asn Trp Val Arg Gln Ala Pro Gly Gln Gly Leu Glu Trp Ile
        35                  40                  45

Gly Glu Ile Val Pro Ser Gln Gly Glu Ala Lys Tyr Asn Asp Lys Phe
    50                  55                  60

Lys Ala Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Trp Asp Phe Leu Asp Tyr Trp Gly Gln Gly Thr Thr Val Thr
            100                 105                 110

Val Ser Ser Ala Ser Thr Lys Gly Pro Ser Val Phe Pro Leu Ala Pro
            115                 120                 125

Ser Ser Lys Ser Thr Ser Gly Gly Thr Ala Ala Leu Gly Cys Leu Val
        130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
                180                 185                 190

Thr Gln Thr Tyr Ile Cys Asn Val Asn His Lys Pro Ser Asn Thr Lys
            195                 200                 205

Val Asp Lys Lys Val Glu Pro Lys Ser Cys
        210                 215

<210> SEQ ID NO 26
<211> LENGTH: 219
<212> TYPE: PRT
<213> ORGANISM: Artificial Sequence
<220> FEATURE:
<223> OTHER INFORMATION: Light chain sequence

<400> SEQUENCE: 26

Asp Val Gln Met Thr Gln Ser Pro Ser Ser Leu Ser Ala Ser Val Gly
1               5                   10                  15

Asp Arg Val Thr Ile Thr Cys Arg Ser Ser Gln Ser Leu Leu His Ser
            20                  25                  30

Asn Gly Asn Thr Tyr Leu His Trp Tyr Gln Gln Lys Pro Gly Lys Ala
        35                  40                  45

Pro Lys Leu Leu Ile Tyr Thr Val Ser Asn Arg Phe Ser Gly Val Pro
    50                  55                  60

Ser Arg Phe Ser Gly Ser Gly Ser Gly Thr Asp Phe Thr Leu Thr Ile
65                  70                  75                  80

Ser Ser Leu Gln Pro Glu Asp Phe Ala Thr Tyr Tyr Cys Ser Gln Ser
                85                  90                  95

Thr His Val Pro Tyr Thr Phe Gly Gly Gly Thr Lys Val Glu Ile Lys
            100                 105                 110

Arg Thr Val Ala Ala Pro Ser Val Phe Ile Phe Pro Pro Ser Asp Glu
            115                 120                 125

Gln Leu Lys Ser Gly Thr Ala Ser Val Val Cys Leu Leu Asn Asn Phe
        130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
                180                 185                 190

Lys His Lys Val Tyr Ala Cys Glu Val Thr His Gln Gly Leu Ser Ser
            195                 200                 205

Pro Val Thr Lys Ser Phe Asn Arg Gly Glu Cys
        210                 215

<210> SEQ ID NO 27
<211> LENGTH: 226
<212> TYPE: PRT
<213> ORGANISM: Artificial Sequence
<220> FEATURE:
<223> OTHER INFORMATION: Heavy chain sequence

<400> SEQUENCE: 27

```
His Val Gln Leu Val Gln Ser Gly Ala Glu Val Lys Lys Pro Gly Ser
 1               5                  10                  15

Ser Val Lys Val Ser Cys Lys Ala Ser Gly Tyr Thr Phe Thr Asp Phe
             20                  25                  30

Tyr Ile Asn Trp Val Arg Gln Ala Pro Gly Gln Gly Leu Glu Trp Ile
         35                  40                  45

Gly Glu Ile Val Pro Ser Gln Gly Glu Ala Lys Tyr Asn Asp Lys Phe
     50                  55                  60

Lys Ala Arg Val Thr Ile Thr Ala Asp Lys Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Trp Asp Phe Leu Asp Tyr Trp Gly Gln Gly Thr Thr Val Thr
            100                 105                 110

Val Ser Ser Ala Ser Thr Lys Gly Pro Ser Val Phe Pro Leu Ala Pro
        115                 120                 125

Ser Ser Lys Ser Thr Ser Gly Gly Thr Ala Ala Leu Gly Cys Leu Val
    130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys
        195                 200                 205

Val Asp Lys Lys Val Glu Pro Lys Ser Cys Asp Lys Thr His Thr Cys
    210                 215                 220

Ala Ala
225
```

<210> SEQ ID NO 28
<211> LENGTH: 817
<212> TYPE: PRT
<213> ORGANISM: Artificial Sequence
<220> FEATURE:
<223> OTHER INFORMATION: Heavy chain sequence

<400> SEQUENCE: 28

```
His Val Gln Leu Val Gln Ser Gly Ala Glu Val Lys Lys Pro Gly Ser
 1               5                  10                  15

Ser Val Lys Val Ser Cys Lys Ala Ser Gly Tyr Thr Phe Thr Asp Phe
             20                  25                  30

Tyr Ile Asn Trp Val Arg Gln Ala Pro Gly Gln Gly Leu Glu Trp Ile
         35                  40                  45

Gly Glu Ile Val Pro Ser Gln Gly Glu Ala Lys Tyr Asn Asp Lys Phe
     50                  55                  60

Lys Ala Arg Val Thr Ile Thr Ala Asp Lys Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Trp Asp Phe Leu Asp Tyr Trp Gly Gln Gly Thr Thr Val Thr
```

```
                100                 105                 110
Val Ser Ser Ala Ser Thr Lys Gly Pro Ser Val Phe Pro Leu Ala Pro
            115                 120                 125

Ser Ser Lys Ser Thr Ser Gly Gly Thr Ala Ala Leu Gly Cys Leu Val
        130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys
        195                 200                 205

Val Asp Lys Lys Val Glu Pro Lys Ser Cys Gly Gly Gly Gly Ser Gly
210                 215                 220

Gly Gly Ser Ser Leu Glu Ala His Lys Ser Glu Ile Ala His Arg
225                 230                 235                 240

Tyr Asn Asp Leu Gly Glu Gln His Phe Lys Gly Leu Val Leu Ile Ala
                245                 250                 255

Phe Ser Gln Tyr Leu Gln Lys Cys Ser Tyr Asp Glu His Ala Lys Leu
            260                 265                 270

Val Gln Glu Val Thr Asp Phe Ala Lys Thr Cys Val Ala Asp Glu Ser
        275                 280                 285

Ala Ala Asn Cys Asp Lys Ser Leu His Thr Leu Phe Gly Asp Lys Leu
290                 295                 300

Cys Ala Ile Pro Asn Leu Arg Glu Asn Tyr Gly Glu Leu Ala Asp Cys
305                 310                 315                 320

Cys Thr Lys Gln Glu Pro Glu Arg Asn Glu Cys Phe Leu Gln His Lys
                325                 330                 335

Asp Asp Asn Pro Ser Leu Pro Pro Phe Glu Arg Pro Glu Ala Glu Ala
            340                 345                 350

Met Cys Thr Ser Phe Lys Glu Asn Pro Thr Thr Phe Met Gly His Tyr
        355                 360                 365

Leu His Glu Val Ala Arg Arg His Pro Tyr Phe Tyr Ala Pro Glu Leu
370                 375                 380

Leu Tyr Tyr Ala Glu Gln Tyr Asn Glu Ile Leu Thr Gln Cys Cys Ala
385                 390                 395                 400

Glu Ala Asp Lys Glu Ser Cys Leu Thr Pro Lys Leu Asp Gly Val Lys
                405                 410                 415

Glu Lys Ala Leu Val Ser Ser Val Arg Gln Arg Met Lys Cys Ser Ser
            420                 425                 430

Met Gln Lys Phe Gly Glu Arg Ala Phe Lys Ala Trp Ala Val Ala Arg
        435                 440                 445

Leu Ser Gln Thr Phe Pro Asn Ala Asp Phe Ala Glu Ile Thr Lys Leu
450                 455                 460

Ala Thr Asp Leu Thr Lys Val Asn Lys Glu Cys Cys His Gly Asp Leu
465                 470                 475                 480

Leu Glu Cys Ala Asp Asp Arg Ala Glu Leu Ala Lys Tyr Met Cys Glu
                485                 490                 495

Asn Gln Ala Thr Ile Ser Ser Lys Leu Gln Thr Cys Cys Asp Lys Pro
            500                 505                 510

Leu Leu Lys Lys Ala His Cys Leu Ser Glu Val Glu His Asp Thr Met
        515                 520                 525
```

Pro Ala Asp Leu Pro Ala Ile Ala Asp Phe Val Glu Asp Gln Glu
    530                 535                 540

Val Cys Lys Asn Tyr Ala Glu Ala Lys Asp Val Phe Leu Gly Thr Phe
545                 550                 555                 560

Leu Tyr Glu Tyr Ser Arg Arg His Pro Asp Tyr Ser Val Ser Leu Leu
            565                 570                 575

Leu Arg Leu Ala Lys Lys Tyr Glu Ala Thr Leu Glu Lys Cys Cys Ala
        580                 585                 590

Glu Ala Asn Pro Pro Ala Cys Tyr Gly Thr Val Leu Ala Glu Phe Gln
        595                 600                 605

Pro Leu Val Glu Glu Pro Lys Asn Leu Val Lys Thr Asn Cys Asp Leu
    610                 615                 620

Tyr Glu Lys Leu Gly Glu Tyr Gly Phe Gln Asn Ala Ile Leu Val Arg
625                 630                 635                 640

Tyr Thr Gln Lys Ala Pro Gln Val Ser Thr Pro Thr Leu Val Glu Ala
            645                 650                 655

Ala Arg Asn Leu Gly Arg Val Gly Thr Lys Cys Cys Thr Leu Pro Glu
        660                 665                 670

Asp Gln Arg Leu Pro Cys Val Glu Asp Tyr Leu Ser Ala Ile Leu Asn
        675                 680                 685

Arg Val Cys Leu Leu His Glu Lys Thr Pro Val Ser Glu His Val Thr
690                 695                 700

Lys Cys Cys Ser Gly Ser Leu Val Glu Arg Arg Pro Cys Phe Ser Ala
705                 710                 715                 720

Leu Thr Val Asp Glu Thr Tyr Val Pro Lys Glu Phe Lys Ala Glu Thr
            725                 730                 735

Phe Thr Phe His Ser Asp Ile Cys Thr Leu Pro Glu Lys Glu Lys Gln
        740                 745                 750

Ile Lys Lys Gln Thr Ala Leu Ala Glu Leu Val Lys His Lys Pro Lys
        755                 760                 765

Ala Thr Ala Glu Gln Leu Lys Thr Val Met Asp Asp Phe Ala Gln Phe
    770                 775                 780

Leu Asp Thr Cys Cys Lys Ala Ala Asp Lys Asp Thr Cys Phe Ser Thr
785                 790                 795                 800

Glu Gly Pro Asn Leu Val Gly Gly Ala Ala His His His His
            805                 810                 815

His

<210> SEQ ID NO 29
<211> LENGTH: 445
<212> TYPE: PRT
<213> ORGANISM: Artificial Sequence
<220> FEATURE:
<223> OTHER INFORMATION: Heavy chain sequence

<400> SEQUENCE: 29

His Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Asp Phe
            20                  25                  30

Tyr Ile Asn Trp Val Arg Gln Ala Pro Gly Gln Gly Leu Glu Trp Ile
        35                  40                  45

Gly Glu Ile Val Pro Ser Gln Gly Glu Ala Lys Tyr Asn Asp Lys Phe
    50                  55                  60

```
Lys Ala Arg Val Thr Ile Thr Ala Asp Lys Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Trp Asp Phe Leu Asp Tyr Trp Gly Gln Gly Thr Thr Val Thr
            100                 105                 110

Val Ser Ser Ala Ser Thr Lys Gly Pro Ser Val Phe Pro Leu Ala Pro
        115                 120                 125

Ser Ser Lys Ser Thr Ser Gly Gly Thr Ala Ala Leu Gly Cys Leu Val
    130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys
        195                 200                 205

Val Asp Lys Lys Val Glu Pro Lys Ser Cys Asp Lys Thr His Thr Ser
    210                 215                 220

Pro Pro Ser Pro Ala Pro Glu Leu Leu Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser His Glu Asp Pro Glu Val Lys
            260                 265                 270

Phe Asn Trp Tyr Val Asp Gly Val Glu Val His Asn Ala Lys Thr Lys
        275                 280                 285

Pro Arg Glu Glu Gln Tyr Asn Ser Thr Tyr Arg Val Val Ser Val Leu
    290                 295                 300

Thr Val Leu His Gln Asp Trp Leu Asn Gly Lys Glu Tyr Lys Cys Lys
305                 310                 315                 320

Val Ser Asn Lys Ala Leu Pro Ala Pro Ile Glu Lys Thr Ile Ser Lys
                325                 330                 335

Ala Lys Gly Gln Pro Arg Glu Pro Gln Val Tyr Thr Leu Pro Pro Ser
            340                 345                 350

Arg Asp Glu Leu Thr Lys Asn Gln Val Ser Leu Thr Cys Leu Val Lys
        355                 360                 365

Gly Phe Tyr Pro Ser Asp Ile Ala Val Glu Trp Glu Ser Asn Gly Gln
    370                 375                 380

Pro Glu Asn Asn Tyr Lys Thr Thr Pro Val Leu Asp Ser Asp Gly
385                 390                 395                 400

Ser Phe Arg Leu Arg Ser Asp Leu Thr Val Asp Lys Ser Arg Trp Gln
                405                 410                 415

Gln Gly Asn Val Phe Ser Cys Ser Val Met His Glu Ala Leu His Asn
            420                 425                 430

His Tyr Thr Gln Lys Ser Leu Ser Leu Ser Pro Gly Lys
        435                 440                 445

<210> SEQ ID NO 30
<211> LENGTH: 446
<212> TYPE: PRT
<213> ORGANISM: Artificial Sequence
<220> FEATURE:
<223> OTHER INFORMATION: Fd sequence
```

<400> SEQUENCE: 30

His Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Asp Phe
            20                  25                  30

Tyr Ile Asn Trp Val Arg Gln Ala Pro Gly Gln Gly Leu Glu Trp Ile
        35                  40                  45

Gly Glu Ile Val Pro Ser Gln Gly Glu Ala Lys Tyr Asn Asp Lys Phe
    50                  55                  60

Lys Ala Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Trp Asp Phe Leu Asp Tyr Trp Gly Gln Gly Thr Thr Val Thr
            100                 105                 110

Val Ser Ser Ala Ser Thr Lys Gly Pro Ser Val Phe Pro Leu Ala Pro
        115                 120                 125

Ser Ser Lys Ser Thr Ser Gly Gly Thr Ala Ala Leu Gly Cys Leu Val
    130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys
        195                 200                 205

Val Asp Lys Lys Val Glu Pro Lys Ser Cys Gly Thr Asp Lys Thr His
    210                 215                 220

Thr Ser Pro Pro Ser Pro Ala Pro Pro Val Ala Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Gly Leu Pro Ser Ser Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Asp Glu Leu Thr Lys Asn Gln Val Ser Leu Ser Cys Ala Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400

Gly Ser Phe Phe Leu Val Ser Lys Leu Thr Val Asp Lys Ser Arg Trp

```
                    405                 410                 415
Gln Gln Gly Asn Val Phe Ser Cys Ser Val Met His Glu Ala Leu His
            420                 425                 430
Asn His Tyr Thr Gln Lys Ser Leu Ser Leu Ser Pro Gly Lys
            435                 440                 445

<210> SEQ ID NO 31
<211> LENGTH: 447
<212> TYPE: PRT
<213> ORGANISM: Artificial Sequence
<220> FEATURE:
<223> OTHER INFORMATION: LC sequence

<400> SEQUENCE: 31

Asp Val Gln Met Thr Gln Ser Pro Ser Ser Leu Ser Ala Ser Val Gly
1               5                   10                  15
Asp Arg Val Thr Ile Thr Cys Arg Ser Ser Gln Ser Leu Leu His Ser
            20                  25                  30
Asn Gly Asn Thr Tyr Leu His Trp Tyr Gln Gln Lys Pro Gly Lys Ala
        35                  40                  45
Pro Lys Leu Leu Ile Tyr Thr Val Ser Asn Arg Phe Ser Gly Val Pro
    50                  55                  60
Ser Arg Phe Ser Gly Ser Gly Ser Gly Thr Asp Phe Thr Leu Thr Ile
65                  70                  75                  80
Ser Ser Leu Gln Pro Glu Asp Phe Ala Thr Tyr Tyr Cys Ser Gln Ser
                85                  90                  95
Thr His Val Pro Tyr Thr Phe Gly Gly Gly Thr Lys Val Glu Ile Lys
            100                 105                 110
Arg Thr Val Ala Ala Pro Ser Val Phe Ile Phe Pro Pro Ser Asp Glu
        115                 120                 125
Gln Leu Lys Ser Gly Thr Ala Ser Val Val Cys Leu Leu Asn Asn Phe
    130                 135                 140
Tyr Pro Arg Glu Ala Lys Val Gln Trp Lys Val Asp Asn Ala Leu Gln
145                 150                 155                 160
Ser Gly Asn Ser Gln Glu Ser Val Thr Glu Gln Asp Ser Lys Asp Ser
                165                 170                 175
Thr Tyr Ser Leu Ser Ser Thr Leu Thr Leu Ser Lys Ala Asp Tyr Glu
            180                 185                 190
Lys His Lys Val Tyr Ala Cys Glu Val Thr His Gln Gly Leu Ser Ser
        195                 200                 205
Pro Val Thr Lys Ser Phe Asn Arg Gly Glu Cys Gly Thr Asp Lys Thr
    210                 215                 220
His Thr Ser Pro Pro Ser Pro Ala Pro Pro Val Ala Gly Pro Ser Val
225                 230                 235                 240
Phe Leu Phe Pro Pro Lys Pro Lys Asp Thr Leu Met Ile Ser Arg Thr
                245                 250                 255
Pro Glu Val Thr Cys Val Val Val Asp Val Ser His Glu Asp Pro Glu
            260                 265                 270
Val Lys Phe Asn Trp Tyr Val Asp Gly Val Glu Val His Asn Ala Lys
        275                 280                 285
Thr Lys Pro Arg Glu Glu Gln Tyr Asn Ser Thr Tyr Arg Val Val Ser
    290                 295                 300
Val Leu Thr Val Leu His Gln Asp Trp Leu Asn Gly Lys Glu Tyr Lys
305                 310                 315                 320
Cys Lys Val Ser Asn Lys Gly Leu Pro Ser Ser Ile Glu Lys Thr Ile
```

```
                    325                 330                 335
Ser Lys Ala Lys Gly Gln Pro Arg Glu Pro Gln Val Tyr Thr Leu Pro
                340                 345                 350
Pro Ser Arg Asp Glu Leu Thr Lys Asn Gln Val Ser Leu Trp Cys Leu
            355                 360                 365
Val Lys Gly Phe Tyr Pro Ser Asp Ile Ala Val Glu Trp Glu Ser Asn
        370                 375                 380
Gly Gln Pro Glu Asn Asn Tyr Lys Thr Thr Pro Pro Val Leu Asp Ser
385                 390                 395                 400
Asp Gly Ser Phe Phe Leu Tyr Ser Lys Leu Thr Val Asp Lys Ser Arg
                405                 410                 415
Trp Gln Gln Gly Asn Val Phe Ser Cys Ser Val Met His Glu Ala Leu
                420                 425                 430
His Asn His Tyr Thr Gln Lys Ser Leu Ser Leu Ser Pro Gly Lys
                435                 440                 445

<210> SEQ ID NO 32
<211> LENGTH: 343
<212> TYPE: PRT
<213> ORGANISM: Artificial Sequence
<220> FEATURE:
<223> OTHER INFORMATION: VH Sequence

<400> SEQUENCE: 32

His Val Gln Leu Val Gln Ser Gly Ala Glu Val Lys Lys Pro Gly Ser
1               5                   10                  15
Ser Val Lys Val Ser Cys Lys Ala Ser Gly Tyr Thr Phe Thr Asp Phe
                20                  25                  30
Tyr Ile Asn Trp Val Arg Gln Ala Pro Gly Gln Gly Leu Glu Trp Ile
            35                  40                  45
Gly Glu Ile Val Pro Ser Gln Gly Glu Ala Lys Tyr Asn Asp Lys Phe
        50                  55                  60
Lys Ala Arg Val Thr Ile Thr Ala Asp Lys Ser Thr Ser Thr Ala Tyr
65                  70                  75                  80
Met Glu Leu Ser Ser Leu Arg Ser Glu Asp Thr Ala Val Tyr Tyr Cys
                85                  90                  95
Ala Arg Trp Asp Phe Leu Asp Tyr Trp Gly Gln Gly Thr Thr Val Thr
                100                 105                 110
Val Ser Ser Gly Thr Asp Lys Thr His Thr Ser Pro Pro Ser Pro Ala
            115                 120                 125
Pro Pro Val Ala Gly Pro Ser Val Phe Leu Phe Pro Pro Lys Pro Lys
        130                 135                 140
Asp Thr Leu Met Ile Ser Arg Thr Pro Glu Val Thr Cys Val Val Val
145                 150                 155                 160
Asp Val Ser His Glu Asp Pro Glu Val Lys Phe Asn Trp Tyr Val Asp
                165                 170                 175
Gly Val Glu Val His Asn Ala Lys Thr Lys Pro Arg Glu Glu Gln Tyr
                180                 185                 190
Asn Ser Thr Tyr Arg Val Val Ser Val Leu Thr Val Leu His Gln Asp
            195                 200                 205
Trp Leu Asn Gly Lys Glu Tyr Lys Cys Lys Val Ser Asn Lys Gly Leu
        210                 215                 220
Pro Ser Ser Ile Glu Lys Thr Ile Ser Lys Ala Lys Gly Gln Pro Arg
225                 230                 235                 240
Glu Pro Gln Val Tyr Thr Leu Pro Pro Ser Arg Asp Glu Leu Thr Lys
```

```
                    245                 250                 255
Asn Gln Val Ser Leu Ser Cys Ala Val Lys Gly Phe Tyr Pro Ser Asp
                260                 265                 270

Ile Ala Val Glu Trp Glu Ser Asn Gly Gln Pro Glu Asn Asn Tyr Lys
            275                 280                 285

Thr Thr Pro Pro Val Leu Asp Ser Asp Gly Ser Phe Phe Leu Val Ser
        290                 295                 300

Lys Leu Thr Val Asp Lys Ser Arg Trp Gln Gln Gly Asn Val Phe Ser
305                 310                 315                 320

Cys Ser Val Met His Glu Ala Leu His Asn His Tyr Thr Gln Lys Ser
                325                 330                 335

Leu Ser Leu Ser Pro Gly Lys
                340

<210> SEQ ID NO 33
<211> LENGTH: 340
<212> TYPE: PRT
<213> ORGANISM: Artificial Sequence
<220> FEATURE:
<223> OTHER INFORMATION: VL Sequence

<400> SEQUENCE: 33

Asp Val Gln Met Thr Gln Ser Pro Ser Ser Leu Ser Ala Ser Val Gly
1               5                   10                  15

Asp Arg Val Thr Ile Thr Cys Arg Ser Ser Gln Ser Leu Leu His Ser
            20                  25                  30

Asn Gly Asn Thr Tyr Leu His Trp Tyr Gln Gln Lys Pro Gly Lys Ala
        35                  40                  45

Pro Lys Leu Leu Ile Tyr Thr Val Ser Asn Arg Phe Ser Gly Val Pro
    50                  55                  60

Ser Arg Phe Ser Gly Ser Gly Ser Gly Thr Asp Phe Thr Leu Thr Ile
65                  70                  75                  80

Ser Ser Leu Gln Pro Glu Asp Phe Ala Thr Tyr Tyr Cys Ser Gln Ser
                85                  90                  95

Thr His Val Pro Tyr Thr Phe Gly Gly Gly Thr Lys Val Glu Ile Lys
                100                 105                 110

Gly Thr Asp Lys Thr His Thr Ser Pro Pro Ser Pro Ala Pro Pro Val
            115                 120                 125

Ala Gly Pro Ser Val Phe Leu Phe Pro Pro Lys Pro Lys Asp Thr Leu
        130                 135                 140

Met Ile Ser Arg Thr Pro Glu Val Thr Cys Val Val Val Asp Val Ser
145                 150                 155                 160

His Glu Asp Pro Glu Val Lys Phe Asn Trp Tyr Val Asp Gly Val Glu
                165                 170                 175

Val His Asn Ala Lys Thr Lys Pro Arg Glu Glu Gln Tyr Asn Ser Thr
            180                 185                 190

Tyr Arg Val Val Ser Val Leu Thr Val Leu His Gln Asp Trp Leu Asn
        195                 200                 205

Gly Lys Glu Tyr Lys Cys Lys Val Ser Asn Lys Gly Leu Pro Ser Ser
    210                 215                 220

Ile Glu Lys Thr Ile Ser Lys Ala Lys Gly Gln Pro Arg Glu Pro Gln
225                 230                 235                 240

Val Tyr Thr Leu Pro Pro Ser Arg Asp Glu Leu Thr Lys Asn Gln Val
                245                 250                 255

Ser Leu Trp Cys Leu Val Lys Gly Phe Tyr Pro Ser Asp Ile Ala Val
```

```
                260                 265                 270
Glu Trp Glu Ser Asn Gly Gln Pro Glu Asn Asn Tyr Lys Thr Thr Pro
            275                 280                 285

Pro Val Leu Asp Ser Asp Gly Ser Phe Phe Leu Tyr Ser Lys Leu Thr
        290                 295                 300

Val Asp Lys Ser Arg Trp Gln Gln Gly Asn Val Phe Ser Cys Ser Val
305                 310                 315                 320

Met His Glu Ala Leu His Asn His Tyr Thr Gln Lys Ser Leu Ser Leu
                325                 330                 335

Ser Pro Gly Lys
            340

<210> SEQ ID NO 34
<211> LENGTH: 8
<212> TYPE: PRT
<213> ORGANISM: Artificial Sequence
<220> FEATURE:
<223> OTHER INFORMATION: Fab modification

<400> SEQUENCE: 34

Asp Lys Thr His Thr Cys Ala Ala
1               5

<210> SEQ ID NO 35
<211> LENGTH: 17
<212> TYPE: PRT
<213> ORGANISM: Artificial Sequence
<220> FEATURE:
<223> OTHER INFORMATION: Hinge sequence

<400> SEQUENCE: 35

Asp Lys Thr His Thr Cys Pro Pro Cys Pro Ala Pro Glu Leu Leu Gly
1               5                   10                  15

Gly

<210> SEQ ID NO 36
<211> LENGTH: 4
<212> TYPE: PRT
<213> ORGANISM: Artificial Sequence
<220> FEATURE:
<223> OTHER INFORMATION: FR sequence

<400> SEQUENCE: 36

Ser Ala Ser Val
1

<210> SEQ ID NO 37
<211> LENGTH: 4
<212> TYPE: PRT
<213> ORGANISM: Artificial Sequence
<220> FEATURE:
<223> OTHER INFORMATION: FR sequence

<400> SEQUENCE: 37

Asp Arg Val Thr
1

<210> SEQ ID NO 38
<211> LENGTH: 4
<212> TYPE: PRT
<213> ORGANISM: Artificial Sequence
<220> FEATURE:
<223> OTHER INFORMATION: FR sequence
```

```
<400> SEQUENCE: 38

Ser Leu Gln Pro
1

<210> SEQ ID NO 39
<211> LENGTH: 4
<212> TYPE: PRT
<213> ORGANISM: Artificial Sequence
<220> FEATURE:
<223> OTHER INFORMATION: FR sequence

<400> SEQUENCE: 39

Gly Gly Leu Val
1

<210> SEQ ID NO 40
<211> LENGTH: 6
<212> TYPE: PRT
<213> ORGANISM: Artificial Sequence
<220> FEATURE:
<223> OTHER INFORMATION: FR sequence

<400> SEQUENCE: 40

Asn Ala Lys Asn Ser Leu
1               5

<210> SEQ ID NO 41
<211> LENGTH: 4
<212> TYPE: PRT
<213> ORGANISM: Artificial Sequence
<220> FEATURE:
<223> OTHER INFORMATION: FR sequence

<400> SEQUENCE: 41

Leu Gln Met Asn
1

<210> SEQ ID NO 42
<211> LENGTH: 18
<212> TYPE: PRT
<213> ORGANISM: Artificial Sequence
<220> FEATURE:
<223> OTHER INFORMATION: Hinge sequence

<400> SEQUENCE: 42

Gly Thr Asp Lys Thr His Thr Ser Pro Pro Cys Pro Ala Pro Pro Val
1               5                   10                  15

Ala Gly

<210> SEQ ID NO 43
<211> LENGTH: 18
<212> TYPE: PRT
<213> ORGANISM: Artificial Sequence
<220> FEATURE:
<223> OTHER INFORMATION: Hinge sequence

<400> SEQUENCE: 43

Gly Thr Asp Lys Thr His Thr Cys Pro Pro Ser Pro Ala Pro Pro Val
1               5                   10                  15

Ala Gly

<210> SEQ ID NO 44
<211> LENGTH: 18
<212> TYPE: PRT
<213> ORGANISM: Artificial Sequence
```

```
<220> FEATURE:
<223> OTHER INFORMATION: Hinge sequence

<400> SEQUENCE: 44

Gly Thr Asp Lys Thr His Thr Ser Pro Pro Ser Pro Ala Pro Pro Val
1               5                   10                  15

Ala Gly
```